US007635464B2

(12) United States Patent
Hogg

(10) Patent No.: US 7,635,464 B2
(45) Date of Patent: Dec. 22, 2009

(54) SELECTIVE TARGETING OF APOPTOTIC CELLS

(75) Inventor: Philip John Hogg, Malabar (AU)

(73) Assignee: New South Innovations Pty Limited, UNSW Sydney NSW (AU)

( * ) Notice: Subject to any disclaimer, the term of this patent is extended or adjusted under 35 U.S.C. 154(b) by 263 days.

(21) Appl. No.: 10/494,822

(22) PCT Filed: Nov. 8, 2002

(86) PCT No.: PCT/AU02/01523

§ 371 (c)(1),
(2), (4) Date: Nov. 24, 2004

(87) PCT Pub. No.: WO03/039564

PCT Pub. Date: May 15, 2003

(65) Prior Publication Data

US 2005/0101524 A1    May 12, 2005

(30) Foreign Application Priority Data

Nov. 8, 2001    (AU)    ................................ PR8746

(51) Int. Cl.
  *A61K 49/00*    (2006.01)
  *A61K 49/04*    (2006.01)
  *A61B 5/055*    (2006.01)
  *A61B 5/00*    (2006.01)
  *A61B 10/00*    (2006.01)
(52) U.S. Cl. ........................ 424/9.1; 424/9.3; 424/9.4; 424/9.6
(58) Field of Classification Search ........................ None
See application file for complete search history.

(56) References Cited

U.S. PATENT DOCUMENTS 3,883,659 A    5/1975    Friedheim et al.

FOREIGN PATENT DOCUMENTS

| FR | 2 781 674 | 7/1998 |
|---|---|---|
| WO | WO 98/51297 | 11/1998 |
| WO | WO 99/18798 | 4/1999 |
| WO | WO 99/55344 | 11/1999 |
| WO | WO 00/56742 | 9/2000 |
| WO | WO 01/21628 | 3/2001 |

OTHER PUBLICATIONS

Donoghue et al. Protein Science 2000, 9, 2436-2445.*
Namgung et al. The Journal of Neuroscience 2000, 20(17), 6442-6451.*
Loiseau et al. Antimicrobial Agnets and Chemotherapy 2000, 44(11), 2954-2961.*
PCT/AU02/01523, ISR, International Search Report.
Bazarbachi, et al., "Aresenic Trioxide and Interferon-α Synergize to Induce Cell Cycle Arrest and Apoptosis in Human T-Cell Lymphotropic Virus Type I-Transformed Cells", *Blood*, vol. 93, No. 1 (Jan. 1), 1999: pp. 278-283.
Fairlamb, Alan H., et al., "Trypanothione is the Primary Target for Arsenical Drugs Against African Trypanosomes," *PNAS*, vol. 86 (1989) pp. 2607-2611.
Fairlamb, Alan H. & Cerami, Anthony, "Metabolism and Functions of Trypanothione in the Kinetoplastida," *Annu. Rev. Microbiol.*, vol. 46 (1992) pp. 695-729.
Cunningham, Mark L., et al., "Mechanism of inhibition of Trypanothione Reductase and Glutathione Reductase by Trivalent Organic Arsenicals," *FEBS*, vol. 221 (1994) pp. 285-295.
Bhargava, Kuldeep K., et al., "Effect of Arsenical Drugs on Glutathione Metabolism of *Litomosoides carinii*," *Molecular and Biochemical Parasitology*, vol. 9 (1983) pp. 29-35.
Carter, Nicola S. & Fairlamb, Alan H., "Arsenical-Resistant Trypanosomes Lack an Unusual Adenosine Transporter," *Nature*, vol. 361 (1993) pp. 173-176.
Pisciotto, Patricia T. & Graziano, Joseph H., "Induction of Mucosal Glutathione Synthesis by Arsenic," *Biochemical et Biophysica Acta*, vol. 628 (1980) pp. 241-243.
Lawrence, David A., et al., "Surface Thiols of Human Lymphocytes and Their Changes after in Vitro and In Vivo Activation," *Journal of Leukocyte Biology*, vol. 60, (1996) pp. 611-618.
Ryser, Hugues J.-P., et al., "Cell Surface Sulfhydryls are Required for the Cytotoxicity of Diphtheria Toxin but not of Ricin in Chinese Hamster Ovary Cells," *Journal of Biological Chemistry*, vol. 266, No. 28 (1991) pp. 18439-18442.
Mandel, Richard, et al., "Inhibition of a Reductive Function of the Plasma Membrane by Bacitracin and Antibodies Against Protein Disulfide-Isomerase," *PNAS*, vol. 90 (1993) pp. 4112-4116.
Couët, Jacques, et al., "Cell Surface Protein Disulfide-Isomerase is Involved in the Shedding of Human Thyrotropin Receptor Ectodomain," *Biochemistry*, vol. 35 (1996) pp. 14800-14805.
Krishna Rao, A. S. M. & Hausman, R. E., "cDNA for R-Cognin: Homology with a Multifunctional Protein," *PNAS*, vol. 90 (1993) pp. 2950-2954.
Zai, Adrian, et al., "Cell-Surface Protein Disulfide Isomerase Catalyzes Transnitrosation and Regulates Intracellular Transfer of Nitric Oxide," *The Journal of Clinical Investigation*, vol. 103, No. 3 (1999) pp. 393-399.
Essex, David W., et al., "Localization of Protein Disulfide Isomerase to the External Surface of the Platelet Plasma Membrane," *Blood*, vol. 86, No. 6 (1995) pp. 2168-2173.
Essex, David W., et al., "Protein Disulphide Isomerase Mediates Platelet Aggregation and Secretion," *British Journal of Haematology*, vol. 104 (1999) pp. 448-454.
Täger, Michael, et al., "Membrane-Bound Proteindisulfide Isomerase (PDI) is Involved in Regulation of Surface Expression of Thiols and Drug Sensitivity B-CLL Cells," *Experimental Hematology*, vol. 25 (1997) pp. 601-607.

(Continued)

*Primary Examiner*—Ernst V Arnold
(74) *Attorney, Agent, or Firm*—McDonnell Boehnen Hulbert & Berghoff LLP

(57) ABSTRACT

The invention relates to a method of selectively targeting an active agent (or agent capable of becoming an active agent) to apoptotic cells in a vertebrate, comprising administering to said vertebrate a system comprising an arsenoxide (or arsenoxide equivalent) compound and said agent, wherein said system selectively targets apoptotic cells.

33 Claims, 15 Drawing Sheets

OTHER PUBLICATIONS

Stathakis, Paul, et al., "Generation of Angiostatin by Reduction and Proteolysis of Plasmin: Catalysis by a Plasmin Reductase Secreted by Cultured Cells," *J. Bio. Chem.*, vol. 272, No. 33 (1997) pp. 20641-20645.

Stathakis, Paul, et al., "Angiostatin Formation Involves Disulfide Bond Reduction and Proteolysis in Kringle 5 of Plasmin," *J. Bio. Chem.*, vol. 274, No. 13 (1999) pp. 8910-8916.

Bannai, Shiro & Tsukeda, Hohko, "The Export of Glutathione from Human Diploid Cells in Culture," *J. Bio. Chem.*, vol. 254, No. 9 (1979) pp. 3444-3450.

Holmgren, Arne, "Thioredoxin and Glutaredoxin Systems," *J. Bio. Chem.*, vol. 264, No. 24 (1989) pp. 13963-13966.

Rosén, Anders, et al., "A CD4+ T Cell Line-Secreted Factor, Growth, Promoting for Normal and Leukemic B Cells, Identified as Thioredoxin," *International Immunology*, vol. 7, No. 4 (1995) pp. 625-633.

Happersberger, Peter H., & Glocker, Michael O., "A Mass Spectrometric Approach to the Characterization of Protein Folding Reactions," *Eur. Mass Spectrom*, vol. 4 (1998) pp. 209-214.

Halestrap, Andrew P., et al., "The Permeability Transition Pore Complex: Another View," *Biochimie*, vol. 84 (2002) pp. 153-166.

Desagher, Solange & Martinou, Jean-Claude, "Mitochondria as the Central Control Point of Apoptosis," *Trends in Cell Biology*, vol. 10 (2000) pp. 369-377.

Fantin, Valeria R., et al., "A Novel Mitochondriotoxic Small Molecule that Selectively Inhibits Tumor Cell Growth," *Cancer Cell*, vol. 2 (2002) pp. 29-42.

Belzacq, Anne-Sophie, et al., "The Adenine Nucleotide Translocator in Apoptosis," *Biochimie*, vol. 84 (2002) pp. 167-176.

McStay, Gavin P., et al., "Role of Critical Thiol Groups on the Matrix Surface of the Adenine Nucleotide Translocase in the Mechanism of the Mitochondrial Permeability Transition Pore," *Biochem. J.*, vol. 367 (2002) pp. 541-548.

Koch, Alisa Erika, "The Role of Angiogensis in Rheumatoid Arthritis: Recent Developments," *Ann. Rheum. Dis.*, vol. 59 (2000) pp. 65-71.

Hayes, Andrew J., "Angioneogenesis in Rheumatoid Arthritis," *The Lancet*, vol. 354 (1999) pp. 423-424.

Anonymous, "Arthritis: The Aging Populations of Developed Countries are Likely to present a Growing market for Arthritis Therapies," *Nature Biotechnology*, vol. 18 (2000) pp. IT12-IT14.

Ades, Edwin W., et al., "HMEC-1: Establishment of an Immortalized Human Microvascular Endothelial Cell Line," *The Journal of Investigative Dermatology*, vol. 99, No. 6 (1992) pp. 683-690.

Andree, Harry A. M., et al., "Blinding of Vascular Anticoagulant α (VACα) to Planar Phospholipid Bilayers," *J. Bio. Chem.*, vol. 265, No. 9 (1990) pp. 4923-4926.

Blankenberg, F.G. & Strauss, H. W., "Will Imaging of Apoptosis Play a Role in clinical Care? A tale of Mice and Men," *Apoptosis*, vol. 6 (2001) pp. 117-123.

Dahmoun, M., et al., "Apoptosis, Proliferation, and Sex Hormone Receptors in Superficial Parts of Human Endometrium at the End of the Secretory Phase," *The Journal of Clinical Endocrinology & Metabolism*, vol. 84, No. 5 (1999) pp. 1737-1743.

Daly, John M., et al., "Neu Differentiation Factor Induces ERbB2 Down-Regulation and Apoptosis of ErbB2-Overexpressing Breast Tumor Cells," *Cancer Research*, vol. 57 (1997) pp. 3804-3811.

Donoghue, Neil, et al., "Presence of Closely Spaced Protein Thiols on the Surface of Mammalian Cells," *Protein Science*, vol. 9, (2000) pp. 2436-2445.

Fisher, Karen L., et al., "Cloning and Expression of Human Tissue Factor cDNA," *Thrombosis Research*, vol. 48 (1987) pp. 89-99.

Gottlieb, Roberta A. & Engler, Robert L., "Apoptosis in Myocardial Ischemia-Reperfusion," *Ann. N. Y. Acad. Sci.*, vol. 874 (1999) pp. 412-426.

Hofstra, Leo, et al., "Visualisation of Cell Death in vivo in Patients with Acute Myocardial Infarction," *The Lancet*, vol. 356 (2000) pp. 209-212.

Huang, Xianming, et al., "Tumor Infraction in Mice by Antibody-Directed Targeting of Tissue Factor to Tumor Vasculature," *Science*, vol. 275 (1997) pp. 547-550.

Jiang, Xing-Mai, et al., "Redox Control of Exofacial protein Thiols/Disulfides by protein Disulfide Isomerase," *J. Bio. Chem.*, vol. 274, No. 4 (1999) pp. 2416-2423.

Ju, Shyr-Te, et al., "Molecular and Cellular Mech Regulating T and B Cell Apop Through Fax/FasL Interaction," *Intern, Rev. Immunol.*, vol. 18 (1999) pp. 485-513.

Krams, Sheri M. & Martinez, Olivia M., "Apoptosis as a Mechanism of Tissue Injury in Liver Allograft Rejection," *Seminars in Liver Disease*, vol. 18, No. 2 (1998) pp. 153-167.

Nihei, Oscar K., et al., "Pharmacologic Properties of $P_{2Z}/P2X_7$ Receptor Characterized in Murine Dendritic Cells: Role on the Induction of Apoptosis," *Blood*, vol. 96, No. 3 (2000) pp. 996-1004.

O'Reilly, Michael S., et al., "Angiostatin: A Novel Angiogensis Inhibitor That Mediates the Suppression of Metastases by a Lewis Lung Carcinoma," *Cell*, vol. 79 (1994) pp. 315-328.

Parker, Jane E. & Multi, Ghulam J., "The Role of Apoptosis in the Pathogenesis of the Myelodysplastic Syndromes," *Int. J. Hematol.*, vol. 73 (2001) pp. 416-428.

Ramachandran, Anup et al., "Apoptosis in the Intestinal Epitheliam: Its Relevance in Normal and Pathophysiological Conditions," *Journal of Gastroenterology and Hepatology*, vol. 15 (2000) pp. 109-120.

Riddles, Peter W., et al., "Reassessment of Ellman's Reagent," *Methods in Enzymology*, vol. 91 (1983) pp. 50-61.

Rimon, Galia et al., "Rapid Communication: Increased Surface Phosphatidylserine Is an Early Marker of Neuronal Apoptosis," *Journal of Neuroscience Research*, vol. 48 (1997) pp. 563-570.

Rupnow, B. A. & Know, S. J., "The Role of Radiation-Induced Apoptosis as a determinant of tumor Responses to radiation Therapy," *Apoptosis*, vol. 4, No. 2 (1999) pp. 115-143.

Ŝtefanec, Tihomir, "Endothelial Apoptosis, Could it Have a Role in the pathogenesis and Treatment of a Disease?," *Chest*, vol. 117, No. 3 (2000) pp. 841-854.

Stone, Martin J., et al., "Recombinant Soluble Human Tissue Factor Secreted by *Saccharomyces cerevisiae* and Refolded from *Escherichia coli* inclusion Bodies: Glycosylation of Mutants, Activity and Physical Characterization," *Biochem J.*, vol. 310 (1995) pp. 605-614.

Thompson, Craig B., "Apoptosis in the pathogenesis and Treatment of Disease," *Science*, vol. 267 (1995) pp. 1456-1462.

Vermes, István, et al., "A Novel Assay for Apoptosis Flow Cytomertic Detection of Physphatidylserine Expression on Early Apoptoic Cells Using Fluorescein labeled Annexin V," *Jounral of Immunological Methods*, vol. 184 (1995) pp. 39-51.

Virginio, C., et al., "Kinetics of Cell Lysis, Dye Uptake and Permeability Changes in Cells Expressing the Rat $P2X_7$ Receptor," *Journal of Physiology*, vol. 519 (1999) pp. 335-346.

Weissleder, Ralph, et al., "In Vivo Imaging of Tumors with Protease-Activated Near-Infrared Fluorescent Probes," *Nature Biotechnology*, vol. 17 (1999) pp. 375-378.

Adams, Earle, et al., "Chemistry of Organometalloid Complexes with potential Antidotes: Structure of an Organoarsenic(III) Dithiolate Ring," *Inorg. Chem.*, vol. 29 (1990) pp. 1500-1503.

Greenberg, N. M., et al., "Prostate Cancer in a Transgenic Mouse," *PNAS*, vol. 92 (1995) pp. 3439-3443.

Hofstra, L., et al. "In Vivo Detection of Apoptosis in an Intracardiac Tumor," *JAMA*, vol. 285, No. 14 (2001) pp. 1841-1842.

Kaufmann, Scott H., "Cell Death Induced by Topoisomerase-Targeted Drugs: More Questions Than Answers," *Biochimica et Biophysica Acta*, vol. 1400 (1998) pp. 195-211.

Mattson, Mark P., "Apoptosis in Neurodegenerative Disorders," *National Review/Molecular Cell Biology*, vol. 1 (2000) pp. 120-129.

Novia, Robert, "Protein Disulfide Isomerase: the Mutifunctional Redox Chaperone of the Endoplasmic Reticulum," *Cell & Developmental Biology*, vol. 10 (1999) pp. 481-493.

Pronk, Gijsbertus J., et al., "Requirement of an Ice-Like Protease for Induction of Apoptosis and Ceramide Generation by REAPER," *Science*, vol. 271 (1996) pp. 80-810.

Thornberry, Nancy A. & Lasebnik, Yuri, "Caspases: Enemies Within," *Science*, vol. 281 (1998) pp. 1312-1316.

Zhu, Huijun, et al., "An Ice-Like Protease is a Common Mediator of Apoptosis Induced by Diverse Stimuli in Human Monocytic THP.1 Cells," *FEBS Letters*, vol. 374 (1995) pp. 303-308.

Gitler, Carlos, et al., "General Method to Identify and Enrich Vicinal Thiol Proteins Present in Intact Cells in the Oxidized, Disulfide State," *Analytical Biochemistry*, vol. 252 (1997) pp. 48-55.
Beilstein Registry No. 21688.
Beilstein Registry No. 22377.
Beilstein Registry No. 51552.
Beilstein Registry No. 111664.
Beilstein Registry No. 116874.
Beilstein Registry No. 273946.
Beilstein Registry No. 358898.
Beilstein Registry No. 3126376.
Beilstein Registry No. 3129248.
Beilstein Registry No. 3135458.
Beilstein Registry No. 3139905.
Beilstein Registry No. 3141604.
Beilstein Registry No. 3152231.
Beilstein Registry No. 3233826.
Beilstein Registry No. 3235693.
Beilstein Registry No. 3254079.
Beilstein Registry No. 3273842.
Beilstein Registry No. 3275319.
Beilstein Registry No. 3285106.
Beilstein Registry No. 3293148.
Beilstein Registry No. 3296676.
Beilstein Registry No. 3298747.
Beilstein Registry No. 3319010.
Beilstein Registry No. 3341328.
Beilstein Registry No. 3344707.
Beilstein Registry No. 3531489.

Gill, B.S., "Chemotherapeutic Susceptibility of Trypanosoma to some Arsenicals and Suramin-Tryparsamid Complex", *Acta Vet.*, 1971, vol. 40, No. 2, pp. 209-214. (English Abstract Only).
Yuki, Hidetaka, et al., "Synthesis of Purine and Pyrimidine Derivatives of Arsonic Acid", *Chem. Pharm. Bull.*, 1967, vol. 15, No. 7, pp. 1052-1055.
Donahue, Neil, et al., "(9) Identification of Redox-Active Proteins on Cell Surface", *Methods in Enzymology*, vol. 352, pp. 101-112.
Hnatowich DJ et al., "Investigations of Avidin and Biotin for Imaging Applications," 1987, The Journal of Nuclear Medicine 8: 1294-1302.
Donoghue, N. et al., "Characterization of Redox-Active Proteins on Cell Surface", Methods in Enzymology, vol. 348, 2002, 76-86.
Sieburg, "Aus dem Institut fur Pharmakologie und physiologische Chemie der Universitat zu Rostock. Ueber Ester aromatischer Arsenverbindungen (der p-Benzarsinsaure) mit Aminosauren und hoheren Alkoholen", Zur Biologie aromatischer Arsenverbindungen, Ztschr. f. physiol. Chem., 1916, 97, Heft 2/3, 224-245.
Hummel et al., "Modification of Bovine Pancreatic Ribonuclease A with the Site-Specific Reagent 4-Arsono-2-nitrofluorobenzene. Spectrophotometric Titration of Arsononitrophenyl Ribonuclease A Derivatives", Biochemistry, 1981, vol. 20, 4843-4852.
Hummel et al., "Chemical modification of ribonuclease A with 4-arsono-2-nitrofluorobenzene", Int. J. Peptide Protein Res., 1984, vol. 24, 1-13.
Delnomdedieu et al., "Reduction and binding of arsenate and dimethylarsinate by glutathione: a magnetic resonance study", Chemico Biological Interactions, 1994, vol. 90, 139-155.

* cited by examiner

SELECTIVE TARGETING OF APOPTOTIC CELLS

TECHNICAL FIELD

The present Invention relates generally to targeted delivery of active agents, wherein the active agents are generally therapeutic or diagnostic agents. More particularly, the present invention relates to a method of selectively targeting an active agent to apoptotic cells in a vertebrate by administering a system comprising an arsenoxide (or arsenoxide equivalent) compound and at least one active agent, wherein the arsenoxide compound selectively targets apoptotic cells and delivers the active agent, such as therapeutic or detectable agents, to apoptotic cells and their environ.

BACKGROUND

Programmed cell death, or apoptosis, plays an integral role in cell turnover. Imbalance of apoptosis characterised by a marked increase or decrease of apoptosis relative to cell regeneration, is often associated with disease (Thompson, 1995). For example, excessive apoptosis is characteristic of vascular disorders (Stefanec, 2000), neurodegenerative diseases (Rimon et at. 1997), myelodysplastic syndromes (Parker & Mufti, 2001), ischaemia/reperfusion injury (Gottlieb & Engler, 1999), organ transplant rejection (Krams and Martinez, 1998), tumours and cancers, among others.

However, there are no specific measures of apoptosis used in patient diagnosis or therapy. This is in part due to the lack of a convenient and sensitive marker to monitor apoptosis in vivo. Therefore, a selective marker for apoptotic cells would be advantageous in disease diagnosis and therapy, and would also be of interest for imaging normal cell processes.

Accordingly, there is a need to selectively target active agents to sites of therapeutic or diagnostic interest in particular, there is a need to selectively target agents to apoptotic cells.

The present invention relates to a method of targeting an active agent to apoptotic cells in a vertebrate, comprising administering to a vertebrate a system comprising an arsenoxide (or arsenoxide equivalent) compound and an active agent, wherein the system selectively targets apoptotic cells. The arsenoxide (or arsenoxide equivalent) compound functions primarily as a targeting agent for delivering an active agents such as a therapeutic or imaging agent, to apoptotic cells with a relatively high degree of specificity. A particular advantage of the present invention is that the arsenoxide (or arsenoxide equivalent) compound is selectively taken up by apoptotic cells, and binds to a number of proteins within the cell.

SUMMARY OF THE INVENTION

According to a first embodiment of the invention there is provided a method of selectively targeting an active agent (or agent capable of becoming an active agent) to apoptotic cells in a vertebrate, comprising administering to said vertebrate a system comprising an arsenoxide (or arsenoxide equivalent) compound and said agent wherein said system selectively targets apoptotic cells.

Typically, the system comprises an arsenoxide (or arsenoxide equivalent) compound linked to at least one active agent, or agent capable of becoming an active agent More typically, the system comprises:

(i) a first component comprising an arsenoxide (or arsenoxide equivalent) compound linked to a first binding member, and (ii) a second component, comprising a second binding member, wherein said second binding member is an active agent, or an agent capable of becoming an active agent.

Typically, the first binding member is an enzyme and the second binding member is a substrate for the enzyme. Typically, the substrate for the enzyme is a pro-agent which is converted to an active agent by the enzyme. Still more typically, the enzyme substrate is a prodrug which is converted to an active drug by the enzyme.

Even more typically, the system comprises:

(i) a first component comprising an arsenoxide (or arsenoxide equivalent) compound linked to a first binding member; and (ii) a second component comprising a second binding member linked to at least one active agent (or agent capable of becoming an active agent).

Typically, the first binding member is biotin and the second binding member is avidin or streptavidin. Still typically, the first binding member is avidin or streptavidin and the second binding member is biotin.

Still typically, the first binding member is biotin, the second binding member is avidin or streptavidin, and the second binding member is indirectly linked to an active agent by virtue of a further binding interaction between the avidin or streptavidin and at least one further biotin moiety which is directly linked to the active agent.

Typically, the first binding member is methotrexate and the second binding member is dihydrofolate reductase (DHFR). Still typically, the first binding member is dihydrofolate reductase and the second binding member is methotrexate.

Typically, the first binding member is hirudin and the second binding member is thrombin. Still typically, the first binding member is thrombin and the second binding member is hirudin.

Typically, the first binding member is an antigen and the second binding member is an antibody.

Typically, the second binding member is linked directly to an active agent. Still typically, the second binding member is indirectly linked to an active agent. Even more typically, indirect linking between the active agent and the second binding member is by virtue of a further binding interaction between the second binding member and at least one further binding member, wherein the further binding member is directly linked to the active agent.

Yet soil more typically, the system comprises:

(i) a first component comprising an arsenoxide (or arsenoxide equivalent) compound linked to a first binding member, (ii) a second component comprising a second binding member linked to an enzyme, and (iii) a substrate for said enzyme.

Typically, the substrate for said enzyme is a pro-agent which is converted to an active agent by the enzyme. Typically, the pro-agent is a prodrug.

Typically, the active agent is a therapeutic agent or a diagnostic agent.

Typically, the therapeutic agent includes agents such as radionucleotides; chemotherapeutic agents; cytotoxins; coagulants; growth factors, cytokines; bacterial, plant, or fungal endotoxins.

Typical radionucleotides suitable for use in the invention are selected from the group consisting of: $^{3}H$, $^{11}C$, $^{14}C$, $^{15}O$, $^{13}N$, $^{32}P$, $^{33}P$, $^{35}S$, $^{18}F$, $^{125}I$, $^{127}I$, $^{111}In$, $^{105}Rh$, $^{153}Sm$, $^{67}Cu$, $^{67}Ga$, $^{166}Ho$, $^{177}Lu$, $^{186}Re$, $^{188}Re$, and $^{99m}Tc$.

Typical chemotherapeutic agents include: adriamycin, taxol, fluorouricil, melphalan, cisplatin, alpha interferon, vincristine, vinblastine, angloinhibins, TNP470, pentosan polysulfate, platelet factor 4, angiostatin, LM-609, SU-101, CM-101, Techgalan, thalidomide, SP-PG and the like. Other typical chemotherapeutic agents include alkylating agents such as nitrogen mustards including mechloethamine, melphan, chlorambucil, cyclophosphamide and ifosfamide, nitrosoureas including carmustine, lomustine, semustine and streptozocin; alkyl sulfonates including busulfan; triazines including dicarbazine; ethyenimines including thiotepa and hexamethyimelamine; folic acid analogues including methotrexate; pyrimidine analogues including 5-fluorouracil, cytosine arabinoside; purine analogues including 6-mercaptopurine and 6-thioguanine; antitumour antbiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar, and regimens such as COMP (cyclophosphamide, vincristine, methotrexate and prednisone), etoposide, mBACOD (methotrexate, bleomycin, doxorubicin, cyclophosphamide, vincristine and dexamethasone), and PROMACE/MOPP (prednisone, methotrexate (w/leucovin rescue), doxorubicin, cyclophosphamide, taxol, etoposide/mechlorethamine, Vincristine, prednisone and procarbazine).

Typical cytotoxins include ricin.

Typical bacterial, plant, fungal endotoxins are selected from the group consisting of: ribosome inactivating protein, diphtheria toxin, pseudomonas endotoxin, A chain toxin, α-sarcin, aspergillin, restrictocin, and ribonucleases.

Typically, the diagnostic agent is an imaging agent. More typically, substances which function as diagnostic agents are well known to those of ordinary skill in the art and include, fluorescent labels, radionucleotides, paramagnetic ions, X-ray imaging agents, chemiluminescent labels or labels which may be detected through a secondary enzymatic or binding step. Typical fluorescent labels suitable for use in the system of the invention include Cy™5.5, fluorescein. Other commercial fluorescent probes suitable for use in the present invention are listed in the *Handbook of Fluorescent Probes and Research Products*, 8$^{th}$ Edition, the contents of which are incorporated herein by reference.

Typical radionucleotides suitable for use as an imaging agent in the invention are selected from the group consisting of:$^{3}$H, $^{11}$C, $^{14}$C, $^{15}$O, $^{13}$N, $^{32}$P, $^{33}$P, $^{35}$S, $^{18}$F, $^{125}$I, $^{127}$I, $^{111}$In, $^{105}$Rh, $^{153}$Sm, $^{67}$Cu, $^{67}$Ga, $^{166}$Ho, $^{177}$Lu, $^{186}$Re, $^{188}$Re, and $^{99m}$Tc.

Typically, paramagnetic ions are selected from the group consisting of chromium(III), gadolinium(III), iron(II), iron (III), holmlum(III), erbium(III), manganese(II), nickel(II), copper(II), neodymium(III), yttrium(III), samarium(III), and dysprosium(III). More typically, the paramagnetic ion is gadolinium(III).

Typically, X-ray imaging agents are selected from the group consisting of gold(III), lead(II). lanthanum(III) and bismuth(III).

Typically, the active agent resides within a vehicle for delivery of said agent. More typically, the vehicle For the active agent is a liposome.

Typically, the arsenoxide (or arsenoxide equivalent) compound targets apoptotic cells. More typically, the arsenoxide (or arsenoxide equivalent) compound is of the formula (I):

$$A-(L-Y)p \qquad (I)$$

wherein

A comprises at east one pendant group;

L comprises any suitable linker and/or spacer group;

Y comprises at least one arsenoxide or arsenoxide equivalent;

p is an integer from 1 to 10.

Typically, the sum total of carbon atoms in A and L together, is greater than 6.

With reference to the compound of formula (I) suitable for use in the present invention, typically, A is selected from the group consisting of natural, unnatural and synthetic amino acids, hydrophilic amines, peptides, polypeptides, oligosaccharides, and thiol containing proteins, or a combination thereof. More typically, A is selected from the group consisting of glutathione, glucosamine, cysteinylglycine, cysteic acid, aspartic acid, glutamic acid, lysine, and arginine, and wherein the sulfur atom of each sulfur containing compound may be optionally oxidised to form a sulfoxide or sulfone.

Amino acid side chains are known to those of skill in the art and are listed, for example, in standard reference texts such as King and Stansfield, "A Dictionary of Genetics", 4$^{th}$ Edition, Oxford University Press, 1990, the contents of which are incorporated herein by reference.

Even more typically, A is glutathione.

Typically, p is an integer from 1 to 5. Yet still more typically, p is 1.

Typically, L corresponds to $(XBX')_nB'$. Typically, n is an integer from 0 to 20, more typically 0 to 15, even more typically 0 to 10, still more typically 0 to 5.

Still in accordance with the arsenoxide compounds suitable for use in the present invention, the following relates to $(XBX')_nB'$.

Typically, X is selected from the group consisting of —NR, —S(O)—, —S(O)O—, —S(O)$_2$—, —S(O)$_2$O—, —C(O)—, —C(S)—, —(O)O—, C(S)O—, —C(S)S—, —P(O)(R$_1$)—, and —P(O)(R$_1$)O—, or is absent;

B is selected from the group consisting of C$_1$-C$_{10}$ alkylene, C$_2$-C$_{10}$ alkenylene, C$_2$-C$_{10}$ alkynylene, C$_3$-C$_{10}$ cycloalkylene, C$_5$-C$_{10}$ cycloalkenylene, C$_3$-C$_{10}$ heterocycloalkylene, C$_5$-C$_{10}$ heterocycloalkylene, C$_6$-C$_{12}$ arylene, heteroarylene and C$_2$-C$_{10}$ acyl;

X' is selected from the group consisting of —NR—, —O—, —S—, —Se—, —S—S—, S(O)—, —OS(O)—, OS(O)O—, —OS(O)$_2$, —OS(O)$_2$O—, —S(O)O—, —S (O)$_2$—, —S(O)$_2$O—, —OP(O)(R$_1$)O—, —OP(O)(R$_1$)OP (O)(R$_1$)O—, —C(O)—, —C(S)—, —C(O)O—, C(S)O—, —C(S)S—, —P(O)(R$_1$)—, —P(O)(R$_1$)O—, and

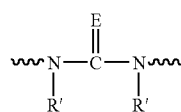

or is absent; wherein E is O, S, Se, NR, or N(R)$_2$+;

n is 0, 1 or 2; and

B' is selected from the group consisting of C$_1$-C$_{10}$ alkylene, C$_2$-C$_{10}$ alkenylene, C$_2$-C$_{10}$ alkynylene, C$_3$-C$_{10}$ cycloalkylene, C$_5$-C$_{10}$ cycloalkenylene, C$_3$-C$_{10}$ heterocycloalkylene, C$_5$-C$_{10}$ heterocycloalkylene, C$_6$-C$_{12}$ arylene, and heteroarylene or is absent; and wherein each R is independently selected from the group consisting of hydrogen, C$_1$-C$_{10}$ alkyl, C$_2$-C$_{10}$ alkenyl, C$_2$-C$_{10}$ alkynyl, C$_3$-C$_{10}$ cycloalkyl, C$_5$-C$_{10}$ cycloalkenyl, C$_3$-C$_{10}$ heterocycloalkyl, C$_5$-C$_{10}$ heterocycloalkenyl, C$_6$-C$_{12}$ aryl, heteroaryl, OR$_2$ and C$_2$-C$_{10}$ acyl;

R' is the same as R or two R' may be taken together with the nitrogen atoms to which they are attached to form a 5 or 6-membered saturated or unsaturated heterocyclic ring;

each $R_1$ is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, halo, $OR_2$ and $N(R)_2$;

each $R_2$ is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl and —C(O)$R_5$;

each $R_5$ is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkoxy, $C_3$-$C_{10}$ alkenyloxy, $C_3$-$C_{10}$ alkynyloxy, $C_3$-$C_{10}$ cycloalkyloxy, $C_5$-$C_{10}$ cycloalkenyloxy, $C_3$-$C_{10}$ heterocycloalkyloxy, $C_5$-$C_{10}$ heterocycloalkenyloxy, $C_6$-$C_{12}$ aryloxy, heteroaryloxy, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroarylthio, OH, SH and $N(R)_2$;

wherein for each instance that B and/or B' is arylene, the substituents directly attached to the respective arylene rings (including arsenoxide or arsenoxide equivalent) may be in a para-, meta- or ortho- relationship; and wherein each alkylene, alkenylene, alkynylene, cycloalkylene, cycloalkenylene, heterocycloalkylene, heterocycloalkenylene, arylene, heteroarylene and acyl may be independently substituted with hydrogen, halogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ hetercycloalkenyl, $C_6$-$C_{12}$ aryl, heteroaryl, cyano, cyanate, isocyanate, $OR_{2a}$, $SR_6$, nitro, arsenoxide, —S(O)$R_3$, —OS(O)$R_3$, —S(O)$_2R_3$, —OS(O)$_2R_3$, —P(O)$R_4R_4$, —OP(O)$R_4R_4$, —N(R")$_2$, —NRC(O)(CH$_2$)$_m$Q, —C(O)$R_5$;

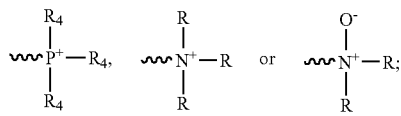

wherein R, $R_1$ and $R_5$ are as defined above; and $R_{2a}$ is selected from the group consisting of hydrogen, $C_1$-$C_5$ alkyl, $C_2$-$C_5$ alkenyl, $C_2$-$C_5$ alkynyl, $C_3$-$C_{10}$ cycloalkyl, $C_5$-$C_{10}$ cycloalkenyl, $C_6$-$C_{12}$ aryl, —S(O)$R_3$, —S(O)$_2R_3$, —P(O)(R$_4$)$_2$, N(R)$_2$ and —C(O)$R_5$;

each $R_3$ is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkoxy, $C_3$-$C_{10}$ alkenyloxy, $C_3$-$C_{10}$ alkynyloxy, $C_3$-$C_{10}$ cycloalkyloxy, $C_5$-$C_{10}$ cycloalkenyloxy, $C_3$-$C_{10}$ heterocycloalkyloxy, $C_5$-$C_{10}$ heterocycloalkenyloxy, $C_6$-$C_{12}$ aryloxy, heteroaryloxy, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroarylthio and $N(R)_2$;

each $R_4$ is independently selected from the group consisting of hydrogen, $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkoxy, $C_3$-$C_{10}$ alkenyloxy, $C_3$-$C_{10}$ alkynyloxy, $C_3$-$C_{10}$ cycloalkyloxy, $C_5$-$C_{10}$ cycloalkenyloxy, $C_3$-$C_{10}$ heterocycloalkyloxy, $C_5$-$C_{10}$ heterocycloalkenyloxy, $C_6$-$C_{12}$ aryloxy, heteroaryloxy, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroarylthio, halo and $N(R)_2$;

$R_6$ is selected from the group consisting of $C_1$-$C_{10}$ alkyl, $C_2$-$C_{10}$ alkenyl, $C_2$-$C_{10}$ alkynyl, $C_3$-$C_{10}$ cycloalkyl, $C_5$-$C_{10}$ cycloalkenyl, $C_3$-$C_{10}$ heterocycloalkyl, $C_5$-$C_{10}$ heterocycloalkenyl, $C_6$-$C_{12}$ aryl, heteroaryl, $C_1$-$C_{10}$ alkylthio, $C_3$-$C_{10}$ alkenylthio, $C_3$-$C_{10}$ alkynylthio, $C_3$-$C_{10}$ cycloalkylthio, $C_5$-$C_{10}$ cycloalkenylthio, $C_3$-$C_{10}$ heterocycloalkylthio, $C_5$-$C_{10}$ heterocycloalkenylthio, $C_6$-$C_{12}$ arylthio, heteroarylthio, —S(O)$R_3$, —S(O)$R_3$ and —C(O)$R_5$, R" is the same as R or two R" taken together with the N atom to which they are attached may form a saturated, unsaturated or aromatic heterocyclic ring system;

Q is selected from halogen and —OS(O)$_2Q_1$; wherein $Q_1$ is selected from $C_1$-$C_4$ alkyl, $C_1$-$C_4$perfluoroalkyl, phenyl, p-methylphenyl; and m is 1 to 5.

More preferably an arsenoxide compound suitable for use in the present invention is 4(N-(S-glutathionylacetyl)amino)-phenylarsenoxide, which can be abbreviated to GSAO, according to Formula IV:

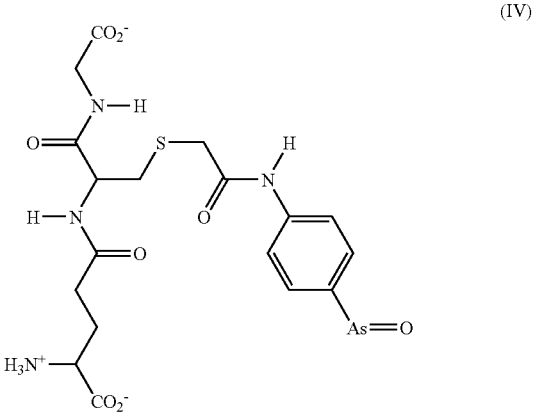

(IV)

Typically, in the arsenoxide compounds suitable for use in the present invention, the arsenoxide group (—As═O) can be replaced by an arsenoxide equivalent.

An arsenoxide equivalent any dithiol reactive species that shows essentially the same affinity towards dithiols as —As═O. Typically, arsenoxide equivalent includes dithiol reactive entities, such as As, Ge, Sn and Sb species. More typically an arsenoxide equivalent can be represented by -D($Z_1$)($Z_2$). Arsenoxide equivalents are expected to exhibit identical or substantially identical activity to that of the corresponding arsenoxide.

Typically, for arsenoxide equivalents of the form -D($Z_1$)($Z_2$), D will be, for example, As, RSn, Sb, or RGe, and $Z_1$ and $Z_2$ will be labile groups (i.e. groups easily displaced under physiological conditons), $Z_1$ and $Z_2$, may be identical or different, and may either be connected or independent from each other (bound only to the arsenic atom).

Suitable arsenoxide equivalents include the following:

wherein $Z_1$ and $Z_2$ are selected from the group consisting of OH, $C_1$-$C_{10}$ alkoxy, $C_6$-$C_{10}$ aryloxy, $C_1$-$C_{10}$ alkylthio, $C_6$-$C_{10}$ arylthio, $C_1$-$C_{10}$ alkylseleno, $C_6$-$C_{10}$ arylseleno, F, Cl, Br and I;

$$A\text{---}(XBX')_n B'\text{---}D\begin{smallmatrix}E_1\\ \diagdown\\ \diagup\\ E_2\end{smallmatrix}M$$

wherein $E_1$=$E_2$=O, $E_1$=O and $E_2$=S or $E_1$=$E_2$=S; M is R''' and R'''' are independently selected from the group consisting of hydrogen, $C_1$-$C_{10}$ alkyl, $C_6$-C12 aryl, halogen, $C_1$-$C_{10}$ alkoxy, $C_6$-$C_{10}$ aryloxy, hydroxy and carboxy; and n=1 to 10.

For arsenoxide equivalents of the form $D(Z_1)(Z_2)$, when D is As and $Z_1$ and $Z_2$ are OH, the arsenoxide equivalent may be in equilibrium with polymeric species, as depicted below.

$$A\text{---}(XBX')_n B'\text{---}As\begin{smallmatrix}OH\\OH\end{smallmatrix} \xrightleftharpoons[+H_2O]{-H_2O} \text{linear} \quad \text{or} \quad \text{cyclic}$$

polymeric anhydride

In respect of the equilibrium depicted above, arsenic is one of many elements whose hydroxy species exist in equilibrium with the corresponding polymeric anhydrides. Therefore, arsenoxide compounds may actually exist as low or medium molecular weight polymers (eg n=3 to 6). However, the dehydration reaction is reversible, and therefore soluble polymeric anhydrides are expected to behave as arsenoxide equivalents, that is, they are expected to bind to closely spaced dithiols in substantially the same way as the monomeric ---$As(OH)_2$ species.

$$A\text{---}(XBX')_n B'\text{---}D\begin{smallmatrix}X_3\\ \diagdown\\ \diagup\\ Y_1\end{smallmatrix}\begin{smallmatrix}R'\\ \diagdown\\ \diagup\\ O\end{smallmatrix}$$

wherein $X_3$=NH, $Y_1$=O; $X_3$=$Y_1$=O or $X_3$=S, $Y_1$=O, and R' is selected from the group consisting of hydrogen, $C_1$-$C_{10}$ alkyl, $C_6$-$C_{12}$ aryl, and carboxy, or is one of the twenty amino acid side chains;

$$A\text{---}(XBX')_n B'\text{---}D\begin{smallmatrix}O\\ \diagdown\\ \diagup\\ O\end{smallmatrix}\begin{smallmatrix}O\\ \diagdown\\ \diagup\\ O\end{smallmatrix};$$

-continued $$A\text{---}(XBX')_n B'\text{---}D\begin{smallmatrix}X_3\\ \diagdown\\ \diagup\\ Y_1\end{smallmatrix}\begin{smallmatrix}R_{11}\\R_{12}\\R_{13}\\R_{14}\end{smallmatrix}$$

wherein $X_3$=$Y_1$=O; $X_3$=NH, $Y_1$=O; $X_3$=S, $Y_1$=NH; or $X_3$=S, $Y_1$=NH; or $X_3$=S, $Y_1$=NH and $R_{11}$ to $R_{14}$ are selected from tie group consisting of hydrogen, $C_1$-$C_{10}$ alkyl $C_6$-$C_{12}$ aryl, and $CO_2H$;

$$A\text{---}(XBX')_n B'\text{---}D\begin{smallmatrix}X_3\\ \diagdown\\ \diagup\\ Y_1\end{smallmatrix}\begin{smallmatrix}R_{11}\\R_{12}\\R_{13}\\R_{14}\end{smallmatrix}$$

wherein $X_3$=$Y_1$=O, or $X_3$=NH, $Y_1$=O; and $R_{11}$ to $R_{14}$ are selected from the group consisting of hydrogen, $C_1$-$C_{10}$ alkyl, $C_6$-$C_{12}$ aryl, , halogen, $C_1$-$C_{10}$ alkoxy, and $CO_2H$.

Typically, (XBX')B' is as defined above.

Typically, the method according to the first embodiment of the invention comprises the steps of:
 (a) administering a first component of the system;
 (b) optionally waiting for a period of time; and
 (c) administering a second component of the system.

Typically, the period of time is between about 1 hour and about 48 hours, more typically between about 3 hours and about 36 hours, still more typically between about 6 hours and about 24 hours. Even more typically the period of time is about 18 hours.

Still typically, the method according to the first embodiment of the invention comprises the steps of:
 (a) administering a first component of the system;
 (b) optionally waiting for a period of time;
 (c) administering a second component of said system;
 (d) optionally waiting for a further period of time; and
 (e) administering a further binding member linked to an active agent (or agent capable of becoming an active agent).

Typically, the periods of time are as defined above.

According to a second embodiment of the invention there is provided a system for selectively targeting an active agent (or agent capable of becoming an active agent) to apoptotic cells in a vertebrate, said system comprising a first component comprising an arsenoxide (or arsenoxide equivalent) compound linked to at least one active agent or agent capable of becoming an active agent.

According to a third embodiment of the invention there is provided a system for selectively targeting an active agent (or agent capable of becoming an active agent) to apoptotic cells in a vertebrate, said system comprising a first component comprising an arsenoxide (or arsenoxide equivalent) compound linked to a first binding member; and a second component composing a second binding member, wherein said second binding member is an active agent or an agent capable of becoming an active agent.

According to a fourth embodiment of the invention there is provided a system for selectively targeting an active agent (or agent capable of becoming an active agent) to apoptotic cells in a vertebrate, said system comprising a first component comprising an arsenoxide (or arsenoxide equivalent) compound linked to a first binding member; and a second component comprising a second binding member linked to an active agent (or agent capable of becoming an active agent).

Typically, the second binding member is directly linked to the agent.

Still typically, the second binding member is indirectly linked to the agent. More typically, indirect linking between the agent and the second binding member is by virtue of a further binding interaction between the second binding member and at least one further binding member, wherein the further binding member is directly linked to the agent. Still more typically, the first binding member and the further binding member are different Even more typically, the first binding member and the further binding member are the same.

Typically, with respect to any one of the second to fourth embodiments of the invention, the first component is linked to the agent via a cleavable linker, More typically, with respect to the second embodiment of the invention, the first component is linked to the agent via a cleavable linker.

Typically, with respect to the third or fourth embodiment of the invention, the first and second binding members are as described above in accordance with the first embodiment of the invention. Still typically, with respect to any one of the second to fourth embodiments of the invention, the arsenoxide compound is as described above in accordance with the first embodiment of the invention. Still typically, the active agent is as described above in accordance with the first embodiment of the invention.

According to a fifth embodiment of the invention there is provided a method of treatment and/or prophylaxis of a disease in a vertebrate in need of said treatment and/or prophylaxis, said method comprising administering to said vertebrate a therapeutically effective amount of a system comprising an arsenoxide (or arsenoxide equivalent) compound and a therapeutic agent, wherein said system selectively targets apoptotic cells.

With reference to the fifth embodiment of the invention, typically further therapeutic advantages may be realised through combination regimens. More typically, the method of treatment in accordance with the fifth embodiment of the invention may be applied in conjunction with conventional therapy, such as radiotherapy, chemotherapy or surgery.

According to a sixth embodiment of the invention there is provided the use of a system comprising an arsenoxide (or arsenoxide equivalent) compound and a therapeutic agent for the manufacture of a medicament for the treatment and/or prophylaxis of a disease, wherein said system selectively targets apoptotic cells.

With reference to the fifth and sixth embodiments of the invention, typically, the disease is characterised by an imbalance of apoptosis. More typically, the disease is selected from the group consisting of angiogenesis-dependent diseases, cellular proliferative diseases, inflammatory disorders, auto-immune diseases, blood vessel diseases, thrombosis, cancer, neurodegenerative diseases, myelodysplastic syndromes, ischaemia/reperfusion injury and organ transplant therapy Typically, with respect to the fifth and sixth embodiments of the invention, the system is as described above in accordance with the first embodiment of the invention. More typically, the therapeutic agent is as defined in accordance with the first embodiment of the invention.

According to a seventh embodiment of the invention there is provided a method of detecting and/or imaging apoptotic cells in a vertebrate, said method comprising administering to said vertebrate a biologically effective amount of a system comprising an arsenoxide (or arsenoxide equivalent) compound and a diagnostic agent, wherein said system selectively targets apoptotic cells; and detecting said diagnostic agent.

According to an eighth embodiment of the invention there is provided the use of a system comprising an arsenoxide (or arsenoxide equivalent) compound and a diagnostic agent for the manufacture of a medicament for detecting and/or imaging apoptotic cells, wherein said system selectively targets apoptotic cells.

Typically, with respect to the seventh and eighth embodiments of the invention the, system is as defined in accordance with the first embodiment of the invention. Still typically, the diagnostic agent is as defined in accordance with the first embodiment of the invention.

Typically, the vertebrate is selected from the group consisting of human, nonhuman primate, murine, bovine, ovine, equine, caprine, leporine, avian, feline and canine. More typically, the vertebrate is human, nonhuman primate or murine. Even more typically, the vertebrate is human.

According to a ninth embodiment of the invention there is provided a therapeutic and/or diagnostic kit for selectively targeting an active agent (or agent capable of becoming an active agent) to apoptotic cells in a vertebrate, said kit comprising a first component comprising an arsenoxide (or arsenoxide equivalent) compound linked to a first binding member, and a second component comprising a second binding member, wherein said second binding member is an active agent or agent capable of becoming an active agent, optionally together with a therapeutically and/or diagnostically acceptable carrier and/or diluent.

According to a tenth embodiment of the invention there is provided a therapeutic and/or diagnostic kit for selectively targeting an active agent (or agent capable of becoming an active agent) to apoptotic cells in a vertebrate, said kit comprising a first component comprising an arsenoxide (or arsenoxide equivalent) compound linked to a first binding member; and a second component comprising a second binding member linked to an active agent (or agent capable of becoming an active agent), optionally together with a therapeutically and/or diagnostically acceptable carrier and/or diluent.

According to an eleventh embodiment of me invention there is provided a therapeutic and/or diagnostic kit for selectively targeting an active agent (or agent capable of becoming an active agent) to apoptotic cells in a vertebrate, said kit comprising a first component comprising an arsenoxide (or arsenoxide equivalent) compound linked to a first binding member;

a second component comprising a second binding member; and a third component comprising a third binding member linked to an active agent (or agent capable of becoming an active agent), optionally together with a therapeutically and/or diagnostically acceptable carrier and/or diluent.

Typically, With respect to the ninth to eleventh embodiments of the invention, the components are packaged separately.

Definitions

In the context of this specification, the term "comprising" means "including principally, but not necessarily solely". Furthermore, variations of the word "comprising", such as "comprise" and "comprises", have correspondingly varied meanings.

In the context of this specification, th term "arsenoxide" refers to the group —As=O.

In the context of this specification, the groups written —As=O and —As(OH)$_2$ are to be considered synonymous.

In the context of this specification, the term "arsenoxide equivalent" refers to any dithiol reactive species that shows essentially the same affinity towards dithiols as —As=O or —As(OH)$_2$, and the term includes, for example, groups comprising a transition element and any trivalent arsenical that is either hydrolysed to —As=O or —As(OH)$_2$ when dissolved in an aqueous medium (such as cell culture buffers and the fluids contained in the organism being treated).

The term "arsenical" as used herein, includes any compound that contains arsenic, The term "acyl" as used herein, includes monovalent and divalent alkyl, alkenyl, alkynyl, cycloalkyl and cycloalkenyl moieties possessing a terminal carbonyl substituent wherein attachment may occur at the hydrocarbon moiety, the carbonyl moiety or both, The term "alkyl" as used herein, includes within its meaning monovalent, saturated, straight and branched chain hydrocarbon radicals.

The term "alkenyl" as used herein, includes within its meaning, monovalent straight and branched chain hydrocarbon radicals having at least one double bond.

The term "alkynyl" as used herein, includes within its meaning, monovalent, straight and branched chain hydrocarbon radicals having at least one triple bond.

The term "alkylene" as used herein, includes within its meaning divalent, saturated, straight chain hydrocarbon radicals.

The term "alkenylene" as used herein, includes within its meaning, divalent, straight chain hydrocarbon radicals having at least one double bond.

The term "alkynylene" as used herein, includes within its meaning, divalent, straight chain hydrocarbon radicals having at least one triple bond.

The term "aryl" as used herein, includes within its meaning monovalent, single, polynuclear, conjugated and fused aromatic hydrocarbon radicals.

The term "arylene" as used herein, includes within its meaning divalent, single, polynuclear, conjugated and used aromatic hydrocarbon radicals.

The term "closely spaced dithiol" as used herein, includes within its meaning thiols that are chemically vicinal, as well as thiols brought into spacial apposition by virtue of molecular conformation.

The term "cycloalkyl" as used herein, includes within its meaning monovalent, saturated, monocyclic, bicyclic, polycyclic or fused polycyclic hydrocarbon radicals.

The term "cycloalkylene" as used herein, includes within its meaning divalent, saturated, monocyclic, bicyclic, polycyclic or fused polycyclic hydrocarbon radicals.

The term "cycloalkenyl" as used herein, includes within its meaning monovalent, saturated, monocyclic, bicyclic, polycyclic or fused polycyclic hydrocarbon radicals having at least one double bond.

The term "cycloalkenylene" as/used herein, includes within its meaning divalent, saturated, monocyclic, bicyclic, polycyclic or fused polycyclic hydrocarbon radicals having at least one double bond.

The term "halo" as used herein, includes fluoro, chloro, bromo and iodo.

The term "heteroaryl" as used herein, includes within its meaning monovalent, single, polynuclear, conjugated and fused aromatic radicals having 1 to 12 atoms wherein 1 to 6 atoms are heteroatoms selected from O, N and S.

The term "heteroarylene" as used herein, includes within its meaning divalent, single, polynuclear, conjugated and fused aromatic radicals having 1 to 12 atoms wherein 1 to 6 atoms are heteroatoms selected from O, N and S.

The term "heterocyloalkyl" as used herein, includes within its meaning monovalent, saturated, monocyclic, bicyclic, polycyclic or fused radicals wherein 1 to 5 atoms are heteroatoms selected from O, N or S.

The term "heterocycloalkylene" as used herein, includes within its meaning divalent, saturated, monocyclic, bicyclic, polycyclic or fused polycyclic radicals wherein 1 to 5 atoms are heteroatoms selected from O, N or S.

The term "hetercycloalkenyl" as used herein, includes within its meaning monovalent, saturated, monocyclic, bicyclic, polycyclic or fused polycyclic radicals having at least 1 double bond and wherein 1 to 5 atoms are heteroatoms selected from O, N or S.

The term "heterocycloalkenylene" as used herein, includes within its meaning divalent, saturated, monocyclic, bicyclic, polycyclic or fused polycyclic radicals having at least one double bond and wherein 1 to 5 atoms are heteroatoms selected from O, N or S.

The term "phenylarsonic acid" as used herein, is to be considered synonymous with "benzene arsonic acid".

The term "therapeutically effective amounts" as used herein, includes within its meaning a non-toxic but sufficient amount of a system or component of a system of the invention to provide the desired therapeutic effect. The exact amount required will vary from subject to subject depending on factors such as the species being treated, the age and general condition of the subject the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

HT1080 cells were left untreated (parts a and d) or treated with camptothecin to induce apoptosis (parts b and e), then detached and labelled with annexin V-PE and GSAO-F (parts a and b) or annexin V-PE and GSAA-F (parts b and e). Phycoerythrin fluorescence is plotted against fluorescein fluorescence. The percentage of the total cells that label brightly with annexin V (UL quadrant), GSAO or GSAA (LR quadrant), or both annexin V and GSAO or GSAA (UR quadrant) is shown in parts c (GSAO) and f (GSAA). In part g, HT1080 cells were left untreated (open bars) or treated with camptothecin to induce apoptosis (closed bars), then detached and labelled with GSAO-F, annexin V-PE and propidium iodide. Annexin V-PE fluorescence was plotted against GSAO-F fluorescence for all cells, or all cells excluding those that had taken-up propidium iodide (>200 fluorescence units in FL4). In part h, HT1080 cells were treated with camptothecin in the absence or presence of the broad-spectrum caspase inhibitor Z-VAD-FMK then detached and labelled with GSAO-F. The mean fluorescence of the untreated population was normalised in two experiments and the bars and errors represent the mean and range.

Figure 10:
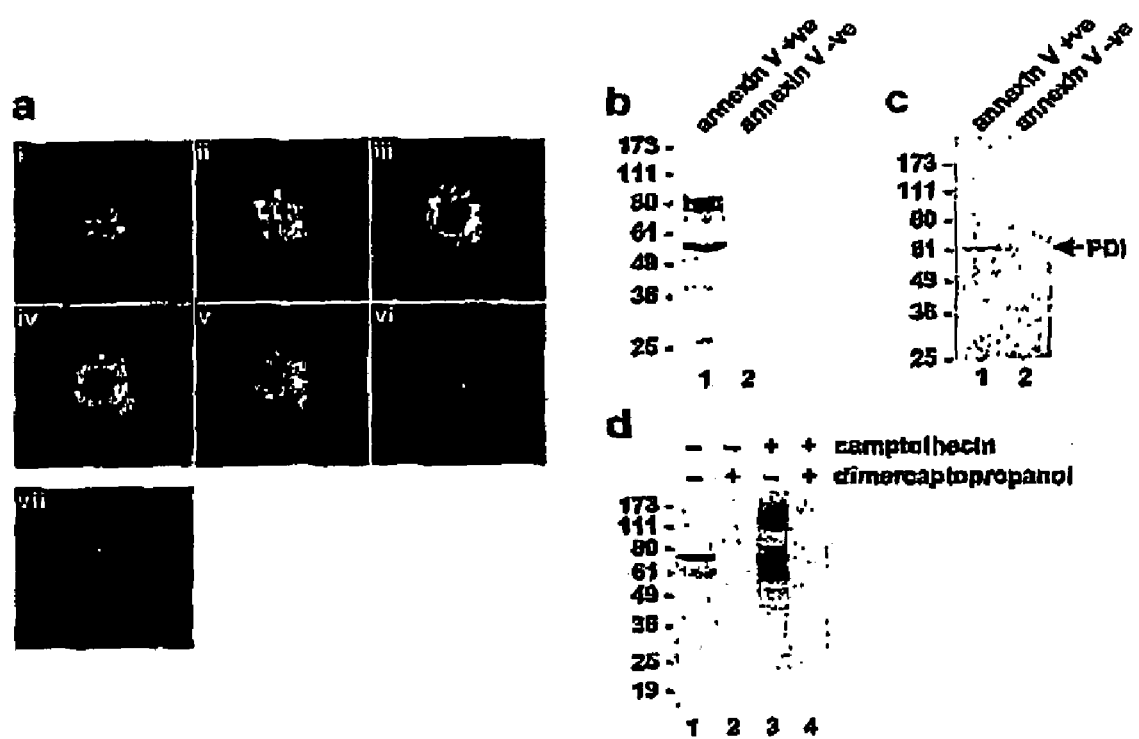

FIG. 10 GSAO entered apoptotic cells and labelled proteins containing closely-spaced dithiols. a HT1080 cells were treated with camptothecin to induce apoptosis, then detached and labelled with GSAO-F and annexin V-Alexa-594. Cells were imaged by confocal micrscopy. Six transverse sections (i to vi) are shown for an annexin V-Alexa-594 labeled cell. Panel vii shows a cell that was not strongly labelled by annexin V-Alexa-594. b HT1080 cells were treated with camptothecin to induce apoptosis, then detached and incubated with annexin V-PE and GSAO-B. Cells were sorted into annexin V-positive (lane 1) and annexin V-negative (lane 2) populations. Equal numbers of cells from each population were lysed, resolved on SDS-PAGE and blotted for GSAO-B with streptavidin-peroxidase. The positions of M$_r$ markers are indicated at left, c GSAO-B labelled proteins from part b were collected an streptavidin-dynabeads, resolved on SDS-PAGE and Western blotted for PDI. d HT1080 cells were untreated (lanes 1 and 2) or treated (lanes 3 and 4) with camptothecin, then detached and incubated with GSAO-B in the absence (lanes 1 and 3) or presence (lanes 2 and 4) of dimercaptopropanol. Equal numbers of cells were lysed, resolved on SDS-PAGE and blotted for GSAO-B with streptavidin-peroxidase.

Figure 11:
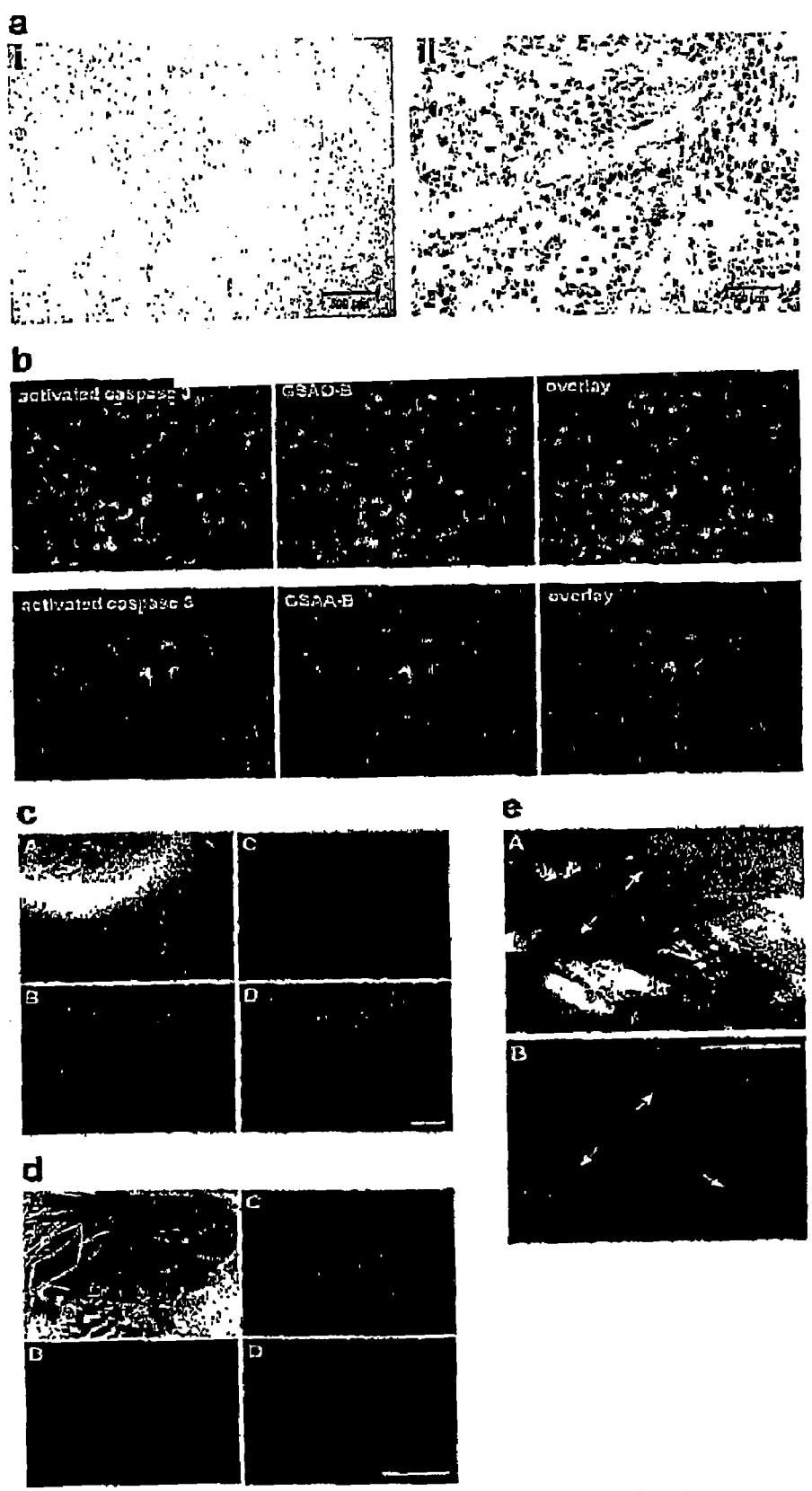

FIG. 11. GSAO labelled apoptotic cells in vivo and can be used to image tumours. a Mice bearing S.C. BxPC-3 tumours in the proximal dorsum were administered GSAO-B or GSAA-B by S.C. injection in the hind flank. The tumours were excised after 6 hours, sectioned and stained for biotin-labelled compound. Low power (i) and high power (ii) miorographs of a sectioned tumour show incorporation of GSAO8 into selected cells (brown). b Tumour sections described in part a were stained for activated caspase-3 (red) and GSAO-B or GSAA-B (green) and counterstained with a nucleic acid stain (blue). Red, green and overlay images are shown. c Fluorescent images of a murine Lewis lung tumour grown S.C. in a C57BL/6 mouse 1 and 24 hours after administration of GSAO-Cy™5.5 Panel A: white light image of the Lewis lung tumour. Panel B: tumour and dorsal skin 1 hour after injection of GSAO-Cy™5.5. Panels C and D: dorsal skin and tumour 24 hours after injection, respectively. d Human BxPC-3 pancreatic tumours grown S. C. in SCID mice 24 hours after administration of GSAO-Cy™5.5, GSAA-Cy™5.5 or Cy™5.5. Panel A: white light image of a BxPC3 tumour. Panels B, C and D: tumours after injection of GSAA-Cy™5.5, GSAO-Cy™5.5 or Cy™5.5, respectively. e Spontaneous prostate tumour in a TRAMP mouse 24 hours after administration of GSAO-Cy™5.5. Panel A: white light image. Panel B:fluorescent image. The arrows indicate the margins of the central vein and tumour. The bars in c, d and e represent 1 mm.

Figure 12:
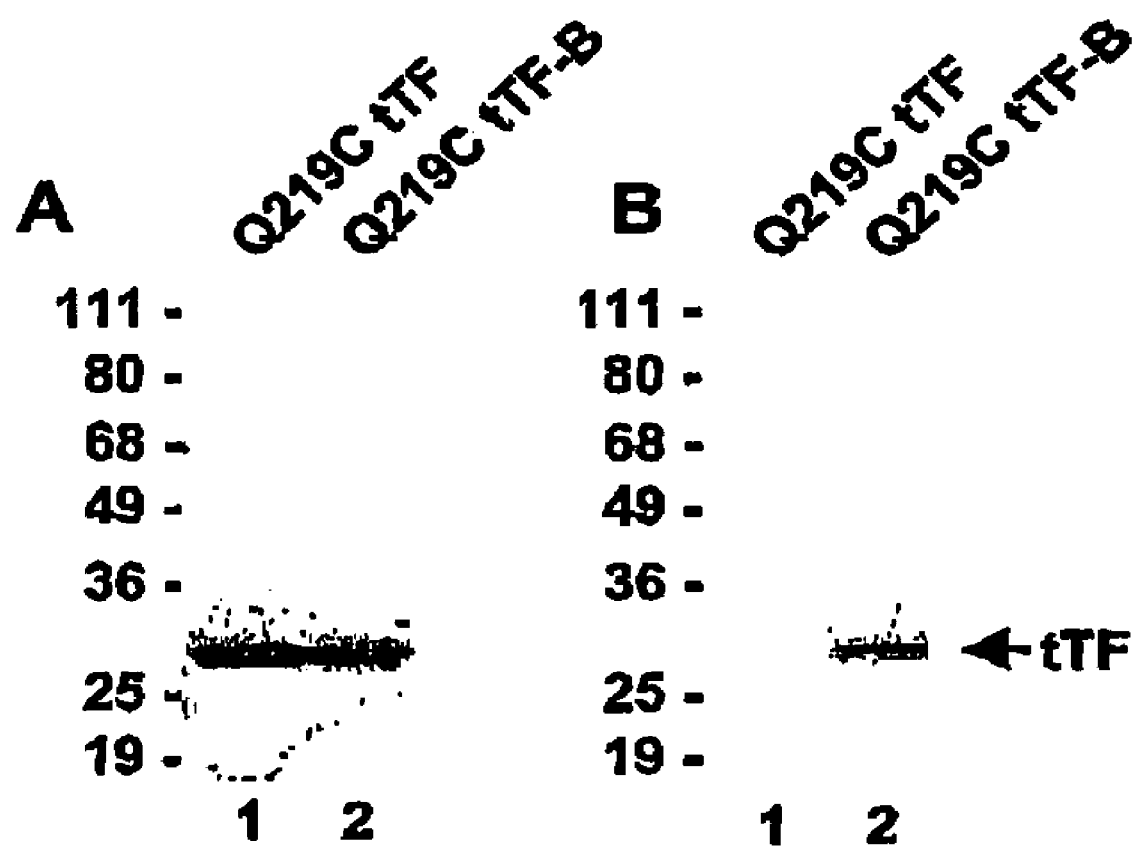

FIG. 12. Labelling of tTF with MPB. A Unlabelled (lane 1) or MPB-labelled (lane 2) Q219C tTF (5 µg) resolved on SDS-PAGE and stained with Coomassie Brilliant Blue. B Unlabelled (lane 1) or MPB-labelled (lane 2) Q219C tTF (50 ng) resolved on SDS-PAGE, transferred to polyvinyldiethylene fluoride and blotted with avidin-peroxidase to detect the biotin label. The positions of $M_r$ markers are indicated at left.

Figure 13:
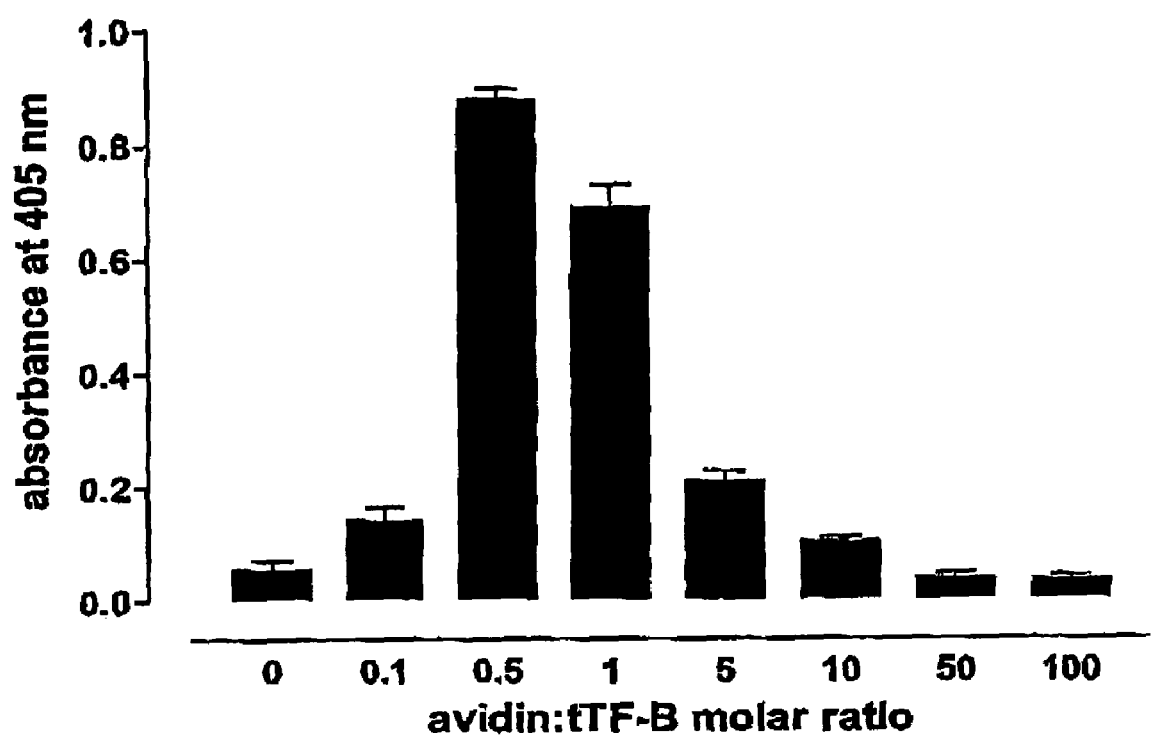

FIG. 13. Formation of the GSAO-B-avidin-tTF-B complex. PDI was immobilised in microlitre wells, labelled with GSAO-B and incubated with tTF-B and increasing molar ratios of avidin. The bound tTF was detected using an anti-TF monoclonal antibody and peroxidase-conjugated secondary antibody. The bars and errors are the mean ±SD of triplicate determinations.

Figure 14:
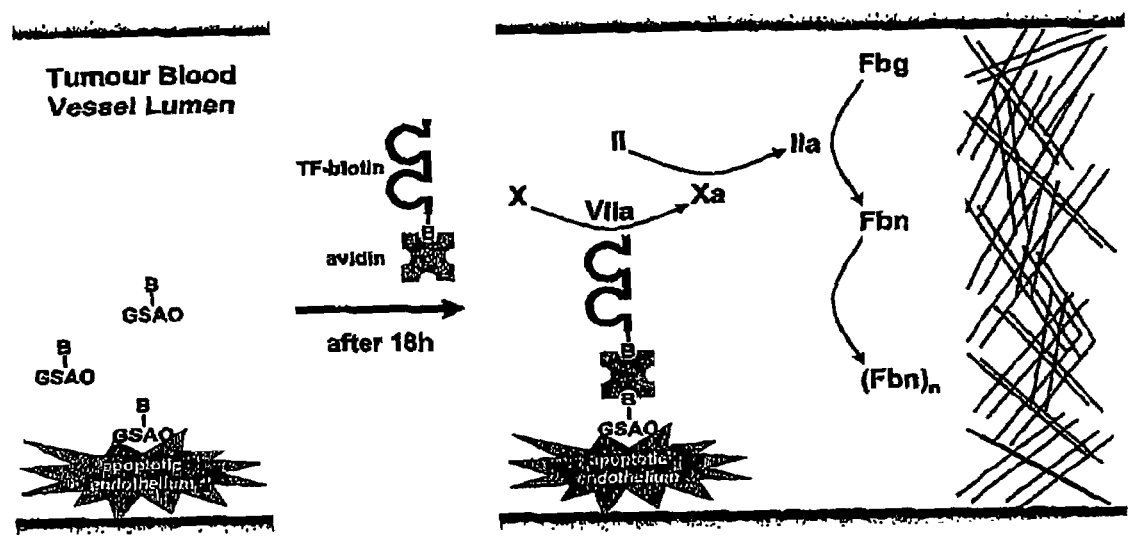

FIG. 14. Carbon of the rationale for use of GSAO-B and avidin-tTF-B to thrombose tumour blood vessels.

Figure 15:
Figure 15:
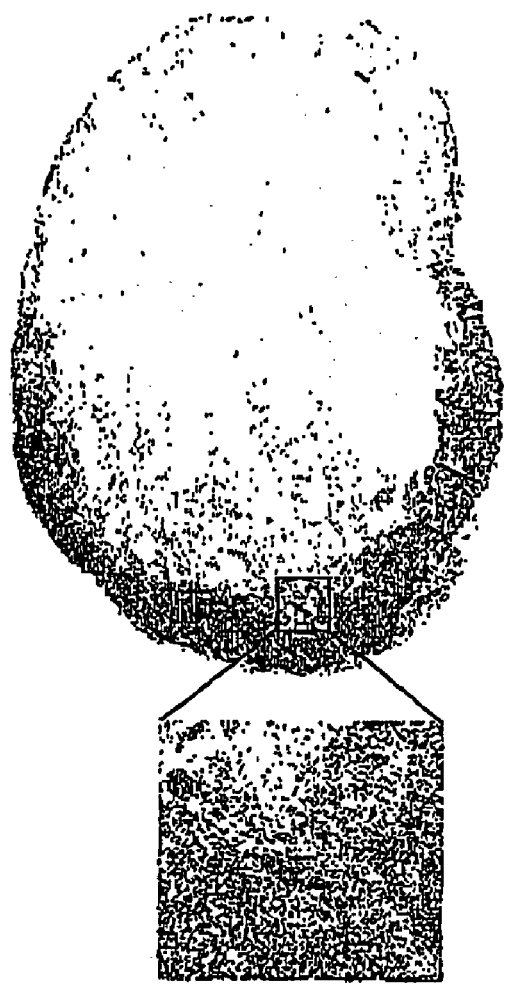

FIG. 15. Thrombosis of tumour vasculature and necrosis of the tumour by S.C. administration of GSAO-B followed by I.V. administration of avidin-tTF-B. A crosssection of an untreated and treated tumour is shown. Extensive necrosis of the centre of the treated tumour is apparent. The inset shows a thrombosed vessel in the treated tumour.

BEST MODE OF PERFORMING THE INVENTION

The present invention relates to the detection of apoptotic cells and uses an arsenoxide (or arsenoxide equivalent) compound to selectively target an active agent, such as a therapeutic or diagnostic agent, to aopototic calls with a relatively high degree of specificity relative to normal cells.

1. Preparation of Compounds 1.1 Synthesis of GSAO

As set out in International (PCT) Patent Application No. PCT/AU00/011434 (WO 01/21628), the disclosure of which is incorporated herein by reference, arsenoxide or arsenoxide equivalent compounds, such as GSAO may be prepared by methods known generally in the art and those skilled in the art would recognise that the various reagents and reactants can be routinely modified in order to synthesise any given compound useful in the invention. A person skilled in the art would also recognise that the invention also provides for the use of compounds in any state of ionisation, for example acid salt, zwitterionic uncharged, zwitterionic anion, dianion.

In a typical synthesis of a preferred arsenoxide compound for use in the invention, glutathione may be reacted with 4-(N-(bromoacetyl)amino)phenylarsenoxide (BRAO) under conditions favourable to the formation of a covalent bond between the free thiol of glutathione and the chemical entity to which the arsenoxide is attached to give GSAO. Reactions involving nucleophilic attack by the glutathione thiol will, in general, require alkaline conditions, Electrophilic attack of some reactive species on the glutathione sulfur atom may be carried out; in general this would likely require acidic conditions. A synthesis of GSAO is provided in example 1(a) and represented schematically in FIG. 1.

1.2 Synthesis of GSAO-B

A method of synthesis of GSAO-B, below, is provided in Example 1(c) and illustrated in FIG. 4.

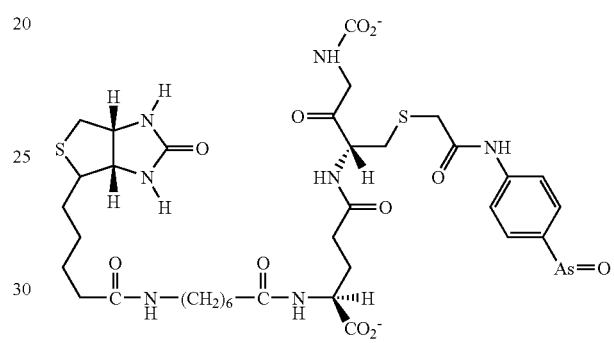

wherein n=1 or 2.

1.3 Synthesis of GSAO-F

Figure 5:
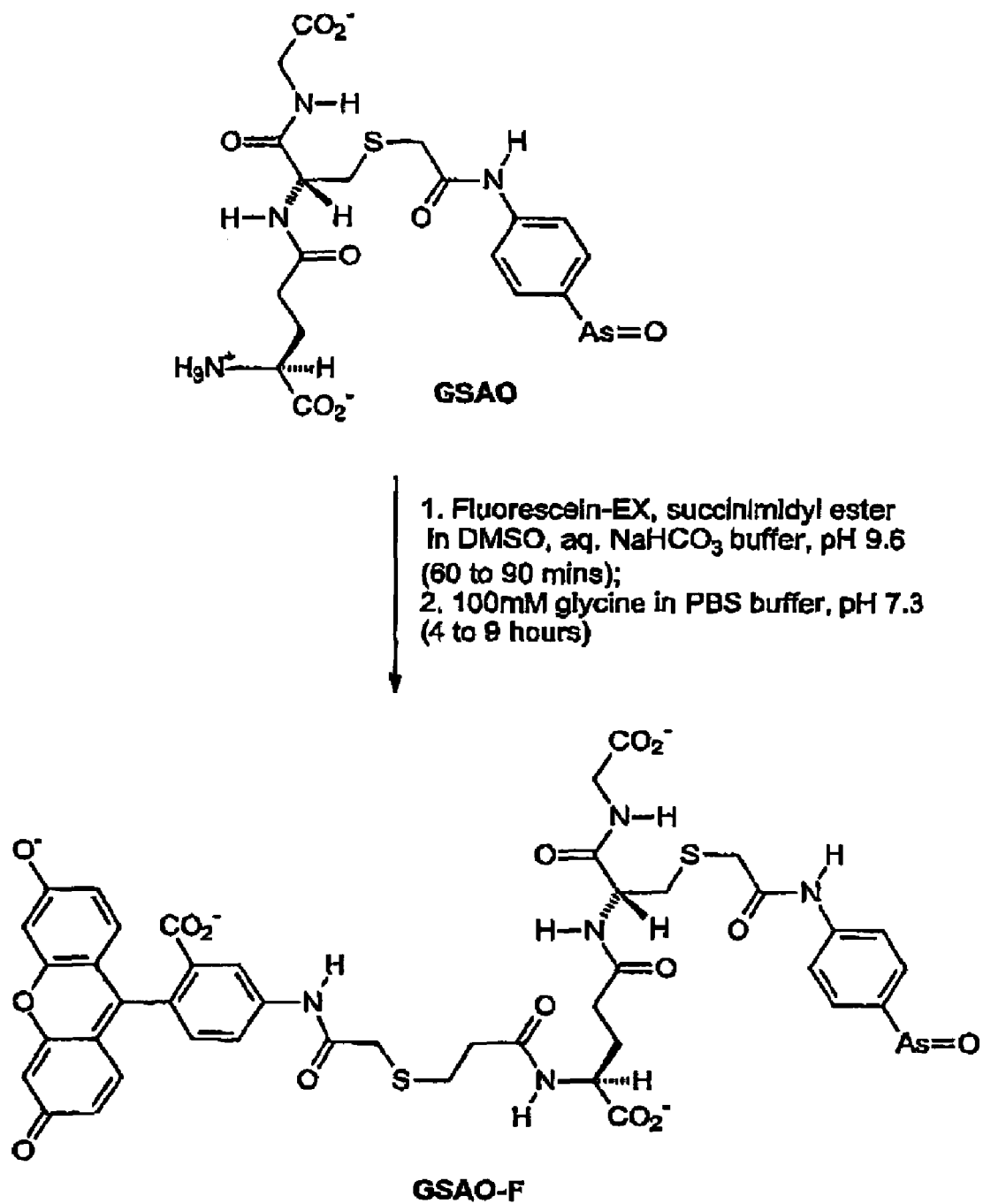
FIG. 5: Schematic representation of the synthesis of GSAO-F.

A method of synthesis of GSAO-F, is provided in Example 1(d) and illustrated in FIG. 5,

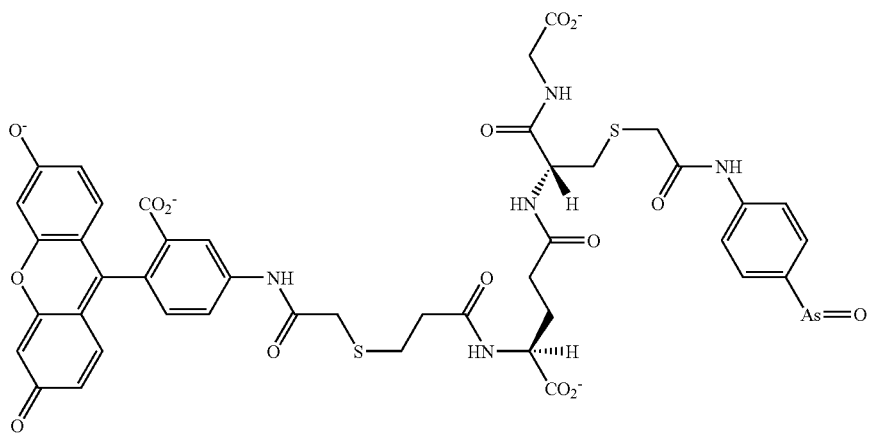

1.4 Synthesis of GSAO-Cy™5.5

Figure 6:
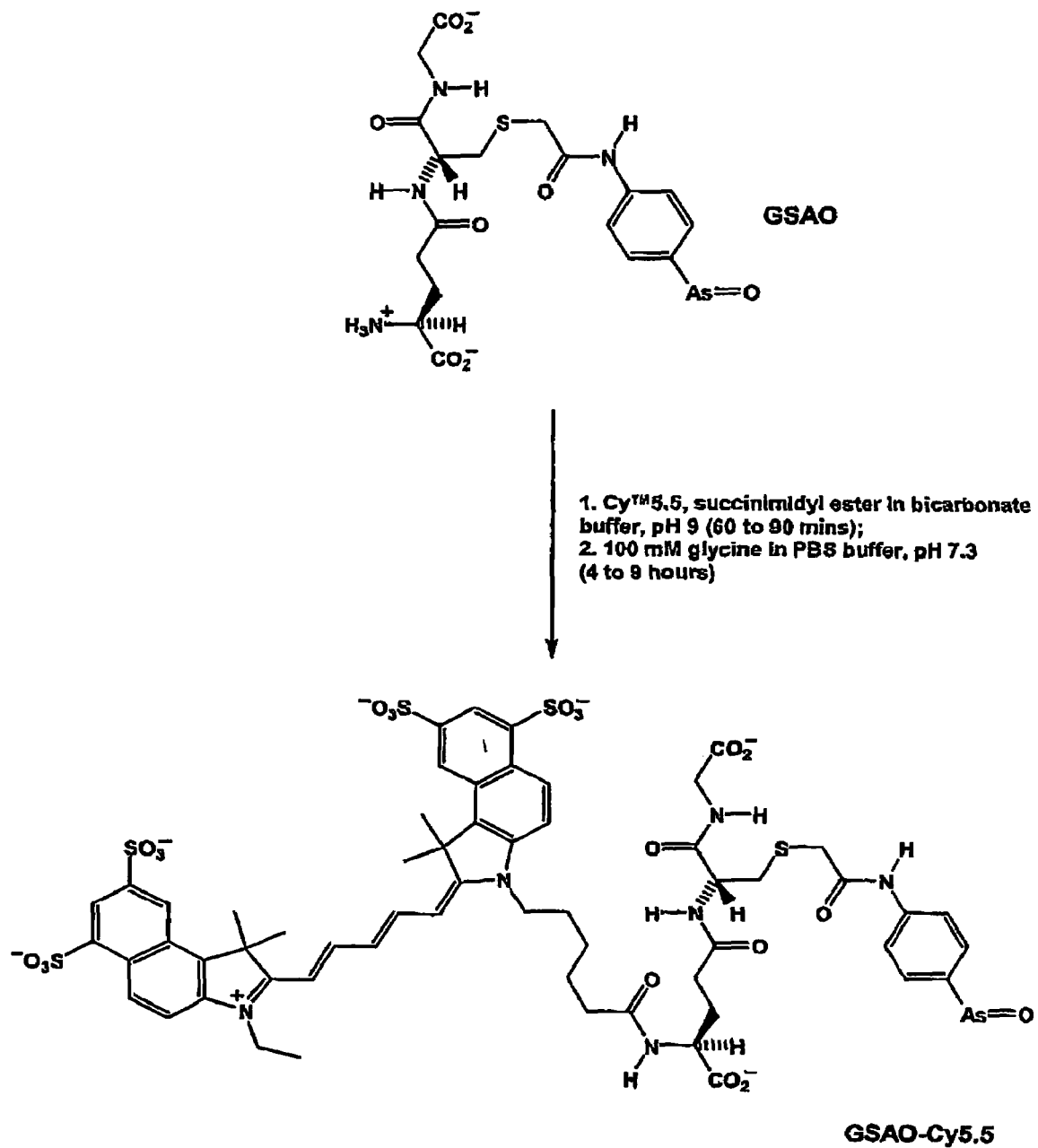
FIG. 6: Schematic representation of the synthesis of GSAO-Cy™5.5

A method of synthesis of GSAO-Cy™5.5, below, is provided in Example 1(e) and illustrated in FIG. 6.

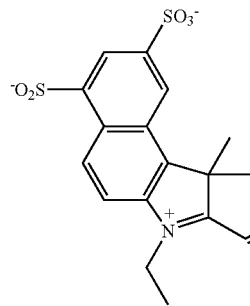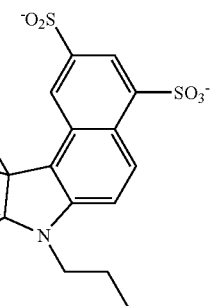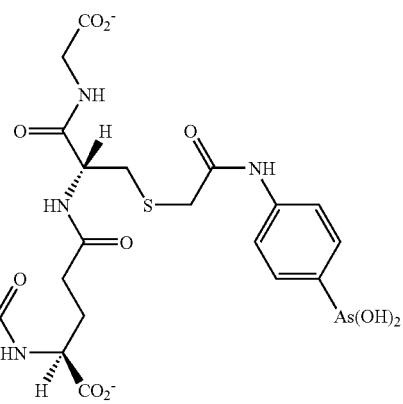

2. Systems for Targeting Active Agents to Apoptotic Cells and/or Dead Cells

The present invention utilises systems comprising an arsenoxide (or arsenoxide equivalent) compound to selectively target an active agent to apoptotic cells. GSAO targets both apoptotic and dead cells. As outlined in Example 3(d), at least seven proteins incorporated GSAO in apoptotic cells. Further, GSAO bound selectively to apoptoatc tumour cells in vivo. As disclosed herein, this binding has been used to image tumours in mice With a near-infrared fluorescent-labelled GSAO.

Exemplary systems suitable for use in the present invention are shown schematically below.

2.1 System 1:

One system suitable for use in the present invention comprises an arsenoxide (or arsenoxide equivalent) compound which is directly linked to at least one active agent, or agent capable of becoming an active agent. Typically, the active agent is a therapeutic agent such as 5-fluorouracil, adriamycin and vincristine, or a detectable agent such as fluorophores, including fluorescein Cy™5.5, and 8-aminonaphthalene 1,3,6-trisulfonate (ANTS).

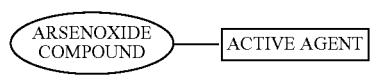

In accordance with this system, the linker may be cleavable such that the active agent is "released" in situ at the target site as illustrated below.

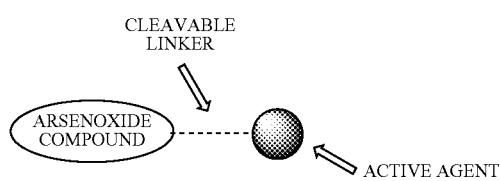

Cleavable linkers are well known to those skilled in the art and include, for example, enzymatically cleavable linkages such as peptides, esterase labile linkers, and the like.

Figure 9:
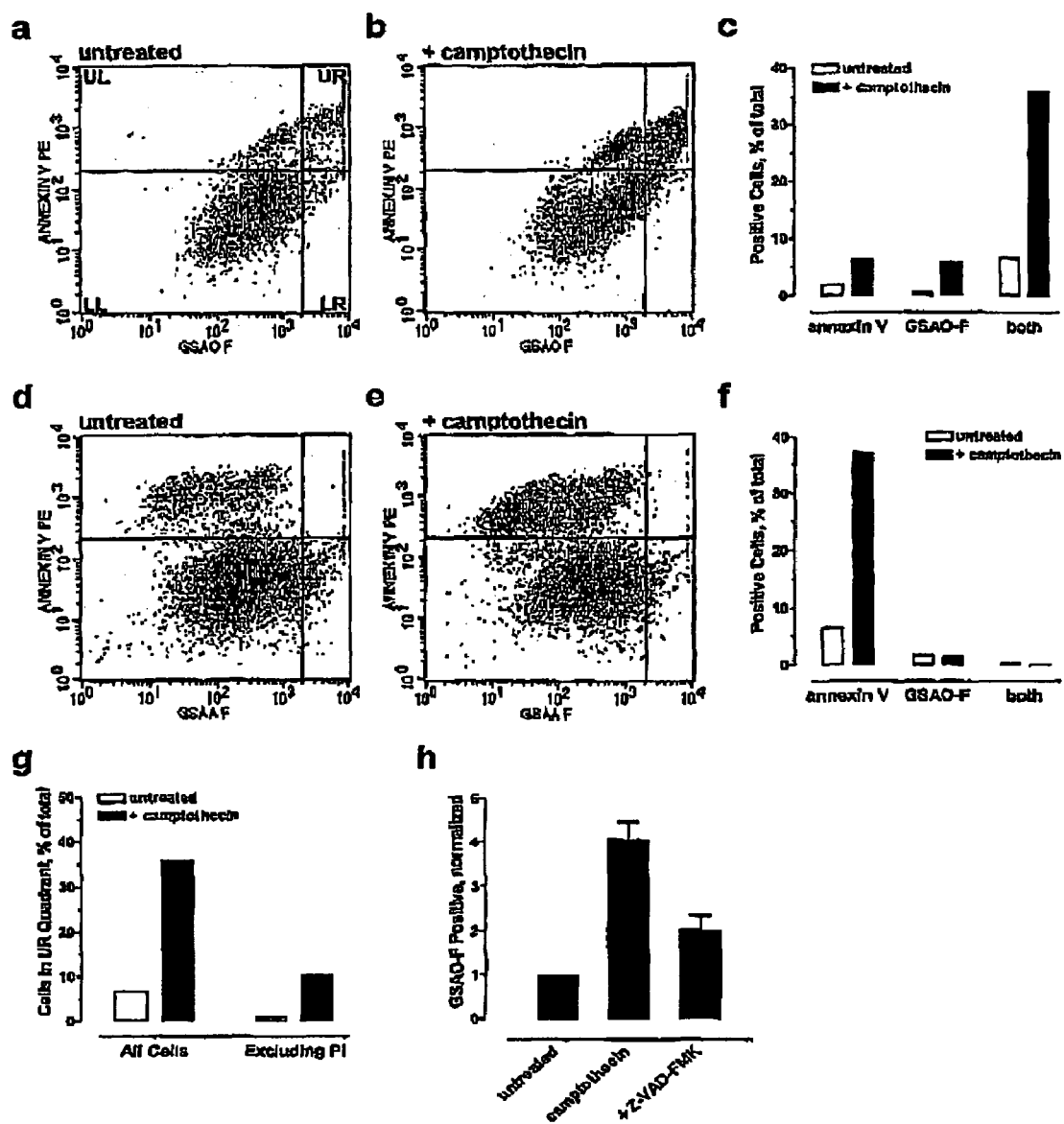
FIG. 9. GSAO labelled apoptotic cells following a caspase activation.

Examples of a system useful for detecting and/or imaging apoptotic cells are GSAO-F (FIG. 5) and GSAO-Cy™5.5 (FIG. 6), in which the arsenoxide compound GSAO is covalently linked to the fluorophores fluorescein and Cy™5.5 respectively. The GSAO moiety selectively targets apoptotic cells, and thereby selectively delivers the fluorophore to apoptotic cells (FIGS. 9-11).

By way of further example, GSAO-Cy™5.5 can be used for detecting apoptotic cells in vivo. In accordance with the method of the invention, GSAO-Cy™5.5 is administered to a subject. The mode of administration will vary according to the site to be detected. Typically, the mode of administration is parenteral, intravenous, subcutaneous, or oral. After administration, a period of time is allowed to pass in order for residual GSAO-Cy™5.5 to be cleared from general circulation, Typically, the period of time is between about 1 and about 48 hours, more typically between about 3 hours and about 36 hours, still more typically between about 6 hours and about 24 hours. Even more typically, the period of time is about 18 hours. Detection of the Cy™5.5 fluorophore can be achieved using general techniques well known in the art and enables the location of apoptotic cells to be determined (FIG. 11).

When the system incorporates an imaging agent, such as a fluorescent agent or an MRI agent (e.g. a paramagnetic lanthanide ion complex of DOTA (1,4,7,10-tetraazacyclododecane tetraacetic acid), or DTPA (diethylenetriaminepentaacetic acid)), the imaging agent is selectively targeted to sites of apoptotic cells. Standard methods of detection of the imaging agent will then enable those sites to be readily identified.

Gd(III) is one example of a lanthanide ion which has been shown to be very effective as a contrast-enhancing agent in magnetic resonance imaging (MRI). The following schemes depict the synthesis of a system comprising an arsenoxide compound (represented by GSAO) which is directly linked to a lanthanide ion complex, represented by Gd(III) DOTA and Gd(III) DPTA, suitable for use in the present invention.

2.1.1 Detectable Systems Comprising Lanthanide Ions
(a) Synthesis of GSAO-[Gd(III) DOTA]
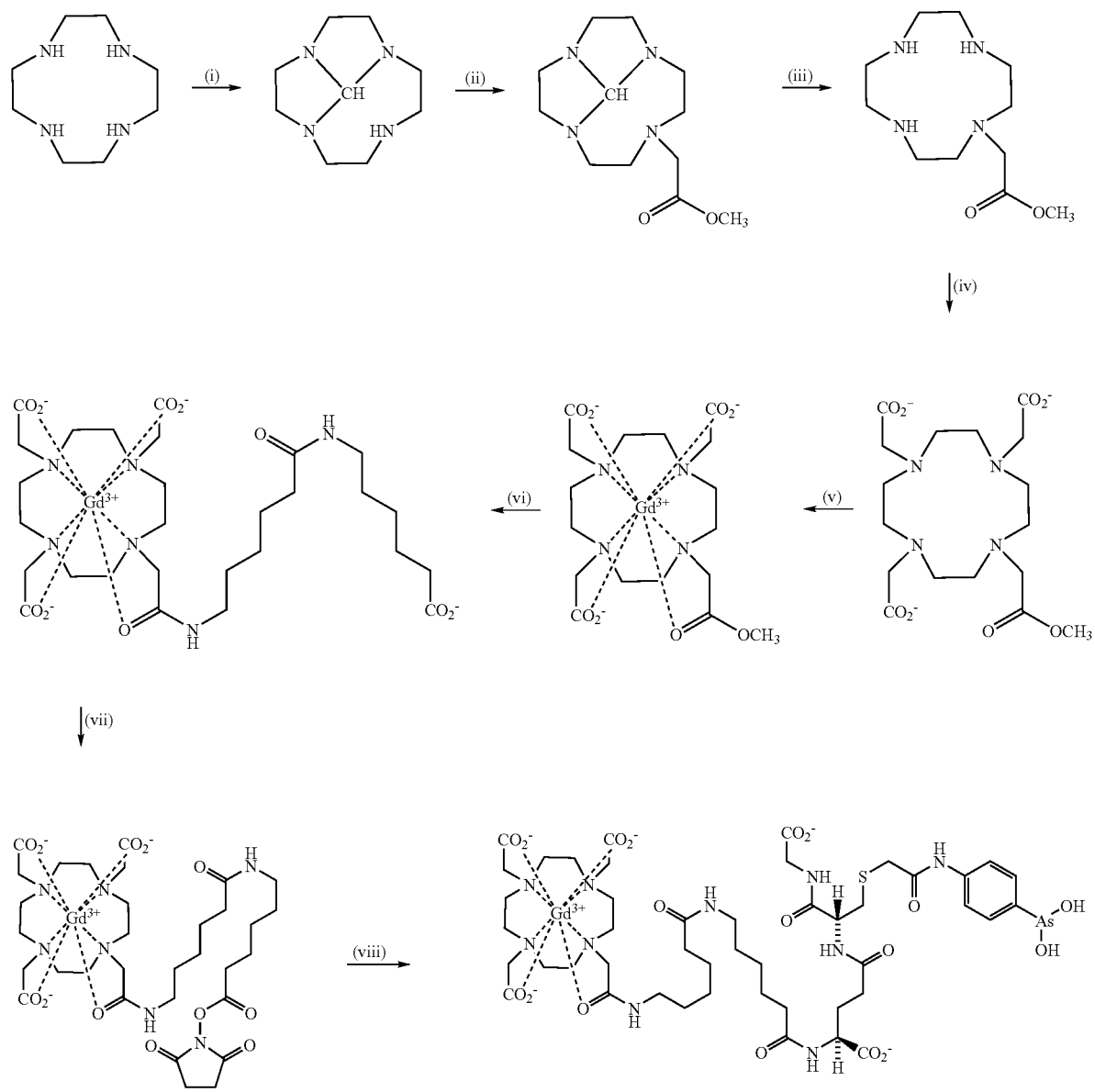
GSAO-[Gd-DOTA]
(i) $(CH_3)_2NCH(OCH_3)_2$, toluene, 120° C.
(ii) methyl bromoacetate in $CH_2Cl_2$, $Na_2CO_3$ in water,
(iii) water, ethanol.
(iv) bromoacetic acid, $Na_2CO_3$ in water,
(v) $GdCl_3 \cdot 6H_2O$ in water,
(vi) XX-Linker, catalytic NHS, catalytic $H_2SO_4$,
(vii) NHS, DCC in acetone,
(viii) GSAO, $NaHCO_3$ in water.

(b) Synthesis of GSAO-[Gd(III) DTPA]

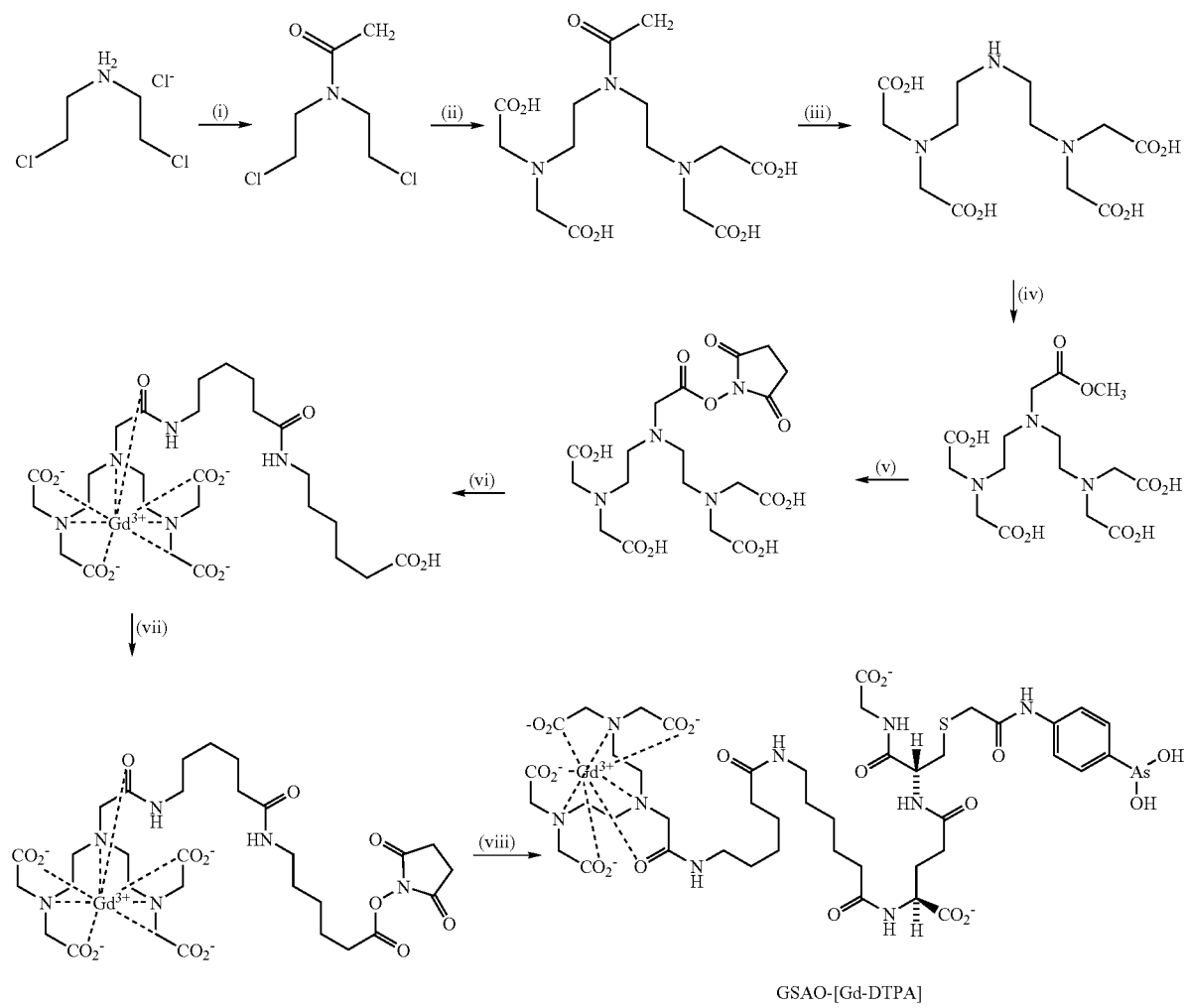

(i) acetic anhydride, sodium acetate, acetic acid.
(ii) iminodiacetic acid, Na$_2$CO$_3$ in water; sulphuric acid.
(iii) catalytic sulfuric acid, water.
(iv) methyl bromoacetate in CH$_2$Cl$_2$, Na$_2$CO$_3$ in water; sulfuric acid.
(v) NHS, catalytic H$_2$SO$_4$.
(vi) XX-Linker, NaHCO$_3$ in water; GdCl$_3$·6H$_2$O in water.
(vii) NHS, DCC, acetone, (viii) GSAO, NaHCO$_3$ in water.

The linking group been the GSAO moiety and the DOTA or DTPA complex exemplified in the above schemes ran be readily prepared by those skilled in the art using known chemical reactions. One example of a synthetic route is depicted below.

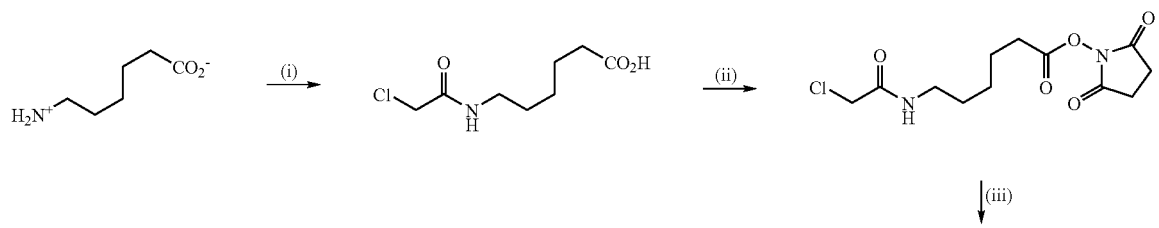

-continued

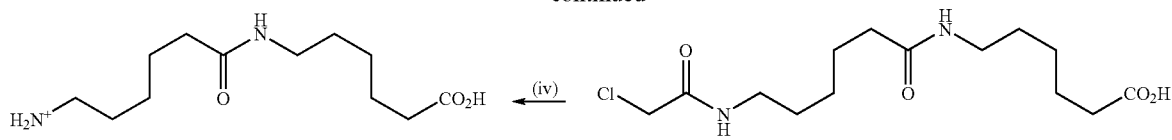

(i) chloroacetic anhydride, Na₂CO₃ in water; sulfuric acid.
(ii) NHS, DCC, acetone.
(iii) e-amino-n-caproic acid, NaHCO₃ in water; sulfuric acid
(iv) thiourea, ethanol; water.

An alternative approach to the preparation of arsenoxide-[anthanide complex] conjugates utilises the functionalised DOTA and DTPA ligands such as the isothiocyanate derivatives shown below:

CHX-A''

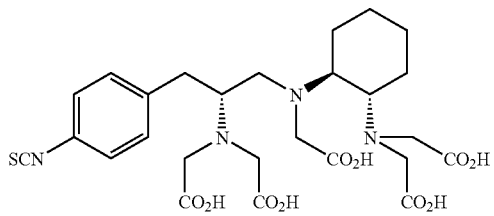

IB4M

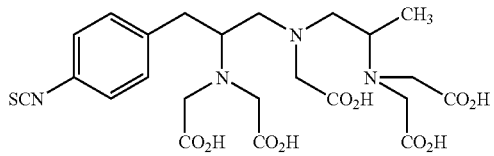

C-DOTA

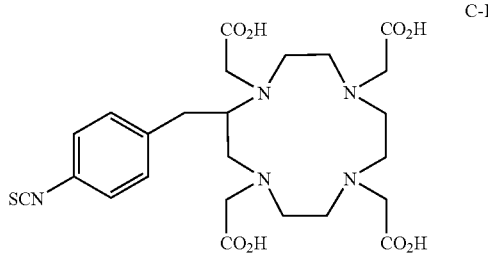

The above ligands have all been well defined for their stability with Gd(III), Y(III) and other lanthanide ions. An example of a synthetic route to arsenoxide conjugates of the above ligands is depicted in the scheme below using the CHX-A'' ligand. The arsenoxide moiety is exemplified by GSAO.

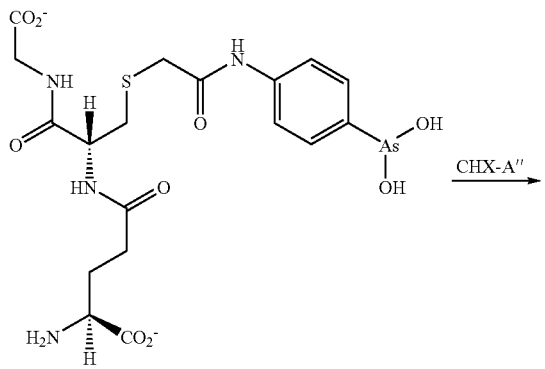

CHX-A'' →

-continued

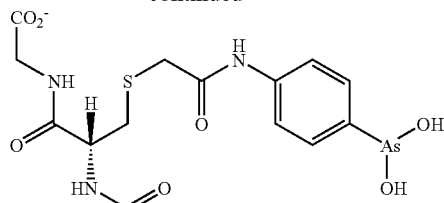

Gd(NO₃)₈ →

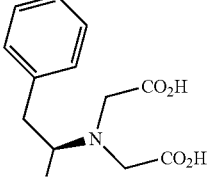

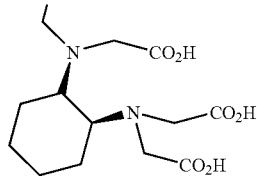

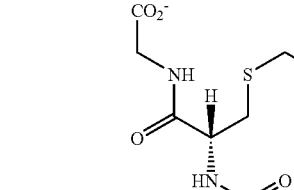

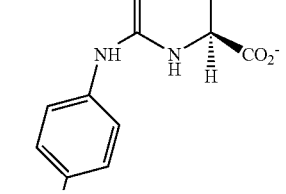

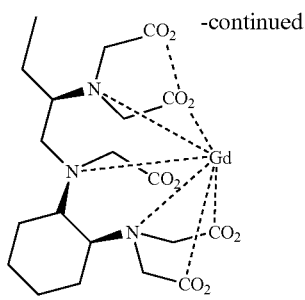

2.1.3 Detectable and/or Therapeutic Systems Comprising Radionucleotides

Radioisotopes are useful as both imaging and therapeutic agents. A synthetic route to systems suitable for use in the present invention in which an arsenoxide moiety (exemplified by GSAO) is linked to a radiolabelled moiety is shown below.

The scheme shown above utilises iodine-123, however a person skilled in the art would readily comprehend that the above synthesis is general and also applies to other active agents and radioisotopes. For instance, substitution of sodium [$^{123}I$]iodide with sodium[$^{125}I$]iodide or [$^{131}I$]iodide would give a system comprising the corresponding, radio-iodine radionucleotide. As illustrated below, a $^{18}F$ fluorinated system can be readily prepared in a similar manner to the above synthesis.

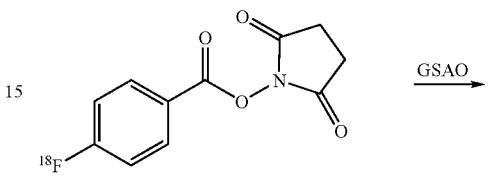

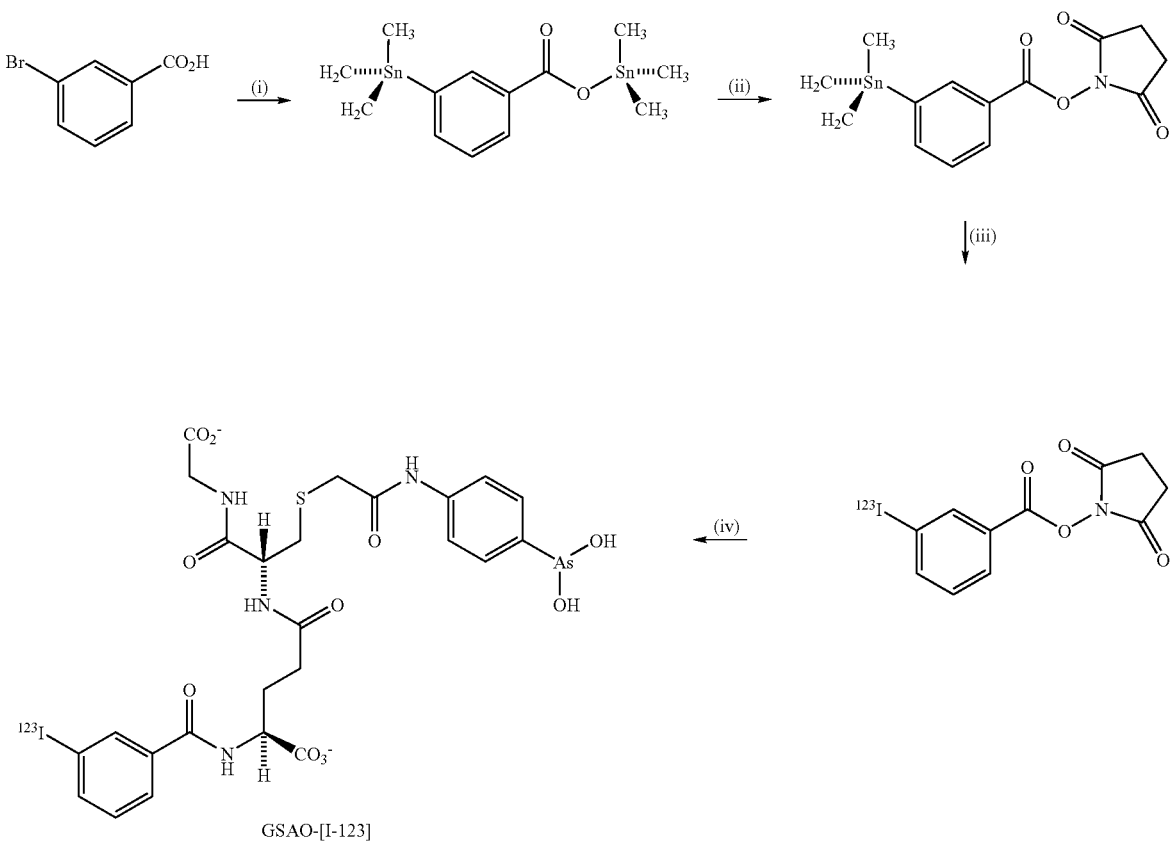

(i) butyllithium, trimethyltin chloride,
(ii) NHS,
(iii) sodium [$^{123}I$]Iodide, $H_2O_2$,
(iv) GSAO, aq. $NaHCO_3$.

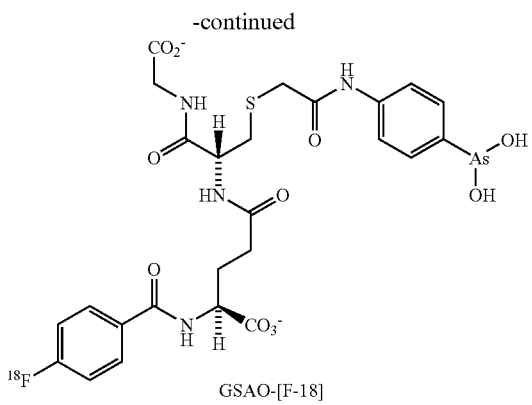

GSAO-[F-18]

$^{18}F$ is a known positron emitter and is used in positron emission tomography (PET) as an imaging agent. Other radioisotopes suitable for use in PET systems are well known in the art, e.g. $^{86}Y$ and $^{99}Tc$. Accordingly, a further system of the invention in which the active agent directly linked to an arsenoxide moiety is a PET agent, is the technetium-99 labelled system prepared according to the scheme below.

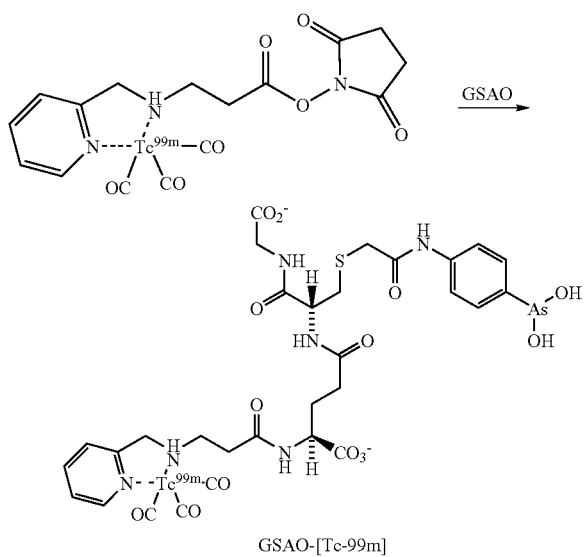

GSAO-[Tc-99m]

In addition to use in MRI, arsenoxide conjugates of the ligands CHX-A", 1B4M or C-DOTA (above) may also be radiolabelled, for example, with $^{111}In$ for use in γ-scintigraphy, or with $^{64}Cu$, $^{18}F$, $^{88}Y$ or $^{99}Tc$ for use in PET imaging. Other radioisotopes useful for therapeutic purposes within the scope of the present invention include rhenium-188, copper-64, indium-111, lutetium-177, and yttrium-90, bismuth-213. Other radioisotopes are well known to those skilled in the art. The suitability of a radioisotope for therapeutic applications can be readily identified based on targeting kinetics and results from biodistribution studies.

2.2 System II:

Another system suitable for use in the present invention, illustrated schematically below, comprises (i) a first component comprising an arsenoxide (or arsenoxide equivalent) compound which is linked to a first binding member; and (ii) a second component, comprising a second binding member, wherein the second binding member is an active agent, or an agent capable of becoming an active agent.

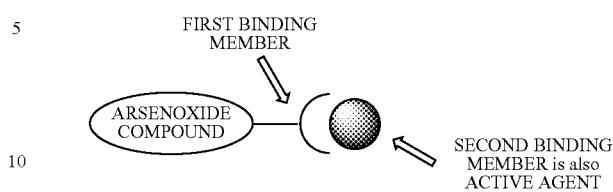

The arsenoxide (or arsenoxide equivalent) moiety, such as GSAO, selectively targets apoptotic cells thereby delivering the first binding member to apoptotic cells. The first binding member is capable of interacting with a second binding member. For example, a first binding member is an enzyme and the second binding member is a substrate for the enzyme. The enzyme substrate may be a prodrug which is converted to an active drug by the enzyme at the site of apoptotic cells. In particular, this system can utilise the 'bystander effect' whereby the active drug can diffuse to nearby cells in the environ of the apoptotic cell(s) targeted by the above system.

In accordance with the method of the present invention, the first component of this system could be administrated to a subject, followed by a period of time to allow any of the component not taken up by apoptotic cells to be cleared from general circulation. The second component, viz, the second binding member can then be administered to the subject. The mode of administration is typically parenteral, subcutaneous, intravenous or oral. The second binding member will interact with the first binding member which is selectively located at apoptotic cells, thereby enabling the therapeutic or detectable agent to be isolated in the apoptotic cell environment.

2.3 System III:

A further system suitable for use in the present invention, illustrated schematically below, comprises (i) a first component comprising an arsenoxide (or arsenoxide equivalent) compound which is linked to a first binding member; and (ii) a second component comprising a second binding member linked to at least one active agent.

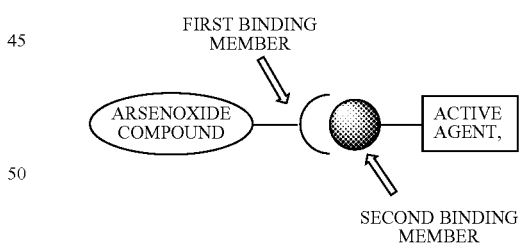

According to this system, an arsenoxide moiety (such as GSAO) is linked to a first binding member (such as biotin) ie, an example of a first component of this system is GSAO-B. When administered to a subject, the arsenoxide moiety selectively targets GSAO-B to apoptotic cells. The second component comprises a second binding member which is capable of interacting with the first binding member. The second binding member may be linked to an active agent such as a therapeutic agent (e.g. a chemotherapeutic drug) or a diagnostic agent (e.g, a fluorophore). The second binding member may be linked to a vehicle for the active agent, such as a liposome, and the active agent may reside within the vehicle, ie, within the liposome. When the second component is administered to the subject, it selectively binds to the first component at the site of apoptotic cells. In the case of GSAO-B where the first binding member is biotin, a suitable second binding member is avidin or streptavidin.

Typically, after the first component of the system is administered to a subject this is followed by a period of time to enable any of the residual first component not taken up by apoptotic cells to be cleared from circulation. The second component is then administered.

In one example in accordance with this system, the first component can comprise GSAO-B and the second component can comprise avidin linked to a liposome which encapsulates an active agent such as a chemotherapeutic drug, e.g. deoxyrubicin. Typically, the liposome will be coated with avidin. This system allows high concentrations of an active agent (such as deoxyrubicin) to be selectively targeted to apoptotic cells relative to normal cells.

A further example of this system for use in the present invention is provided by Examples 3(d) and 3(e). In example 3(d), cells were treated with the first component GSAO-B, in vitro, and residual GSAO-B cleared by washing. The second component, comprising avidin-peroidase was then added. A known method of detection allowed apoptotic cells to be identified.

2.4 System IV:

Another system suitable for use in the present invention is represented schematically below.

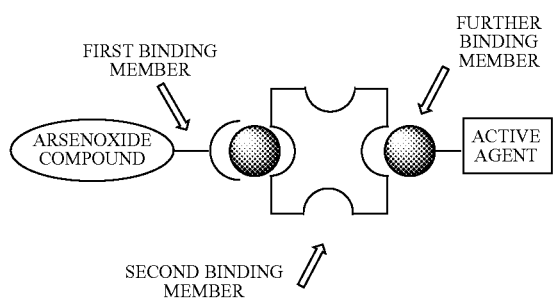

An example of this system used in accordance with the method of the invention is provided in Example 5(c). As disclosed herein, the property of GSAO targeting apoptotic tumour cells has been used to deliver a clotting agent to tumour blood vessels. Tissue Factor (TF) is the major initiating receptor for the blood coagulation cascade. Binding of factor VII/VIIa to TF activates the serine protelnase zymogens factors IX and X by limited proteolysis leading to the formation of thrombin and ultimately a blood clot. The extracellular domain of TF (tTF) is a soluble protein with a factor X-activating activity that is about five orders of magnitude less than that of native transmembrane TF in an appropriate phospholipid membrane environment. This is because the TF:VIIa complex binds and activates factors IX and X far more efficiently when associated with a negatively charged surface.

When administered to a vertebrate having, for example, a tumour, the arsenoxide compound delivers Tissue Factor almost exclusively to the site of increased apoptosis, that is, the tumour site(s). Once localised at the tumour site, the presence of Tissue Factor can initiate the thrombin cascade to induce site-specific blood clotting, thereby obstructing bloodflow to the tumour and causing severe necrosis of tumour tissue.

3. Pharmaceutical and/or Therapeutic Formulations

Further, components of the systems of the invention often involve the active agents outlined above present in the form of pharmaceutical and/or therapeutic formulations, that is, active agents present together with a pharmaceutically acceptable carrier, adjuvant and/or diluent.

For medical use, salts of the active agents may be used in the systems of the invention and they include pharmaceutically acceptable salts, although other salts may be used in the preparation of the compound or of the pharmaceutically acceptable salt thereof. By pharmaceutically acceptable salt it is meant those salts which, within the scope of sound medical judgement, are suitable for use in contact with the tissues of humans and lower animals without undue toxicity, irritation, allergic response and the like, and are commensurate with a reasonable benefit/risk ratio. Pharmaceutically acceptable salts are well known in the art.

For instance, suitable pharmaceutically acceptable salts of the compounds useful in the systems of the invention may be prepared by mixing a pharmaceutically acceptable acid such as hydrochloric acid, sulfuric acid, methanesulfonic acid, succinic acid, fumaric acid, maleic acid, benzoic acid, phosphoric acid, acetic acid, oxalic acid, carbonic acid, tartaric acid, or citric acid with the compounds of the invention. Suitable pharmaceutically acceptable salts of the compounds useful in the systems of the invention therefore include acid addition salts.

For example, S. M. Berge et al. describe pharmaceutically acceptable salts in detail in *J. Pharmaceutical Sciences*, 1977, 66:1-19. The salts can be prepared in situ during the final isolation and purification of the compounds used in the systems of the invention, or separately by reacting the free base function with a suitable organic acid. Representative acid addition salts include acetate, adipate, alginate, ascorbate, asparate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylproplonate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

Also included within the scope of compounds useful in the systems of the present invention are prodrugs. Typically, prodrugs will be functional derivatives of the compounds used in the present invention which are readily converted in vivo to the required (active) compounds as used in the systems of the invention as active agents, such as therapeutic and/or diagnostic agents. Typical procedures for the selection and preparation of prodrugs are known to those of skill in the art and are described, for instance, in H. Bundgaard (Ed), *Design of Prodrugs*, Elsevier, 1985.

Single or multiple administrations of the compounds or pharmaceutical compositions can be carried out with dose levels and pattern being selected by the treating physician. Regardless, the compounds or pharmaceutical compositions useful in systems of the present invention should provide a quantity of the compound sufficient to effectively treat the patient.

One skilled in the art would be able, by routine experimentation, to determine an effective, non-toxic amount of the compounds or pharmaceutical compositions used in the invention which would be required to detect apoptotic cells and/or treat or prevent the disorders and diseases. Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 Mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

In relation to GSAO, an effective dosage is in the range of about 0.0001 mg to about 100 mg GSAO per kg body weight per 24 hours, preferably about 0.001 mg to about 100 mg GSAO per kg body weight per 24 hours, more preferably about 0.01 mg to about 50 mg GSAO per kg body weight per 24 hours, even more preferably about 0.1 mg to about 20 mg GSAO per kg body weight per 24 hours, even more preferably still about 0.1 mg to about 10 mg GSAO per 1 body weight per 24 hours.

In relation to an active agent for use in systems of the present invention, an effective dosage is in the range of about 0.0001 mg to about 100 mg agent per kg body weight per 24 hours, preferably about 0.001 mg to about 100 mg agent per kg body weight per 24 hours, more preferably about 0.01 mg to about 50 mg agent per kg body weight per 24 hours, even more preferably about 0.1 mg to about 20 mg agent per kg body weight per 24 hours, even more preferably still about 0.1 mg to about 10 mg agent per kg body weight per 24 hours.

Typically the treatment would be for the duration of the condition.

Further, it will be apparent to one of ordinary skill in the art that the optimal quantity and a spacing of individual dosages of a compound used in a system of the present invention will be determined by the nature and extent of the condition being treated, the form, route and site of administration, and the nature of the particular vertebrate being treated. Also, such optimum conditions can be determined by conventional techniques.

It will also be apparent to one of ordinary skill in the art that the optimal course of treatment, such as, the number of doses of the compound within the systems of the present invention given per day for a defined number of days, can be ascertained by those skilled in the art using conventional course of treatment determination tests.

Whilst the compounds used in the systems of the present invention may be administered alone, it is generally preferable that the compound be administered as a pharmaceutical composition/formulation. In general pharmaceutical formulations representing the component(s) of the systems of the present invention may be prepared according to methods which are known to those of ordinary skill in the art and accordingly may include a pharmaceutically acceptable carrier, diluent and/or adjuvant.

The carriers, diluents and adjuvants must be "acceptable" in terms of being compatible with the other ingredients of the formulation, and not deleterious to the recipient thereof.

Examples of pharmaceutically and veterinarily acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

In a preferred form the pharmaceutical composition of a compound suitable for use in the invention comprises an effective amount of an active agent, together with a pharmaceutically acceptable canter, diluent and/or adjuvant as shown in Example 6.

The pharmaceutical compositions representing a component of the system of the invention may be administered by standard routes. In general, the compositions may be administered by the topical, transdermal, intraperitoneal, intracranial, intracerebroventricular, intracerebral, intravaginal, intrauterine, oral, rectal or parenteral (e.g., intravenous, intraspinal, subcutaneous or intramuscular) route. Still generally, the compositions representing a component of the system of the invention may be in the form of a capsule suitable for oral ingestion, in the form of an ointment, cream or lotion suitable for topical administration, in a form suitable for delivery as an eye drop, in an aerosol form suitable for administration by inhalation, such as by intranasal inhalation or oral inhalation.

For administration as an injectable solution or suspension, non-toxic parentally acceptable diluents or carriers can include, Ringer's solution, isotonic saline, phosphate buffered saline, ethanol and 1,2-propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glycel, monostearate or glyceryl distearate which delay disintegration of the capsule.

Adjuvants typically include emollients, emulsiflers, thickening agents, preservatives, bactericides and buffering agents.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinyopyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulfite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides, or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene to sorbitan mono- or di-oleate, -stearate or -laurate, and the like.

The emulsions for oral administration may further comprise one or more emulsifying agents. Suitable emulsifying agents include dispersing agents as exemplified above, or natural gums such as guar gum, gum acacia or gum tragacanth.

The topical formulations for use in the present invention, comprise an active ingredient together with one or more acceptable carriers, and optionally any other therapeutic ingredients.

Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops for use in the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilised. Sterilisaton may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorheidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturiser such as glycerol, or oil such as castor oil or arachis oil.

Creams, ointments or pastes according to the present invention are semi-solid formulations of the active ingredient for external application. They may be prepared by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The formulation may incorporate any suitable surface active agent, such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

The compositions for parenteral administration will commonly comprise a solution of an active agent useful a component of the system of the present invention or a cocktail thereof dissolved in an acceptable carrier, such as water, buffered water, 0.4% saline, and 0.3% glycine etc, wherein such solutions are sterile and relatively free of particulate matter.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The pharmaceutical compositions representing a component and/or active agent of the system of the invention may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The formulations in liposome form may contain stabillsers, preservatives, excipients and the like. The preferred lipids are the phospholipids and the phosphatidylcholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

4. Kits

Systems suitable for use in accordance with the present invention can be available as kits whereby respective components of the system are packaged separately, Suitable containers Include glass containers, plastic containers, and strips of plastic or paper such as blister packs. The kits typically include containers for housing the varius components and instructions for using the kit components in accordance with the methods of the present invention.

The kits can be used in accordance with the methods of treatment or methods of detection of the present invention.

An example of one kit according to th present invention is used for inducing thrombosis of tumour vasculature and necrosis of a tumour. The kit includes a first container containing GSAO-B and a second container containing avidin and a third container containing tTF-B. The GSAO-B is first administered to a vertebrate, followed by an interim period, typically from 12 to 24 hours, still typically about 18 hours. The second component, avidin, is combined with the third component, tTF-B and the resultant avidin-tTF-B complex administered to the vertebrate. This kit allows GSAO-B to target apoptotic cells such that when the avidin-tTF-B complex is administered, the tT-B binds to the GSAO-B at apoptotic cells and induces thrombosis.

5. Treatment and/for Prevention of Disease

The systems for use in the invention are useful in the treatment of various disorders and diseases of vertebrates. Examples of disorders and diseases may be grouped into broad categories such as the following: angiogenesis-dependent diseases, cellular proliferative diseases (e.g. psoriasis, IBD, malignancies, restenosis), inflammatory disorders, auto-immune diseases, blood vessel diseases, thrombosis, cancer, neurodegenerative disorders (e.g Alzhelmer's disease, Parkinson's disease), myelodysplastic syndromes, ischaemia/repurfusion injury and organ transplant injury.

Typically, the cancer is selected from the group consisting of carcinogenic tumours, tumours of epithelial origin, such as cola-rectal cancer, breast cancer, lung cancer, head and neck tumours, hepatic cancer, pancreatic cancer, ovarian cancer, gastric cancer, brain cancer, bladder cancer, prostate cancer and urinary/genital tract cancer; mesenchymal tumours, such as sarcoma; and haemopoletic tumours such as B cell lymphoma.

Typically, the cancer is a haematological tumour. More typically, the cancer is a solid tumour, The systems of the invention may also be used in the treatment of inflammatory disorders and/or auto-immune diseases, examples of which include the following: rheumatoid arthritis, seronegative arthritides and other inflammatory arthritides, systemic lupus erythematosus, polyarteritis and related syndromes, systemic sclerosis, Sjögren's syndrome and other inflammatory eye disease, mixed connective tissue disease, polymyositis and dermatomyositis, polymyalgia rheumatica and giant cell arteritis, inflammatory joint disease, non-inflammatory arthropathies and soft tissue rheumatism, algodystrophy.

Examples of blood vessel disease and thrombosis for which the systems of the invention are useful in a preventive manner and/or in the treatment of, include the following: progression of atherosclerosis; cerebrovascular accidents such as transient ischaemic, completed stroke, and after carotid surgery; acute myocardial infarction (primary and secondary); angina; occlusion of coronary artery bypass graft occlusion following percutaneous transluminal coronary angioplasty; occlusion following coronary stenting; vascular occlusion in peripheral arterial disease; venous thromboembolic disease following surgery, or during pregnancy, or during immobilisation.

Examples of small vessel disease for which the systems of the invention are useful include the following: glomerulonephritis; thrombotic thrombocytopenic purpura; the haemolytic uraemic syndrome; placental insufficiency and preeclampsia.

The systems of the invention may also be used for the treatment of vascular syndromes and myeloproliferative diseases.

The systems of the invention may also find use in the prevention of thrombosis formation in the following situations: artificial/prosthetic vascular shunts and grafts; prosthetic heart valves; cardiopulmonary bypass procedures; haemoperfision and haemodialysis.

Typically, the systems of the invention may be used in combination with other known treatments, such as surgery and/or therapeutic agents, including chemotherapeutic or radiotherapeutics. For example, when used in the treatment of solid tumours, compounds of the present invention may be administered with chemotherapeutic agents such as: adriamycin, taxol, fuorouricil, melphalan, cisplatin, alpha interferon, COMP (cyclophosphamide, vincristine, methotrexate and prednisone), etoposide, mBACOD (methotrexate, bleomycin, doxorubicin, cyclophosphamide, vincristine and dexamethasone), PROMACE/MOPP (prednisone, methotrexate (w/feucovin rescue), doxorubicin, cyclophosphamide, taxol, etoposide/mechlorethamine, vincristine, prednisone and procarbazine), vincristine, vinblastine, angioinhibins, TNP-470, pentosan polysulfate, platelet factor 4, angiostatin, LM609, SU-101. CM-101, Techgalan, thalidomide, SP-PG and the like. Other chemotherapeutic agents include alkylating agents such as nitrogen mustards including mechloethamine, melphan, chlorambucil, cyclophosphamide and ifosfamide; nitrosoureas including carmustine, lomustine, semustine and streptozocin; alkyl sulfonates including busulfan; triaznes including dacarbazine; ethyenimines including thlotepa and hexamethyimelamine; folic acid analogues including methotrexate; pyrimidine analogues including 5-fuorouracil, cytosine arabinoside; purine analogues including 6-mercaptopurine and 6-thioguanine; antitumour antibiotics including actinomycin D; the anthracyclines including doxorubicin, bleomycin, mitomycin C and methramycin; hormones and hormone antagonists including tamoxifen and cortiosteroids and miscellaneous agents including cisplatin and brequinar.

Typically, the physiological system to be treated in accordance with the present invention (e.g, the hepatic system, pancreatic system) may be isolated by or during surgery prior to administration of the system of the invention.

The invention will now be described in greater detail by reference to specific Examples which should not be construed as in any way limiting the scope of the invention.

EXAMPLE 1

Synthesis of Arsenoxide Compounds

The following chemicals were purchased and used without further purification: phenylarsenoxide, bromoacetyl bromide, sulfur dioxide, $d_6$-dimethylsulfoxide, deuterium oxide, methanol, 98% sulfuric acid, 48% hydrobromic acid, 37% hydrochloric acid (Ajax; Auburn, NSW); dichloromethane, potassium hydroxide, sodium hydrogen carbonate, sodium hydroxide (BDH, Kilsyth, VIC); P-2 Gel extra fine 1,800 MW cut-off (Bio-Rad, Hercules, Calif.); 2,3-dimercaptopropanol (DMP); thionyl chloride (Merck, Darmstadt, Germany); 6,8-thioctic acid, ethylenediaminetetraacetic acid, N-(2-hydroxyethyl)piperazine-N'-(2-ethanesulfonic acid), sodium carbonate, sodium chloride, sodium iodide (Sigma, Castle Hill, NSW); p-arsanilic acid (Tokyo Kasei Kogyo, Tokyo, Japan); glycine (ICN, Aurora, Ohio); 6-((6-((biotinoyl)amino)hexanoyl)amino)hexanoic acid, succinimidyl ester (biotin-XX, SE) were obtained from Molecular Probes, Eugene, Oreg., All other reagents were of analytical grade.

Instrumentation—1D and 2D NMR spectra were obtained using a Bruker DPX300 nuclear magnetic resonance spectrometer, with $^1$H-and $^{13}$C detected at 300.17 MHz and 75.48

MHz, respectively. UV-visible absorbances were recorded on a Molecular Devices Thermomax Plus (Palo Alto, Calif.) microplate reader.

Preparation of acidified deuterium oxide—Fresh thionyl chloride was cautiously added to an excess of deuterium oxide. After evolution of $SO_2$ had ceased, the resulting solution (0.6 ml) was added to GSAO (ca 50 mg) in a 5 mm NMR tube. This sample was used to obtain the NMR spectra.

Example 1(a)

Synthesis of
4-(N-(S-glutathionylacetyl)amino)phenylarsenoxide (GSAO)

Figure 1:
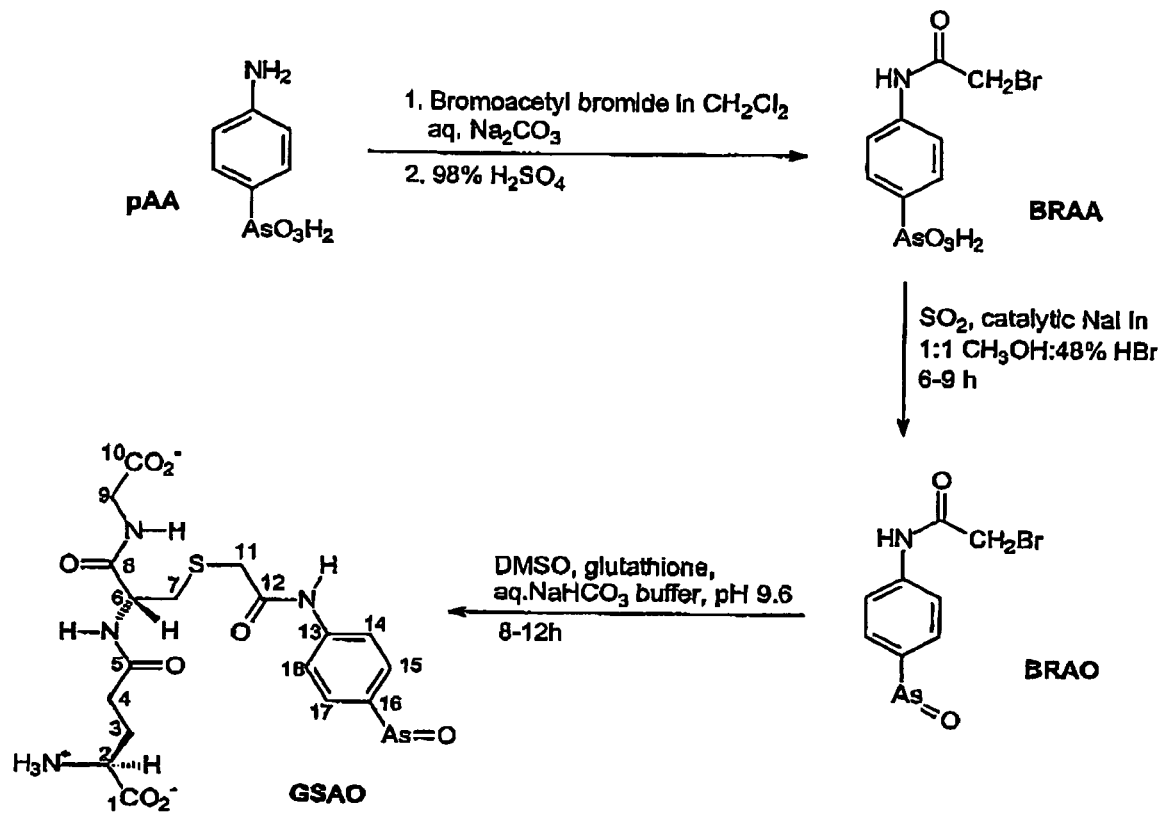
FIG. 1. Synthesis of GSAO. Schematic representation of the synthesis of GSAO showing the stereochemistry and the numbering scheme used in the discussion of the 2D $^1H$—$^{13}C$ HMBC NMR spectrum.

The total synthesis of GSAO is represented schematically in FIG. 1.

Synthesis of 4-(N-bromoacetyl)amino)phenylaronic acid (BRAA)

Sodium carbonate (40.14 g, 378.7 mmol) was added to water (200 mL) and stirs at room temperature until all solids had dissolved. To the stirred carbonate solution was added p-arsanillc acid (29.99 g, 138.2 mmol), portionwise, and the volume of the solution made up to 300 mL with addition of more water. The solution (pH 10 to 11) was allowed to stir for 30 mins, and if necessary, was filtered to remove any undissolved solid before being refrigerated for 2 to 3 hours. The solution was transferred to a separating funnel and ice chips were added. Bromoacetyl bromide (15 mL, 34.76 g, 172.1 mmol) was diluted in dichloromethane (50 mL) and approximately half of the dichloromethane solution was added carefully to the cold aqueous solution. The mixture was cautiously shaken, with frequent venting to avoid excessive build up of pressure. After 1 to 2 mins, the evolution of carbon dioxide had subsided, and more vigorous shaking was undertaken. The remaining portion of bromoacetyl bromide was carefully added and the procedure repeated. When the reaction was over, the solution was found to be pH 7. The lower dichloromethane layer was discarded, and the aqueous layer transferred to a 1 L flask and carefully acidified by dropwise addition of 98% sulfuric acid. Complete precipitation of the white product required addition of acid until the solution was approximately pH 1. The crude product was collected and dried at the pump, typically in yields of 50% to 75%. $^1$H-NMR ($d_6$-DMSO): δ4.09 (s, 2H), 7.73 (d, J=9 Hz, 2H), 7.83 (d, J=9 Hz, 2H), 10.87 (s, 1H). $^{13}$C-NMR ($d_6$-DMSO); δ30.53, 119.97, 127.34, 131.56, 143.08, 166.00 ppm.

Synthesis of 4(N-bromoacetyl)amino)phenylarsenoxide hydrate (BRAO.xH$_2$O)

Into a 3-necked 500 mL round-bottomed flask was placed BRAA (12.15 g, 36 mmol). The solid was dissolved with swirling in a mixture of methanol (75 mL) and hydrobromic acid (48%, 75 mL), giving a transparent yellow solution. The solution was filtered to remove residual solids. Sodium Iodide (0.20 g, 1.3 mmol was added as a catalyst, whereupon the colour of the solution darkened to orange-brown, then sulfur dioxide gas was slowly (ca. 2 bubbles per second) passed through the stirred solution for approximately 2.5 hours. The resultant white precipitate was collected using a Büchner funnel, giving the product (17.43 g) as a damp white solid. The activity of a solution made by dissolving a portion of the solid (40.7 mg) in deoxygenated DMSO (800 μL) was determined to be 56 mM (see below). Hence, the molecular weight of BRAO.xH$_2$is 908.5, that is, 35% w/w BRAO and 65% w/w H$_2$O. Therefore, the "anhydrous" weight of the BRAO product was 35% of 17.43 g, that is, 6.10 g (19 mmol, 53% yield). $^1$H-NMR (d6-DMSO):δ4.85 (s, 2H), 7.78 (d, J=9 Hz, 2H) 7.86 (d, J=9 Hz, 2H), 11.36 (s, 1H). $^{13}$C-NMR ($d_6$-DMSO); δ30,55, 119.22, 130.52, 140.04, 145.04, 165.52 ppm.

Synthesis of 4-(N-(S-glutathionylacetyl)amino)phenylarsenoxide (GSAO)

DMSO (10 mL) was deoxygenated by passing a stream of nitrogen gas through it for a few minutes, and used to dissolve BRAO.xH$_2$O (1.00 g, 2.48 mmol active arsenoxide). Glutathione (1.15 g, 3.74 mmol, 1.5 eq) was dissolved in 0.5 M bicarbonate buffer, pH 9.6 (35 mL), and added to the solution of BRAO.xH$_2$O in DMSO. The total volume was made up to 50 mL with 0.5 M bicarbonate buffer, and the solution gently agitated at room temperature overnight. Cautious neutralisaton with 37% hydrochloric acid, followed by lyophilisation gave a white powdery product, which could be dissolved in water leaving no residual solid. The active arsenoxide concentration of the resultant solution was found to be 49.6 mM, determined using the DMP/DTNB assay (see below).

The product was purified using gel-filtration (P-2 Gel extra fine, 1.8 kDa cutoff, 50 g) on a 130 mL column, using 20 mM Hepes, 0.14 M NaCl, 1 mM EDTA, pH 7.4 buffer as the eluant at a flow rate of 0.10 mL/min. A total of 144 mL was collected (72 fractions of 2 mL) and monitored by UV (λ214 nm). Four peaks, A, B, C and D, were resolved. Peaks B and C showed activity in the DTNB/DMP assay (see below), and were assigned as GSAO and unreacted BRAO, respecively. Peaks A and D were tentatively assigned as the oxidation products GSSM and BRAA (the oxidation product of BRAO), respectively (see below). Unreacted glutathione was also detected (using DTNB) in the fractions corresponding to Peak A. The fractions corresponding to peak B were combined and deoxygenated with nitrogen gas to give a solution of GSAO (15 mM, approximately 12 mL). $^1$H-NMR (D$_2$O): δ1.93 (q, J=7 Hz, 2H), 2.35 (t, J=8 Hz, 2H), 2.84 (dd, J=14 Hz, J=5 Hz, 1H), 3.05 (dd, J=14 Hz, J=5 Hz, 1H), 3.35 (s, 2H), 3.58 (t, J=6 Hz, 1H), 3.64 (d, J=2 Hz, 2H), 4.48 (dd, J=9 Hz, J=5 Hz, 1H), 7.44 (d, J=8 Hz, 2H), 7.58 (d, J=8 Hz, 2H). $^{13}$C—NMR (D$_2$O): δ25.93, 31.16, 33.53, 36.01, 42.97, 52.83, 53.89, 121.29, 129,97, 138.77, 144.09, 170.90, 171.73, 173.75, 174.68, 175.76 ppm.

Figure 2:
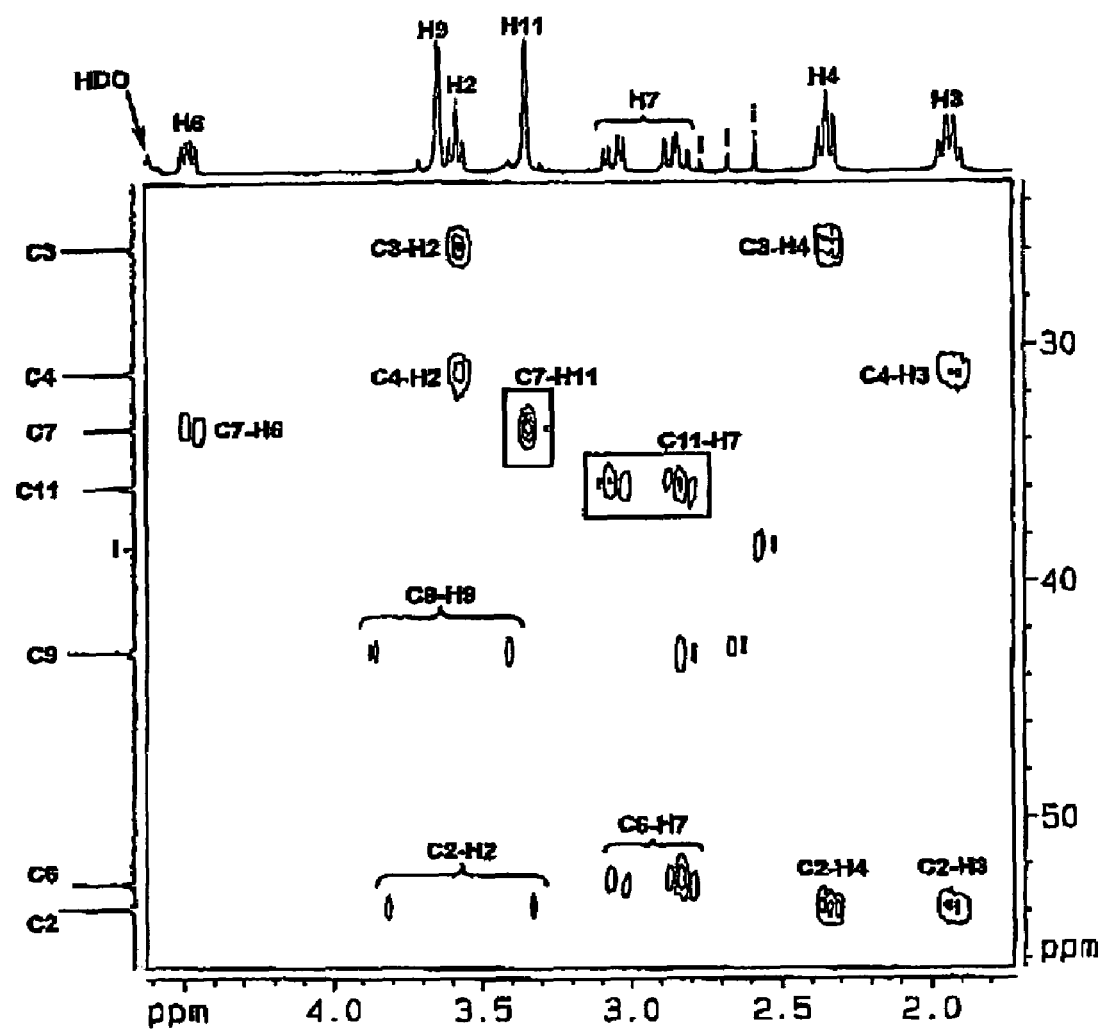
FIG. 2. Assignment of the Structure of GSAO. An expansion of the $^1H$—$^{13}C$ HMBC spectrum of GSAO in DCI/D$_2$O, showing the aliphatic region. The spectrum shows any long-range heteronuclear ($^1H$—$^{13}C$) coupling as crosspeaks, in line with the corresponding $^1H$ and $^{13}C$ signals along the horizontal and vertical axes. The boxed crosspeaks correspond to $^1H$—$^{13}C$ coupling between the C7 and C11 methylenes, confirming that alkylation by BRAO has occurred on the glutathione sulfur atom. Peaks and crosspeaks marked "i" are due to impurites; one-bond crosspeaks corresponding to the C9 methylene and the C2 methine are also observable as doublets due to incomplete filtering by the HMBC pulse sequence.

2D NMR spectroscopy was also used to confirm the structure of GSAO. A series of $^1$H and $^{13}$C NMR spectra, $^1$H, $^{13}$C, $^1$H—$^1$H COSY, $^1$H—$^{13}$C HMQC and $^1$H—$^{13}$C HMBC, were all found to be consistent with the structure proposed in FIG. 1. Considered together, all of the spectra permitted the unambiguous assignment of all carbon and non-exchangeable hydrogen atoms. An expansion of the $^1$H—$^{13}$C HMBC spectrum of GSAO, showing the aliphatic region, is shown in FIG. 2. The $^1$H—$^{13}$C HMBC technique correlates coupled $^1$H and $^{13}$C nuclei, but filters out directly bonded nuclei. This means that $^1$H and $^{13}$C nuclei that are separated by two, three, or (sometimes) four bonds appeared as crosspeaks in the spectrum. FIG. 2 shows that C11 is only strongly coupled to H7 (referring to the protons attached to C7), while C7 is strongly coupled to H11 in addition to H6. This confirms that the glutathione sulfur was successfully alkylated with BRAO.

Example 1(b)

Synthesis of
4-(N-(S-qlutathionylacetyl)amino)phenylarsonic acid (GSAA)

Figure 3:
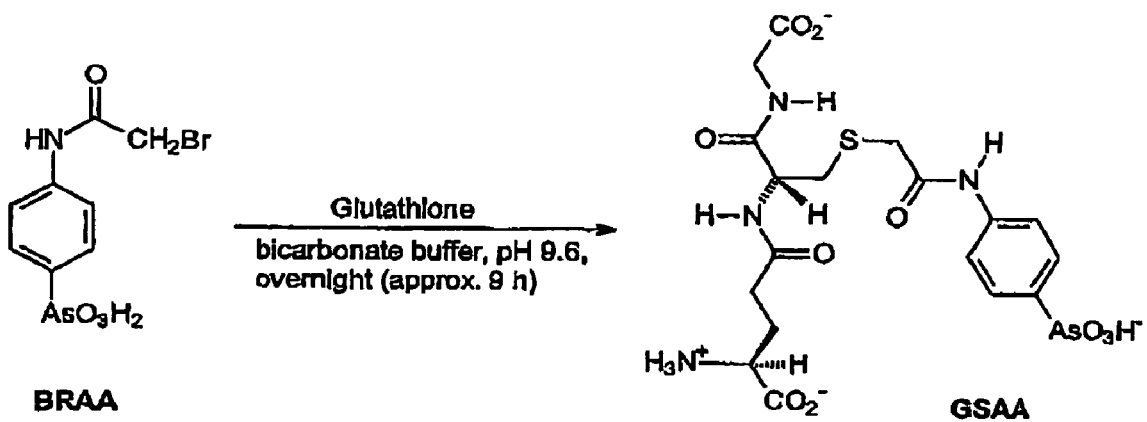
FIG. 3: Schematic representation of the synthesis of GSAO-A.

The synthesis of GSAA is represented schematically in FIG. 3.

BRAA (1.00 g, 2,96 mmol) and glutathione (1.36 g, 4.44 mmol, 1.5 eq) were dissolved in 0.5 M bicarbonate buffer, pH 9.6 (50 mL), and the solution gently agitated at room temperature overnight. Lyophilisation gave a white powdery product which was freely soluble in water, leaving no solid residue. The product was purified by gel-filtration on a 570 mL column (2.5×117 cm) of Bio-Gel P-2 extra fine (BioRad, Hercules, Calif.) using deionised water as the eluant at a flow rate of 0.1 mL per min. The product (GSAA) eluted from the column in a position corresponding to Peak A in the purification of GSAO.

Example 1(c)

Synthesis of 4-(N-(S-(N-(6-((6-((biotinoyl)amino)hexanoyl)amino)hexanoyl)glutathionyl)-acetyl)-amino)phenylarsenoxide (GSAO-B)

Figure 4:
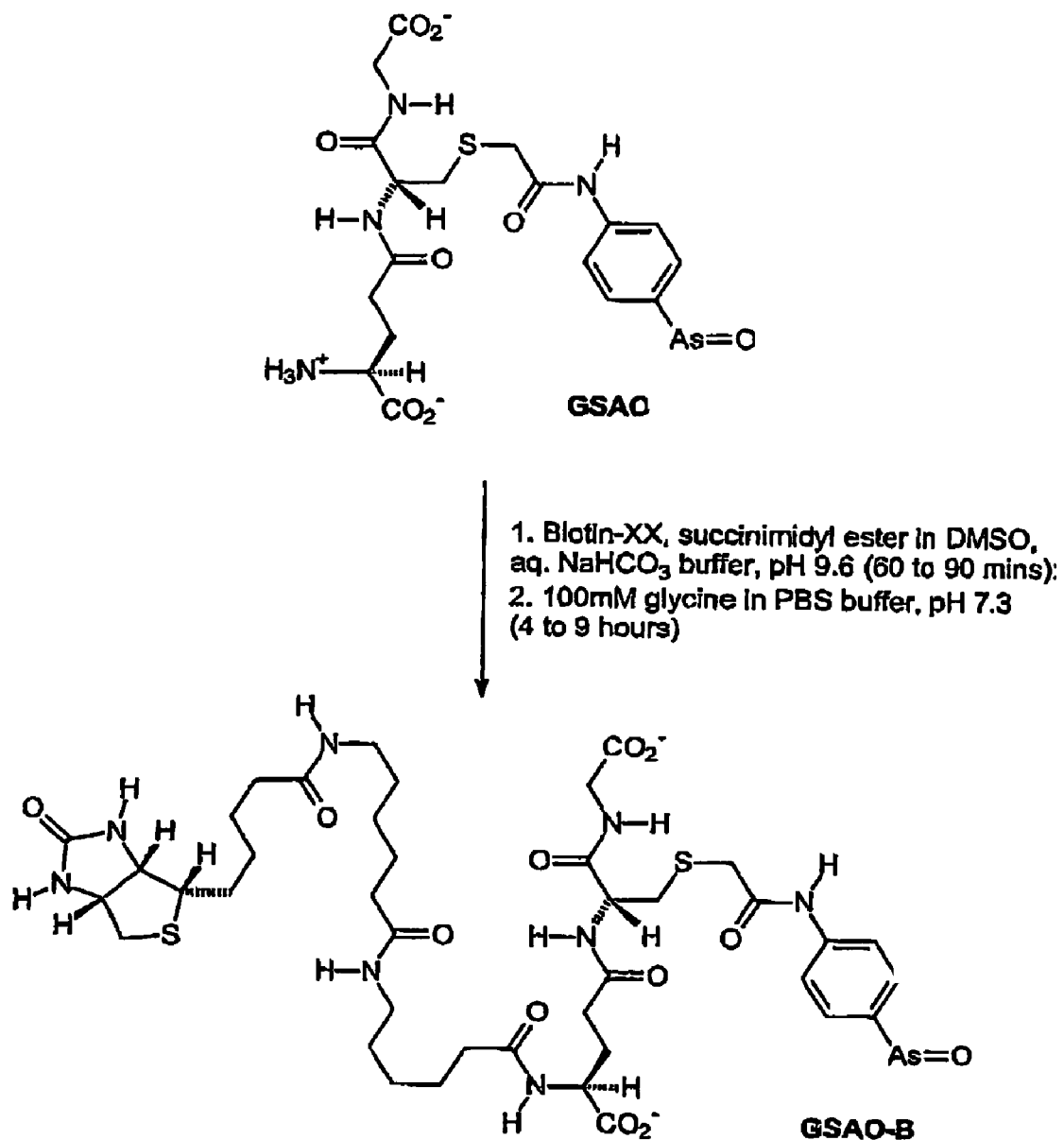
FIG. 4. Schematic representation of the synthesis of GSAO-B.

The synthesis of GSAO-B is represented schematically in FIG. 4.

GSAO (0.13 g) was dissolved in 0.5 M sodium bicarbonate buffer (5 mL, pH 8.5) and the concentration of active arsenical in the resultant solution was determined to be 39 mM. The buffered arsenical solution (4.2 mL, containing 165 µmol active arsenical) was added to a solution of biotin-XX, SE (100 mg, 176 µmol) in DMSO (1 mL), the mixture inverted a few times and then incubated at 4° C. for 4 hours. Glycine (17.5 mg, 233 µmol) was added and the mixture kept at 4° C. overnight. The concentration of trivalent arsenical in the GSAO-B product was determined to be 31 mM and the solution was used without further modification.

Example 1(d)

Conjugation of Fluorescein to GSAO or GSAA

A solution of fluorescein-5-EX succinimidyl ester (Molecular Probes, Eugene, Oreg.) (2.4 mg, 4.1 µmol) in DMSO (240 µL) was added to GSAO or GSAA (33.8 mM) in Mes buffer, pH 5.5 (5 mM, 473 µL), and the mixture was diluted with bicarbonate buffer, pH 9 (0.5 M, 3.287 mL) and allowed to stand at room temperature for 80 min. The reaction was then diluted with glycine (100 mM) in PBS (4 mL), and allowed to stand at room temperature overnight. The final solution contained trivalent arsenical (2.00 mM) and glycine (50 mM). The molar ratio of fluorescein-5× to GSAO or GSAA was ~1.5:1. The molecular weights of GSAO- and GSAA-fluorescein (GSAO-F and GSAA-F) are 1024 and 1040, respectively. The synthesis of GSAO-F is represented schematically in FIG. 5.

Example (1e)

Conjugation of Cy™5.5 to GSAO or GSAA

A solution of Cy™5.5 (Amersham Pharmacia Biotech, Uppsala, Sweden) (266 nmol) in bicarbonate buffer, pH 9 (0.5 M, 968 µL) was mixed with a solon of GSAO or GSAA (33.8 mM) in Mes buffer, pH 5.5 (5 mM, 32 µL), and allowed to stand at room temperature for 80 min. The reaction was then diluted with glycine (100 mM) in PBS (1 mL), and allowed to stand at room temperature overnight. The final solution contained trivalent arsenical (0.54 mM) and glycine (50 mM). The molar ratio of GSAO or GSAA-Cy™5.5 was ~4:1. The molecular 9 e o GSAO-Cy™5.5 and GSAA-Cy™5.5 are 1447 and 1463, respectively. The synthesis of GSAO-Cy™5.5 is represented schematically in FIG. 6.

Example 2

Example 2(a)

Assay of GSAO-B, GSAO-F and GSAO-Cy™5.5

Concentrations of GSAO-B, GSAO-fluorescein (GSAO-F) and GSAO-Cy™5.5 in solution were measured by filtrating with dimercaptopropanol (DMP) and calculating the remaining free thiols with 5,5'-dithiobis(2-nitrobenzoic acid) (DTNB) (Sigma, St. Louis, Mo.) (Donoghue et al., 2000). A stock solution of DMP (5 µL, 50 µmol was dissolved in DMSO (995 µL), giving a concentration of 50 mM DMP. A second dilution of the 50 mM DMP stock solution (10 µL) in pH 7.0 buffer (0.1 M HEPES, 0.3 M NaCl, 1 mM EDTA) (990 µL) gave a working solution of 500 µM DMP. The activity of the arsenical could then be determined by the titration of varying amounts of arsenical against the DMP working solution (10 µL) in a 96-well microtitre plate, with the total volume made up to 195 µL by addition of buffer. After a 10 minute incubation at room temperature, during which time the solutions were agitated on a plate shaker, 5 µL of a 37.9 mM the solution of DTNB (15 mg) in DMSO (1 mL) was added, and the plate incubated with shaking for another 10 minutes. The absorbance at 412 nm due to the formation of the TNB dianion was measured using a Molecular Devices Thermomax Plus (Palo Alto, Calif.) microplate reader. The extinction coefficient for the TNB dianion at pH 7.0 is 14,150 $M^{-1}cm^{-1}$ at 412 nm (Riddles et al., 1983). The conjugates were sterile filtered and stored at 4° C. in the dark until use. There was no significant loss in the active concentration of stock solutions of the arsenicals for at least a week when stored under these conditions. The glycine slows the oxidation of GSAO to GSAA (Donoghue et al, 2000).

Example 2(b)

Interaction of GSAO-B with PDI and thloredoxin

Figure 7:
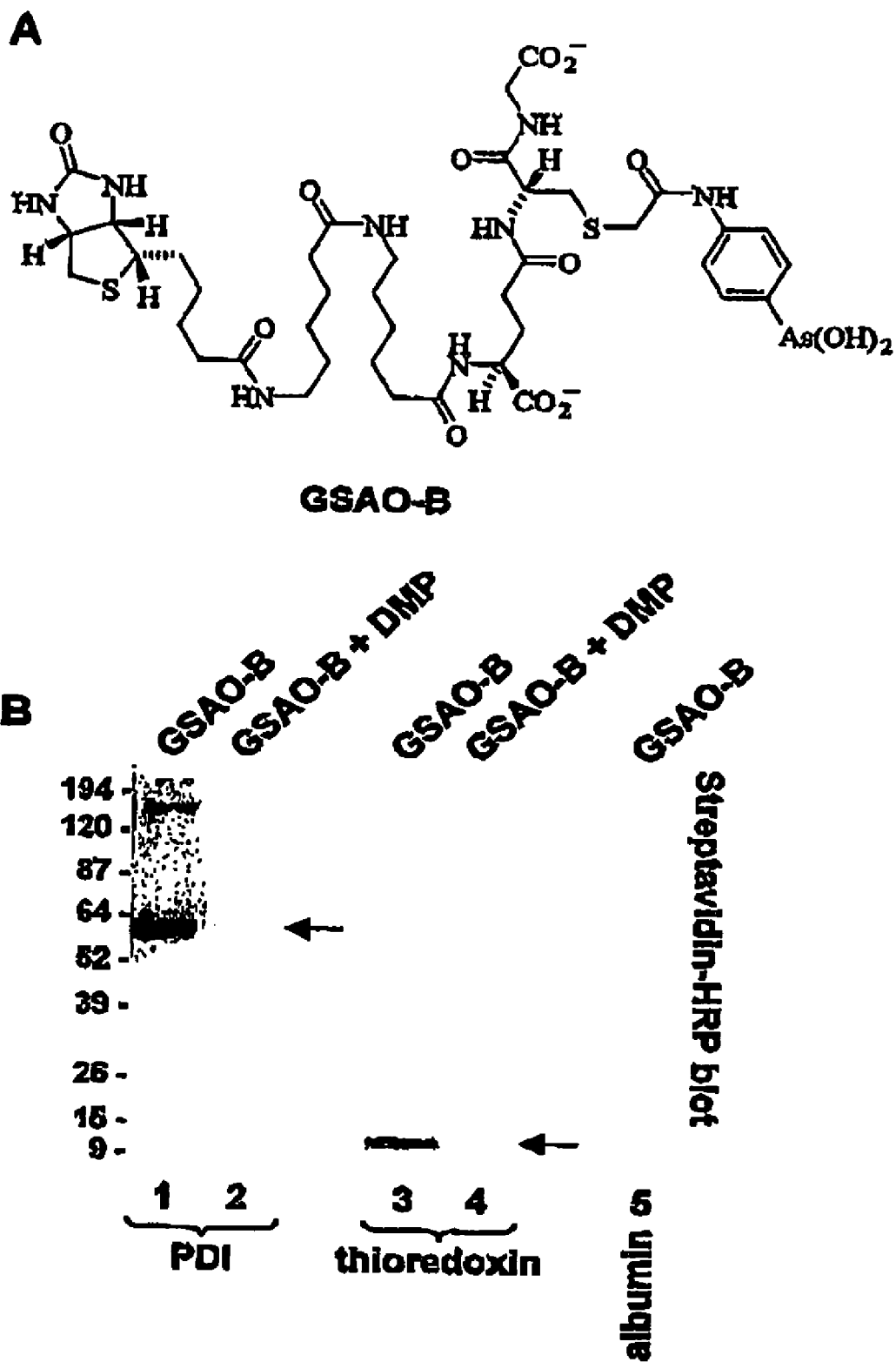
FIG. 7. Interaction of GSAO-B with PDI and thioredoxin. A Structure of GSAO-B. B Purified human recombinant PDI (5 µM), human recombinant thioredoxin (5 µM) or bovine serum albumin (5 µM) was incubated with dithiothreitol (10 µM) for 60 minutes at room temperature to ensure that the active site disulfide(s) of PDI and thioredoxin were in the reduced dithiol form. GSAO-B (100 µM) or GSAO-B and DMP (400 µM was then added and the reactions incubated for 30 minutes at room temperature. The labelled PDI (lanes 1 and 2), thioredoxin lanes 3 and 4) and albumin (lane 5) (75 pmoles) was resolved on 4-16% SDS-PAGE, transferred to PVDF membrane, and blotted with streptavidin-peroxidase to detect the GSAO-B label. The positions of M$_r$ markers are shown at left.

Human recombinant PDI and thloredoxin bound GSAO-B (FIG. 7). Recombinant human protein disulfide isomerase (PDI) was produced in *E. coil* and purified according to Jiang et al. (1999). In the experiment, purified PDI, thloredoxin or albumin as negative control were incubated with a 2-fold molar excess of dithiothreitol for 60 minutes to ensure that the active site disulfides of PDI and thloredoxin were in the reduced dithiol state. The proteins were then incubated with GSAO-B or GSAO-B and a 4-fold molar excess of DMP for 30 minutes. Equivalent moles of the labelled proteins were resolved on SDS-PAGE, transferred to PVDF membrane, and blotted with streptavidin-peroxidase to detect the GSAO-B label. Samples were resolved on 4-15% SDS-PAGE under non-reducing conditions and transferred to PVDF membrane. Proteins were detected by Western blot using an anti-PDI murine monoclonal antibody (Jiang et al., 1999) (used at 2 µg per mL). Rabbit anti-mouse horseradish peroxidase conjugated antibodies (Dako Corporalon, Carpinteria, Calif.) were used at 1:2000 dilution. GSAO-B-labelled proteins were blotted with streptavidin peroxidase (Amersham, Sydney, NSW) used at 1:1000 dilution. Proteins were visualised using chemiluminescence (DuPont NEN, Boston, Mass.) according to the manufacture's instructions. Chemiluminescence films were analysed using a GS-700 Imaging Densitometer and Multi-Analyst software (Bio-Rad, Hercules, Calif.).

Both PDI and thioredoxin incorporated GSAO-B but albumin did not The higher $M_r$ band in lane 1 of FIG. 7B was a small amount of aggregated PDI in the preparation (Jiang et al., 1999). It is noteworthy that the density of labelling of PDI was approximately twice that of thioredoxin which is consistent with the two active site dithiols of PDI versus the one of thioredoxin.

EXAMPLE 3

In vitro I In vivo Studies

Example 3(a)

Staining of Adherent Cells with GSAO-B

Methods

BAE cells were seeded at a density of $5 \times 10^5$ cells per well in 2-well glass chamber slides (Nunc, Naperville, Ill.) and allowed to attach overnight. Cells were treated for 16 h with 10 μM GSAO-B, then washed twice with PBS, bed in PBS containing 3.7% formaldehyde, permeabilised with PBS containing 3.7% formaldehyde and 0.1% TritonX-100, then washed twice and incubated for 1 h at room temperature with a 1:200 dilution of Alexa 488-conjugated streptavidin (Molecular Probes, Eugene, Oreg.) in PBS containing 1% BSA. Cells were then washed three times with PBS and mounted in VectaShield antifade agent (Vector Laboratories, Burlingame, Calif.). Pictures were taken with an Olympus BX60 microscope with BX-FLA fluorescence and a Diagnostic Instruments Spot Digital Camera and software v2.2 (Stewing Heights, Mich.).

Results

Figure 8:
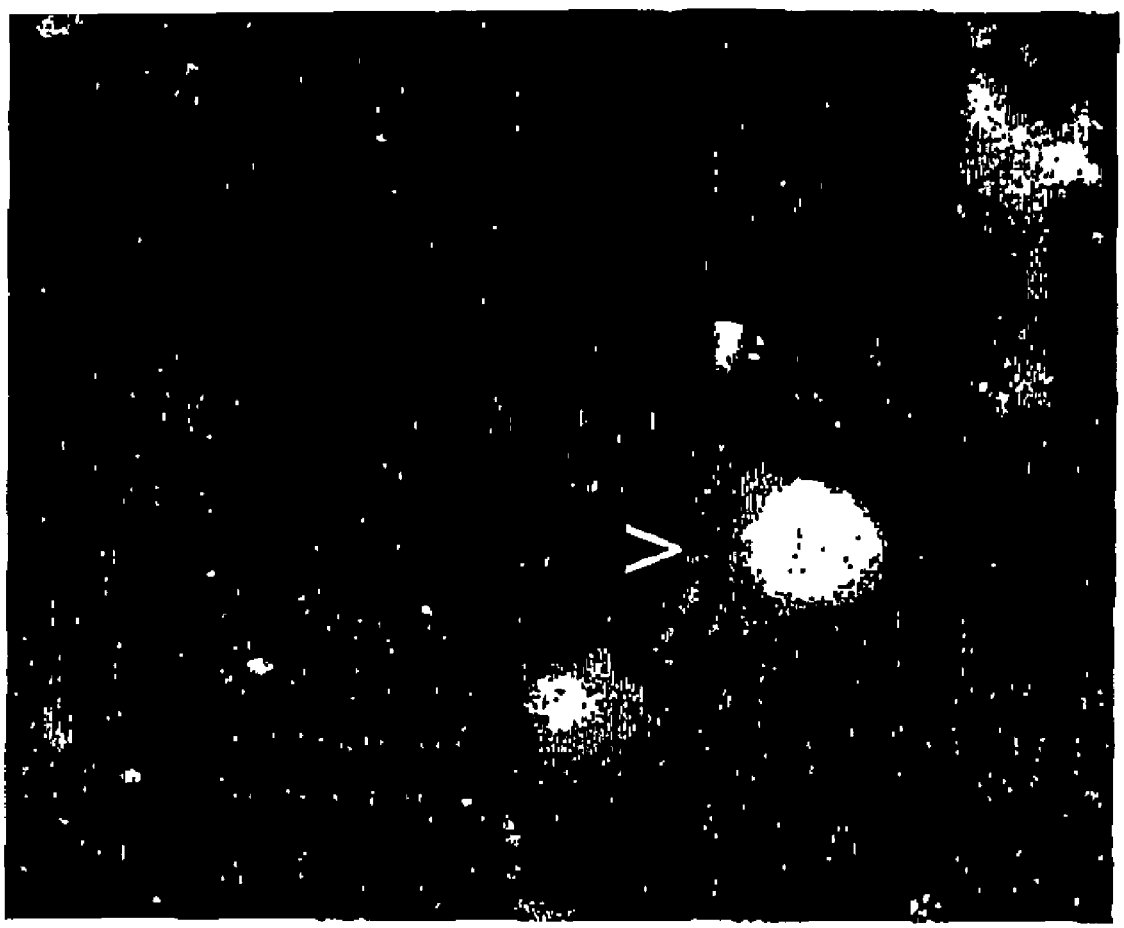
FIG. 8. GSAO-B labels the occasional cultured cell. Confluent BAE cells were stained with GSAO-B and visualised with streptavidin-Alexa 488, The occasional cell stained very brightly (see arrowhead). The vast majority of the cells bound very little GSAO-B.

When cultured endothelial cells were stained with GSAO-B and visualised with streptavidin-Alexa 488 it was observed that the occasional cell stained very brightly (FIG. 8). The vast majority of the cells bound very little GSAO-B.

Example 3(b)

GSAO Labelled Apoptotic Cells Following Caspase Activation

Methods
Cell Culture

HT1080 human fibrosarcoma and bovine aortic endothelial cells (ATCC, Bethesda, Md.) were cultured in DMEM containing 10% FBS, 2 mM L-glutamine, and 5 $U.mL^{-1}$ penicillin/streptomycin (Gibco BRL, Gaithersburg, Md.). The human microvascular endothelial cell line (HMEC-1) (Ades et al., 1992) was cultured in MCDB131 medium (Gibco BRL, Gaithersburg, Md.) containing 10% foetal bovine serum, 2 mM L-glutamine, 5 $U.mL^{-1}$ penicillin/streptomycin, 10 $ngml^{-1}$ epidermal growth factor (Gibco BRL, Gaithersburg, Md.) and 1 $\mu gml^{-1}$ hydrocortisone (Sigma, St. Louis, Mo.). Cells were detached with PBS containing 10 mM EDTA or with a trypsin/EDTA solution (Gibco BRL, Gaithersburg, Md.). Culture plates were from Coming Costar, Coming, N.Y.

Flow Cytometry of GSAO- and Annexin V-labeled Cells

HT1080 cells were treated for 20 h with 1 $\mu g.mL^{-1}$ camptothecin (Calbiochem, San Diego, Calif.), then detached with PBS containing 2.5 mM EDTA and combined with cells that had detached during incubation. The cells were washed twice with annexin V binding buffer (10 mM Hepes, 140 mM NaCl, 2.5 mM $CaCl_2$, pH 7.4), and $2 \times 10^5$ cells per treatment were incubated in 100 μL annexin V binding buffer containing 10 μM GSAO-F or GSAA-F for 15 min at room temperature with shaking. The cells were washed twice, then incubated for 15 min in 100 μL annexin V binding buffer containing 5 μl phycoerythrin-conjugated annexin V (annexin V-PE) (PharMingen, San Diego, Calif.) and 1 μl of a 100 $\mu g.mL^{-1}$ solution of propidium iodide (Molecular Probes, Eugene, Oreg.). The total volume was then made up to 500 μl with annexin V binding buffer, and the samples were transferred to ice. Flow cytometry was performed using a FACSstar flow cytometer (Beckton Dickson). Results are derived from $10^4$ cells per sample. To test the effect of caspase inhibition on to GSAO-F uptake, cells were treated with camptothecin in the absence or presence of 10 $\mu g.mL^{-1}$ Z-VAD-FMK (carbobenzoxy-valyl-alanyl-aspartyl-[O-methyl]-fluoromethylketone) (Calbiochem-Novabiochem, San Diego, Calif.), then detached, washed and incubated in annexin V binding buffer containing 10 μM GSAO-F for 15 min. The cells were washed twice and subjected to flow cytometry.

Results

Human fibrosarcoma HT1080 cells were treated with the topolsomerase inhibitor, camptothecin (Kaufmann, 1998), for 20 h to induce apoptosis, and untreated or camptothecin-treated cells were incubated with a combination of fluorescein-conjugatd GSAO (GSAO-F) or GSAA (GSAA-F) and phycoerythrin-conjugated annexin V (annexin V-PE). The fluorescence was quantitated by flow cytometry (FIG. 9a-f). An increase in apoptotic and dead cells after camptothecin treatment was apparent, with a 7.3-fold increase in the proportion of cells that had a phycoerythrin fluorescence of greater than 100 fluorescence units. This increase in annexin V-positive cells correlated with an 8.6-fold increase in the proportion of cells whose fluorescein fluorescence was greater than 1027 units (FIG. 9c). By contrast, camptothecin treatment did not increase the proportion of cells that co-labelled with GSAA-F and annexin V-PE (FIG. 9f). The mean fluorescein fluorescence of untreated cells labelled with GSAA-F or GSAO-F was similar (255 units for GSAO-F; 213 units for GSAA-F), whilst for the camptothecin-treated cell population a clear difference in mean fluorescence was apparent (1400 units for GSAO-F, 219 units for GSAA-F). Similar results were obtained when apoptosis was induced in human dermal microvascular endothelial calls using either 1 $\mu g.mL^{-1}$ camptothecin or 10 or 25 mM homocysteine for 24 h (not shown).

HT1080 cells were left untreated or treated with camptothecin to induce apoptosis, then detached and labelled with GSAO-F, annexin V-PE and the nucleic acid binding dye, propidium iodide. Propidium iodide is taken-up by cells in the later stages of apoptosis and by necrotic cells, whilst annexin V binds to cells early in the apoptotic program. Annexin V-PE fluorescence was plotted against GSAO-F fluorescence for all cells, and all cells excluding those that had taken-up propidium iodide (>200 fluorescence units). The percentage of cells that stained brightly with both annexin V-PE (>200 fluorescence units) and GSAO-F (>1980 fluorescence units) are shown (FIG. 9g). GSAO-F bound to both apoptotic and dead cells.

The caspases are a class of aspartate proteases that are activated by apoptotic stimuli in all cells, triggering the proteolysis of cellular targets such as the cytoskeleton and the fragmentation of nuclear DNA (Thornberry and Lazebnik, 1998). The activation of caspases is an essential component of the apoptotic program, and the broad-spectrum caspase inhibitor Z-VAD-FMK has been used extensively to block caspase-dependent processes (Zhu et al., 1995). HT1080 cells were treated with camptothecin as above, in the presence or absence of Z-VAD-FMK. Treatment with Z-VAD-FMK substantially blocked the increase in GSAO-F positive cells seen with camptothecin treatment, indicating that caspase activity is a requirement for the uptake of GSAO into apoptotic cells.

Example 3(c)

GSAO Entered Apoptotic Cells and Labelled Proteins Containing Closely-spaced Dithiols Methods
Confocal Microscopy of GSAO- and Annexin V-labelled Cells
HT1080 cells were treated for 20 h with 1 μg.mL$^{-1}$ camptothecin, then detached with PBS containing 10 mM EDTA, washed with annexin V binding buffer, and incubated for 15 min in annexin V binding buffer containing 10 μM GSAO-F and 1:20 (v/v) Alexa594conjugated annexin V (Molecular Probes, Eugene, Oreg.). The cells were then washed twice with annexin V binding buffer and pipetted onto a microscope slide. Transverse cell sections were captured using an Olympus BX60 microscope and an Optiscan F900e confocal unit and software (Optiscan, Notting Hill, Austrlia).
Labelling of Cells with GSAO-B
HT1080 cells were for 20 h with 1 μg.mL$^{-1}$ camptothecin and labeled with 10 μM GSAO and annexin V-PE as described above for labelling with GSAO-F and annexin V-PE. Cells were sorted on the basis of their annexin V-PE fluorescence, washed three times with PBS and 4×10$^4$ cells were lysed in 40 μL of RIPA buffer (50 mM Tris-HCl, 0.5 M NaCl, 1% Triton X-100, 1% sodium deoxycholate, 0.1% SDS, 10 μM leupeptin, 10 μM aprotinin, 2 mM phenylmethylsulfonyl fluoride, 5 mM EDTA, pH 8.0) at 4° C. Equal amounts of lysate were electrophoresed on an 8-16% gradient SDS-polyacrylamide gel (Gradipore, Sydney), transferred to polyvinyldiethylene fluoride (PVDF) membrane (Millipore, Bedford, Mass.) and biotinylated proteins were detected with a 1:2000 dilution of avidin-peroxidase (Molecular Probes, Eugene, Oreg.). To identify proteins that had incorporated GSAO-B, 20 μl of RIPA lysate was incubated with 5 μl streptavidin-dynabeads (Dynal Biotech, Oslo, Norway) for 15 min at 4° C. The beads were then washed twice with RIPA buffer, resuspended in 20 μl SDS-PAGE loading buffer, resolved on SDS-PAGE, transferred to polyvinylidene difluoride membrane, and the PDI was detected by Western blot using 2 μg.mL$^{-1}$ of anti-PDI polyclonal antibodies (Donoghue et al., 2000) and 1:2000 dilution of goat anti-rabbit peroxidase-conjugated antibodies (Dako Corporation, Carpinteria, Calif.). The blots were developed using ECL enhanced chemiluminescence (NEN, Boston, Mass.).

Untreated and camptothecin-treated HT1080 cells were also labelled with 10 μM GSAO-B in the absence or presence of 50 μM dimercaptopropanol for 15 min at 20° C. with shaking. Cells were washed three times with PBS and 2×10$^5$ cells lysed in 100 μL of RIPA buffer at 4° C. Lysates were resolved on SDS-PAGE and blotted with avidin-peroxidase as described above.
Results
HT1080 cells were treated with camptothecin to induce apoptosis, then detached and is labelled with GSAO-F and annexin V-Alexa-594. Cells were imaged by confocal microscopy. GSAO-F distributed in the cytoplasm of annexin V-positive cells (FIG. 10a(i-vi)). There was negligible GSAO-F fluorescence in cells that did not label with annexin V (FIG. 10a(vii)).

HT1080 cells were treated with camptothecin to induce apoptosis, then detached and labelled with annexin V-PE and biotin-conjugated GSAO (GSAO B) (Donoghue et al., 2000). Cells were sorted into annexin V-positive (>100 fluorescence units) and annexin V-negative (<100 units) populations and equivalent numbers of cells from each population were resolved on SDS-PAGE and blotted with streptavidin-peroxidase to detect the GSAO-labelled proteins. Approximately seven proteins clearly incorporated GSAO-B in annexin V-positive cells (FIG. 10b). The level of incorporation of GSAO-B into annexin V-negative cells was negligible by comparison.

The GSAO-B-labelled proteins were also collected on streptavidin-dynabeads, resolved on SDS-PAGE and Western blotted for protein disulfide isomerase (PDI), a protein that is abundant in the endoplasmic reticulum and functions as a redox chaperone (Donoghue et al., 2000; Novia, 1999). The intensity of labelling of PDI in annexin V-positive cells was much higher than labelling of this protein in annexin V-negative cells (FIG. 10c).

To confirm that GSAO-B was interacting with closely-spaced dithiols in apoptotic calls, HT1080 cells were untreated or treated with camptothecin, then detached and labelled with GSAO-B In the absence or presence of dimercaptopropanol (FIG. 10d). This synthetic dithiol competes with protein dithiols for binding to GSAO-B (Donoghue et al., 2000). Again, there was much more labelling of the camptothecin-treated population than the untreated population, and the labelling of apoptotic cellular proteins by GSAO-B was ablated by incubating the cells with a 5-fold molar excess of dimercaptopropanol.

Example 3(d)

GSAO Labelled Apoptotic or Dead Tumour Cells Vivo

Methods
BALB/C-nude mice (Biological Resources Centre, University of New South Wales, Sydney) bearing S.C. BxPC-3 tumours in the proximal dorsum were given 36 mg/kg GSAO-B or GSAA-B-in 0.2 mL of PBS containing 20 mM glycine by S.C. injection in the hind flank. Mice were sacrificed 6 hours later and tumours were embedded in OCT compound (Sukura, Torrence, Calif.) and snap frozen in liquid nitrogen. 5 μM sections of the tumours were fixed with acetone and stained with StreptABComplex/HRP (Dako Corporation, Carpinteria, Calif.) according to the manufacture's instructions and counterstained with haematoxylin. Sections were also fixed with acetone/methanol, permeabilised with 0.1% Triton X-100, and stained with rabbit anti-activated caspase-3 antibody (Promega, Madison, Wis.)/goat anti-rabbit Texas Red and avidin-Alexa Fluor 488 (Molecular Probes, Eugene, Oreg.). Sections were counterstained with DAPI (Sigma, St. Louis, Mo.) and mounted with fluoromount-G (Southern Biotechnology, Birmingham, Ala.).
Results
Mice bearing S.C. BxPC-3 tumours were given GSAO-B or GSAA-B by S.C. injecton at a site remote from the tumour. The mice were sacrificed 6 hours later, the tumours excised and GSAO-B was detected with streptavidin-peroxidase. There was an accumulation of GSAO-B in regions of the tumour where apoptotic or dead cells were prevalent (FIG. 11a). GSAO-B stained cells that showed visible signs of apoptosis, including a condensed nucleus and shrunken cytoplasm, but not healthy tumour cells. There was no staining of tumour tissue that had not been incubated with streptavidin-peroxidase or of tumours from mice that had been given GSAA-B (not shown). Labelling of apoptotic cells was confirmed by staining sections for activated caspase-3 and GSAO-B. Activated caspase 3 and GSAO-B co-localised, while GSAA-B was not detected in the sections (FIG. 11b). GSAO-B was also detected in apoptotic and necrotic regions of AsPC-1 human pancreatic carcinoma tumours grown S.C. in SCID mice (not shown).

Example 4

In Vivo Imaging of Tumours with a Near-infrared Fluorescent Dye-labelled GSAO

Methods

C57BL/6 (Jackson Labs, Bar Harbor, ME) mice bearing S.C. Lewis lung tumours, SCID (Massachusetts General Hospital, Boston, Mass.) bearing S.C. BxPC3 tumours or TRAMP (Greenberg et al., 1995) mice were given 0.8 mg/kg GSAO-Cy™5.5, GSAA-Cy™5.5 or Cy™5.5 dye alone in 0.1 mL of PBS containing 20 mM glycine by S.C. injection in the right hind flank. The S.C. tumours were established in the proximal dorsum.

The imaging system utilised a Leica Microsystems fluorescence microscope (Allendale, N.J.) with a 100 W halogen lamp source and a filter system for CY™5.5 (Chroma Technology, Brattleboro, Vt.). Anaesthetised mice were restrained in a light proof box and fluorescence detected by a 12-bit monochrome charged coupled device (Photometrics, Tuscon, Ariz.). Exposure time was 8 seconds with images digitally acquired as 16-bit Tiff files in IPLab (Scanalytics, Fairfax, Va.). White light images of the tumours were also acquired.

Results

Cy™5.5 is a near-infrared fluorescent dye that has been used to image tumours in vivo (Weissleder et al., 1999). C57BL/6 mice being ~0.3 g murine Lewis lung tumours were administered 0.8 mg/kg GSAO-Cy™5.5 by S.C. injection and fluorescence images were acquired starting at 1 hour and ending at 48 hours after injecton. The white light image of a Lewis lung tumour is shown in FIG. 11c(A). The same view as seen through the near-infrared filter one hour after injection is shown in FIG. 11c(B). The images show tat the GSAO-Cy™5.5 had been absorbed into the vasculature and labelled the skin as well as the tumour. Fluorescence images of the dorsal sin and the tumour 24 hours after injection are shown in FIGS. 11c(C) and 11c(D), respectively. The GSAO-Cy™5.5 had cleared from the majority of the vasculature and only the tumour remained labelled. Examination of the urine indicated excretion of the GSAO-Cy™5.5 less then one hour after injection, with a peak intensity at 4-8 hours (not shown). Further examination of the tumours at 30, 36, 48 hours demonstrated a peak tumour to background signal ratio at 24 hours with little signal remaining at 48 hours. Neither GSAA-Cy™5.5 nor Cy™5.5 labelled Lewis lung tumours (not shown). Murine T241 fibrosarcoma tumours grown on the dorsum of C57BL/6 mice were also imaged using GSAO-Cy™5.5 (not shown).

Human tumours grown in immunodeficient mice were also labelled by GSAO-Cy™5.5 SCID mice bearing ~0.3 g human BxPC-3 pancreatic carcinoma tumours were administered 0.8 mg/kg GSAO-Cy™5.5 by S.C. injection and fluorescence images were acquired 1 and 24 hours after injecton. An excellent signal to background ratio for the tumour was again observed at 24 hours using GSAO-Cy™5.5 (FIG. 11d(C)). Neither GSAA-Cy™5.5 (FIG. 11d(B)) nor Cy™5.5 (FIG. 11d(D)) labelled BxPC3 tumours. The liver, heart lungs, bladder and kidneys were removed and examined for GSAO-Cy™5.5. Only the bladder and kidneys had any evidence of a near-infrared signal (not shown). In addition, human CRL-1973 embryonal tumours grown S.C. on the dorsum of SCID mice and human LnCaP prostate cells grown in the prostate of SCID mice were also imaged using GSAO-Cy™5.5 (not shown). These results indicate that GSAO-Cy™ can image both murine and human tumours in different strains of mice.

GSAO-Cy™5.5 was also used to image spontaneous prostate tumours in TRAMP mice (Greenberg et al., 1995). The animals were examined with ultrasound to verify the presence of tumours prior to imaging. TRAMP mice bearing prostate tumours were administered 0.8 mg/kg GSAO-Cy™5.5 by S.C. injection in the upper flank. As the depth detection threshold of the currently used imaging system was ≦1 cm (Weissleder et al., 1999), the abdomen was opened to reveal the tumour. The light field is filled with a large tumour and a central vein (FIG. 11e(A)). The tumour was labelled with GSAO-Cy™5.5, while the central vein was riot labelled (FIG. 11e(B)).

Example5

Example 5(e)

Labelling of tTF with MPB

Cloning and Mutation of tTF

Human TF cDNA was from Karen Fisher (Fisher et al., 1987). The primers used to amplify and mutate the extracellular domain of TF (tTF, residues 1-219) were 5'-ATCAG-GATCCGGCACTACAAATACTGTG-3' (forward primer) and 5'-ATCAGGATCCTTAACATCTGAATTC-CCCTTTCTCCTG-3' (reverse primer). Both primers contain a BamHI site outside the coding sequence to facilitate cloning. A TGT codon for cysteine is located at codon position 219 in the reverse primer, which replaces the GAA codon for glutamine. The Q219C tTF cDNA was amplified by PCR using DNA polymerase Pfx and cloned into the pTrcHisA vector (Invitrogen, San Diego, Calif.) at the BamHI site. The integrity of the tTF cDNA and the Q219C mutation was confirmed by automatic sequencing. The vector construct was used to transform E. coli BL21 Star (Invitrogen, San Diego, Calif.).

Expression, purification and biotin labeling of tTF

Recombinant tTF was expressed as described by Jiang et al. (1999), purified by ProBond (Invitrogen, San Diego, Calif.) affinity chromatography and refolded as described by Stone et al. (1995). The His-tag was cleaved from the purified, refolded protein by incubation of 1 unit of EKMax (Invitrogen, San Diego, Calif.) per 0.2 mg of tTF for 16 hours at room temperature. The cleaved His-Tag was separated from the tTF by anion-exchange chromatography. The reaction was dialysed against 20 mM Tris-HCl, pH 8.0 buffer and applied to a 1 mL Mono-Q column (Amersham Pharmacia Biotech, Uppsala, Sweden) equilibrated with the same buffer. The bound protein was resolved with a 0 to 0.5 M linear NaCl gradient. The tTF eluted at ~0.4 M NaCl.

The number of thiols in tTF were measured using DTNB. The tTF (~10 µM) was incubated with DTNB (~1 mM) in 0.1 M HEPES, 0.3 M NaCl, 1 mM EDTA, pH 7.0 buffer for 10 min at room temperature and the TNB was measured from the absorbance at 412 nm using a Molecular Devices Thermomax Plus (Palo Alto, Calif.) microplate reader. The extinction coefficient for the TNB dianion at pH 7.0 is 14,150 $M^{-1}cm^{-1}$ at 412 nm (Riddles et al., 1983). The tTF was incubated with a 20-fold molar excess of 3-(N-maleimidylpropionyl)biocytin (MPB) (Molecular Probes Incorporated, Eugene, Oreg.) for 16 h at room temperature to label the engineered Cys. Unreacted MPB was removed by dialysis.

Purified tTF and MPB-labelled tTF (tTF-B) were electrophoresed on a 8-16% gradient SDS-polyacrylamide gel (Gradipore, Sydney) and stained with Coomassie Brilliant Blue (Sigma, St. Louis, Mo.). On one occasion the proteins were transferred to polyvinyldiethylene fluoride (Millipore, Bedford, Mass.) and blotted with a 1:2000 dilution of avidin-peroxidase (Molecular Probes, Eugene, Oreg.) to detect the MPB label. The blot was developed using ECL enhanced chemiluminescence (NEN, Boston, Mass.).

The Q219C tTF is shown in FIG. 12A. The protein contained 0.77 mol of thiol per mol of protein, which reduced 0.13 mol of thiol per mol of protein upon reaction with MPB. Incorporation of MPB into Q219C tTF is shown in FIG. 12B.

Example 5(b)

Formation of the GSAO-B-avidin-tTF-B Complex

ELISA for Measuring Formation of the GSAO-B-avidin-tTF-B Complex

Human recombinant protein disulfide isomerase (PDI) was produced as described by Jiang et al. (1999). PDI (100 µl of 5 µg.mL$^{-1}$ in 0.1 M NaHCO$_3$, 0.02% azide, pH 8.3 buffer) was absorbed to Nunc PolySorp 96 well plates overnight at 4° C. in a humid environment. Wells were washed once With phosphate buffered saline (PBS) containing 0.05% Tween 20 (PBS/Tween), non-specific binding sites blocked by adding 200 µl of 3% BSA in PBS and incubating for 90 min at 37° C., and then washed two times with PBS/Tween. All the following incubations were for 30 min at room temperature with orbital shaking and the wells were washed three times with PBS/Tween after each incubation. Dithiothreitol (100 µl of 10 mM) was added to the wells to reduce the active site disulfides of PDI. GSAO-B (100 µl of 100 µM) was added to the wells to label the active site dithiols of PDI. tTF-B (0.1 µM) and increasing concentrations of avidin (Sigma, St. Louis, Mo.) (100 µl final volume) was added to the wells to form PDI-GSAO-B-avidin-tTF-B complexes. Murine anti-human TF monoclonal antibody (American Diagnostica, Greenwich, Conn.) (100 µl of 2 µg.mL$^{-1}$) was added to the wells to detect the bound tTF-B and bound murine antibody was measured with rabbit anti-murine peroxidase-conjugated IgG (100 µl of 1:500 dilution). Peroxidase activity was measured with 100 µl of 0.003% H$_2$O$_2$, 1 mg.mL$^{-1}$ 2,2'-azino-bis (3-ethylbenzthiazoline-6-sulfonic acid) in 50 mM citrate, ph 4.5 buffer for 20 min at room temperature with orbital shaking. Absorbances were read at 405 nm using a Molecular Devices Thermomax Kinetic Microplate Reader (Molecular Devices Corporation, Calif., USA). Results were corrected for control wells not coated with PDI.

GSAO-B reacts with the active site dithiols of purified PDI and with PDI on the cell-surface (Donoghue et al., 2000). This interaction has been used in a microtitre plate format to examine the formation of GSAO-B-avidin-tTF-B complexes. PDI was immobilised in microtitre wells, labelled with GSAO-B and incubated with tTF-B and increasing molar ratios of avidin. The bound tTF was detected using an anti-TF antibody. The optimal avidin:tTF-B molar ratio for formation of GSAO-B-avidin-tTF-B complexes was ~0.5:1 (FIG. 13).

Example 5(c)

Thrombosis of Tumour Vasculature and Necrosis of the Tumour by S.C. Administration of GSAO-B Followed by I.V. Administration of Avidin tTF-B Female 6-8 week old Balb/c nude mice (Biological Resources Centre, University of New South Wales, Sydney) were injected S.C. with 2.5×10$^6$ AsPC-1 cells in 0.2 mL of PBS in the proximal dorsal midline. Tumour volume was calculated using the relationship, a.b.$^2$.0.52, where a is the longest and b the shortest diameter. Tumours and organs were fixed in Buffered Formalde-Fresh (Fisher Scientific, Fair Lawn, N.J.), embedded in paraffin and 5 µm thick sections were cut and placed on glass slides. Sections were stained with haematoxylin and eosin.

SCID mice bearing ~0.6 g As-PC1 tumours were given 7.5 mg/kg GSAO-B in 0.15 mL of PBS containing 20 mM glycine by S.C. injecton in flank. The GSAO-B was allowed to clear from the general circulation for 18 hours and the mice were then given 1 mg/kg avidin-[tTF-B] (molar ratio 0.5:1) in 0.2 mL of saline by I.V. injection in the tail vein. The principle of this treatment regimen is shown in FIG. 14.

Approximately 75% of the tumour was visibly purple 2-4 hours after administration of avidin-tTF-B. The mice was sacrificed 10 days after administration of avidin-tTF-B and the tumour excised and examined histologically. There was marked thrombosis of the tumour vasculature and necrosis of the treated tumour (FIG. 15). Only a peripheral layer of tumour cells remained viable. The weight of the treated mouse did not change over the course of the experiment. At the conclusion of the experiment, the heart, lungs, liver, kidneys, and spleen of the treated mouse were examined histologically. There was no signs of thrombosis in any of the organs (not shown).

Example 6

Pharmaceutical Formulations

The compounds used as the components of the systems of the present invention may be administered alone, although it is preferable that they be administered as a pharmaceutical formulation. The active ingredient may comprise, for topical administration, from 0.001% to 10% by weight, and more typically from 1% to 5% by weight of the formulation, although it may comprise as much as 10% by weight.

In accordance with the best mode of performing the invention provided herein, specific preferred pharmaceutical compositions used as components of the systems of the present invention are outlined below. The following are to be construed as merely illustrative examples of formulations and not as a limitation of the scope of the present invention in any way.

Example 6(e)—Topical Cream Composition

A typical composition for delivery as a topical cream is outlined below:

| | |
|---|---|
| GSAO-Cy ™ 5.5 | 1.0 g |
| Polawax GP 200 | 25.0 g |
| Lanolin Anhydrous | 3.0 g |
| White Beeswax | 4.5 g |
| Methyl hydroxybenzoate | 0.1 g |
| Deionised & sterilised Water to | 100.0 g |

The polawax, beeswax and lanolin are heated together at 60° C., a solution of methyl hydroxybenzoate is added and homogenisation achieved using high speed stirring. The temperature is then allowed to fall to 50° C. The component of the present invention, in this example being GSAO-Cy™5.5, is then added and dispersed throughout, and the composition is allowed to cool with slow speed stirring.

Example 6(b)—Topical Lotion Composition

A typical composition for delivery as a topical lotion is outlined below:

| | |
|---|---|
| GSAO-Cy ™ 5.5 | 1.2 g |
| Sorbitan Monolaurate | 0.8 g |
| Polysorbate | 200.7 g |
| Cetostearyl Alcohol | 1.5 g |
| Glycerin | 7.0 g |
| Methyl Hydroxybenzoate | 0.4 g |
| Sterillsed Water about to | 100.00 ml |

The methyl hydroxybenzoate and glycerin are dissolved in 70 ml of the water at 75° C. The sorbitan monolaurate, polysorbate 20 and cetostearyl alcohol are melted together at 75° C. and added to the aqueous solution. The resulting emulsion is homogenised, allowed to cool with continuous stirring and the GSAO-Cy™5.5 is added as a suspension in the remaining water. The whole suspension is stirred until homogenised.

Example 6(c)—Eye Drop Composition

A typical composition for delivery as an eye drop is outlined below:

| | |
|---|---|
| GSAO-Cy ™ 5.5 | 0.3 g |
| Methyl Hydroxybenzoate | 0.005 g |
| Propyl Hydroxybenzoate | 0.06 g |
| Purified Water about to | 100.00 ml. |

The methyl-and propyl hydroxybenzoates are dissolved in 70 ml purified water at 75° C., and the resulting solution is allowed to cool. GSAO-Cy™5.5 is then added, and the solution sterilised by filtration through a membrane filter (0.22 μm pore size), and aseptically packed into sterile containers.

Example 6(d)—Composition for Inhalation Administration

For an aerosol container with a capacity of 20-30 ml: a mixture of 10 mg of GSAO-Cy™5.5 with 0.5-0.8% by weight of a lubricating agent such as polysorbate 85 or oleic acid, is dispersed in a propellant, such as freon, and put into an appropriate aerosol container for either Intranasal or oral inhalation administration.

Example 6(d)—Composition for Parenteral Administration

A pharmaceutical composition of the present invention for intramuscular injection could be prepared to contain 1 mL sterile buffered water, and 1 mg of GSAO-Cy™5.5.

Similarly, a pharmaceutical composition for intravenous infusion may comprise 250 ml of sterile Ringer's solution, and 5 mg of GSAO-Cy™5.5.

Example 6(f)—Capsule Composition

A pharmaceutical composition of GSAO-Cy™5.5 in the form of a capsule may be prepared by filling a standard two-piece hard gelatin capsule with 50 mg of GSAO-Cy™5.5, in powdered form, 100 mg of lace, 35 mg of talc and 10 mg of magnesium stearate.

Example 6(g)—Injectable Parenteral Composition

A pharmaceutical composition of this invention in a form suitable for administration by injecton may be prepared by mixing 1% by weight of GSAO-Cy™5.5 in 10% by volume propylene glycol and water. The solution is sterilised by filtration.

Example 6(h)—Ointment Composition

A typical composition for delivery as an ointment includes 1.0 g of GSAO-Cy™5.5, together with white soft paraffin to 100.0 g, dispersed to produce a smooth, homogeneous product.

The invention claimed is:

1. A system for selectively targeting an active agent to apoptotic cells or dead cells, wherein said active agent is a diagnostic agent selected from radionucleotides, paramagnetic ions and X-ray imaging agents, the system comprising:

an arsenoxide compound having the following structural formula:

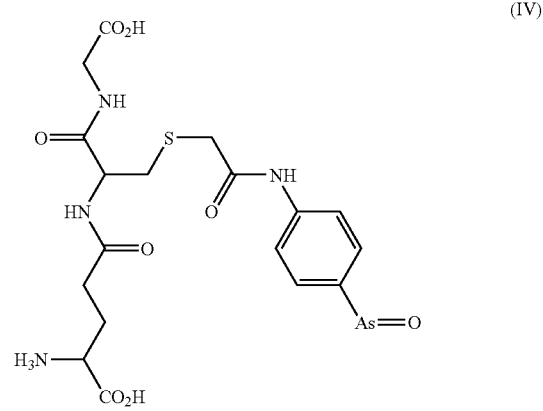

(IV)

linked to a binding member, wherein said binding member is a metal ion ligand capable of binding said active agent wherein the metal ion ligand is selected from the group consisting of

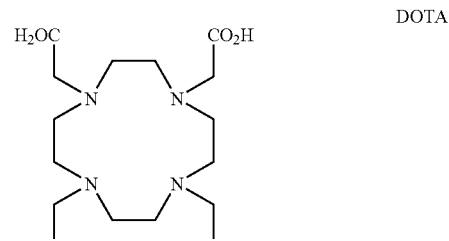

DOTA

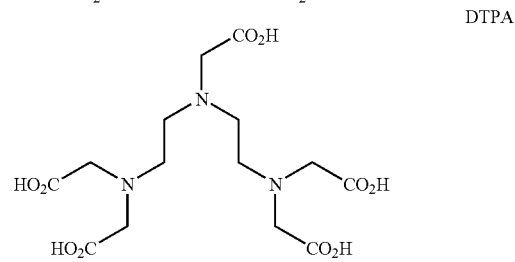

DTPA

-continued

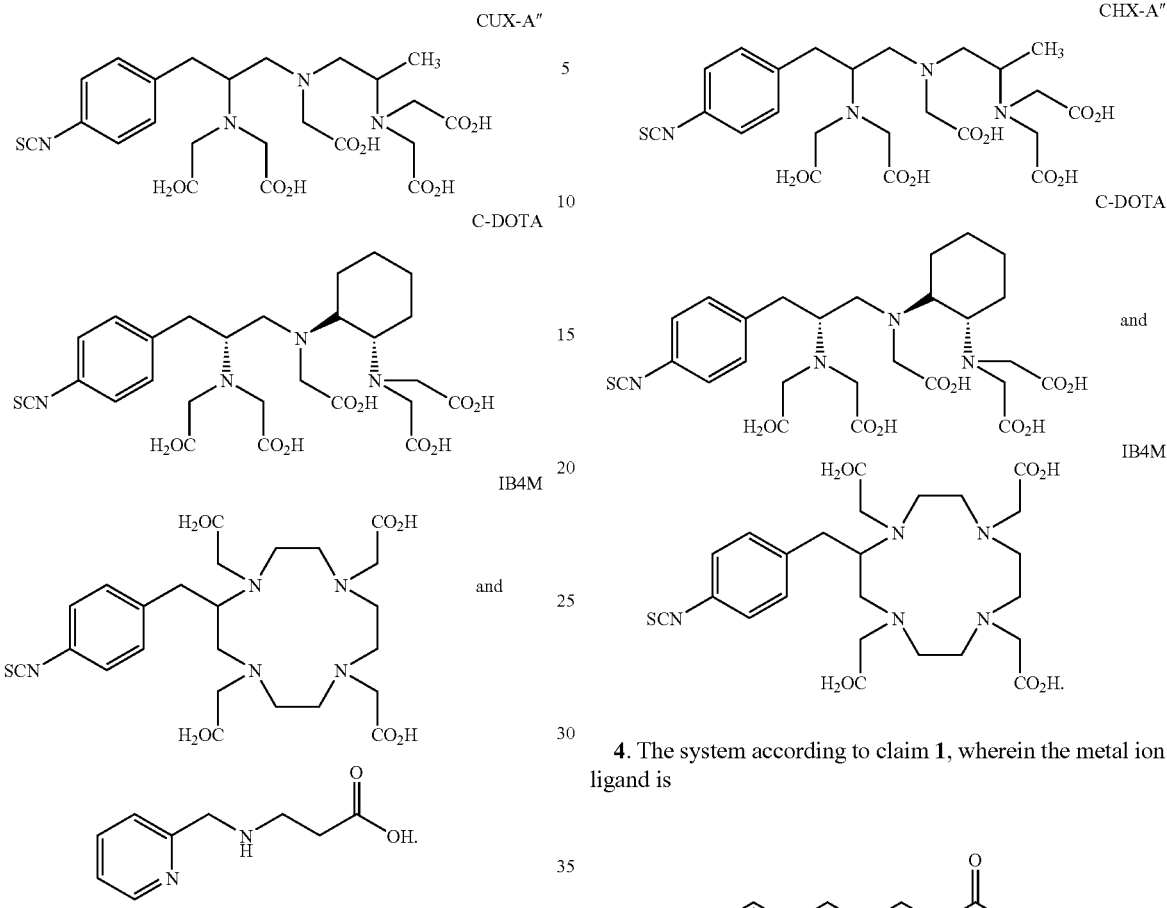

2. The system according to claim 1 wherein the metal ion ligand is selected from

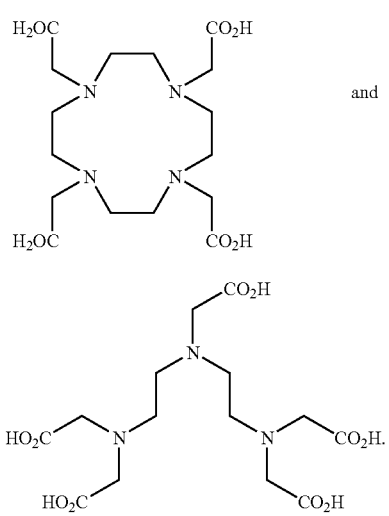

3. The system according to claim 1, wherein the metal ion ligand is selected from 4. The system according to claim 1, wherein the metal ion ligand is 5. The system according to claim 1, wherein the diagnostic agent is a paramagnetic metal ion selected from the group consisting of: chromium(III), gadolinium(III), iron(II), iron (III), holmium(III), erbium(III), managanese(II), nickel(II), copper(II), neodymium(III), yttrium(III), samarium(III), and dysprosium(III).

6. The system according to claim 5, wherein the paramagnetic metal ion is Gd(III).

7. The system according to claim 1, wherein the diagnostic agent is a radionucleotide selected from the group consisting of $^{3}H$, $^{11}C$, $^{14}C$, $^{15}O$, $^{13}N$, $^{32}P$, $^{33}P$, $^{35}S$, $^{18}F$, $^{125}I$, $^{127}I$, $^{111}In$, $^{105}Rh$, $^{153}Sm$, $^{64}Cu$, $^{67}Cu$, $^{67}Ga$, $^{166}Ho$, $^{177}Lu$, $^{186}Re$, $^{188}Re$, $^{99m}Tc$, $^{86}Y$ and $^{90}Y$.

8. The system according to claim 7, wherein the radionucleotide is selected from $^{67}Ga$ and $^{99m}Tc$.

9. The system according to claim 1, wherein the X-ray imaging agent is selected from the group consisting of: gold (III), lead(II), lanthanum(III) and bismuth(III).

10. The system according to claim 2, wherein the diagnostic agent is a paramagnetic metal ion selected from the group consisting of: chromium(III), gadolinium(III), iron(II), iron (III), holmium(III), erbium(III), manganese(II), nickel(II), copper(II), neodymium(III), yttrium(III), samarium(III), and dysprosium(III).

11. The system according to claim 10, wherein the paramagnetic metal ion is Gd(III).

12. The system according to claim 2, wherein the diagnostic agent is a radionucleotide selected from the group consisting of: $^3H$, $^{11}C$, $^{14}C$, $^{15}O$, $^{13}N$, $^{32}P$, $^{33}P$, $^{35}S$, $^{18}F$, $^{125}I$, $^{127}I$, $^{111}In$, $^{105}Rh$, $^{153}Sm$, $^{64}Cu$, $^{67}Cu$, $^{67}Ga$, $^{166}Ho$, $^{177}Lu$, $^{186}Re$, $^{188}Re$, $^{99m}Tc$, $^{86}Y$ and $^{90}Y$.

13. The system according to claim 12, wherein the radionucleotide is selected from $^{67}Ga$ and $^{99m}Tc$.

14. The system according to claim 3, wherein the diagnostic agent is a paramagnetic metal ion selected from the group consisting of: chromium(III), gadolinium(III), iron(II), iron (III), holmium(III), erbium(III), manganese(II), nickel(II), copper(II), neodymium(III), yttrium(III), samarium(III), and dysprosium(III).

15. The system according to claim 14, wherein the paramagnetic metal ion is Gd(III).

16. The system according to claim 3, wherein the diagnostic agent is a radionucleotide selected from the group consisting of: $^3H$, $^{11}C$, $^{14}C$, $^{15}O$, $^{13}N$, $^{32}P$, $^{33}P$, $^{35}S$, $^{18}F$, $^{125}I$, $^{127}I$, $^{111}In$, $^{105}Rh$, $^{153}Sm$, $^{64}Cu$, $^{67}Cu$, $^{67}Ga$, $^{166}Ho$, $^{177}Lu$, $^{186}Re$, $^{188}Re$, $^{99m}Tc$, $^{86}Y$ and $^{90}Y$.

17. The system according to claim 16, wherein the radionucleotide is selected from $^{67}Ga$ and $^{99m}Tc$.

18. The system according to claim 4, wherein the radionucleotide is $^{99m}Tc$.

19. The system according to claim 1, which is:

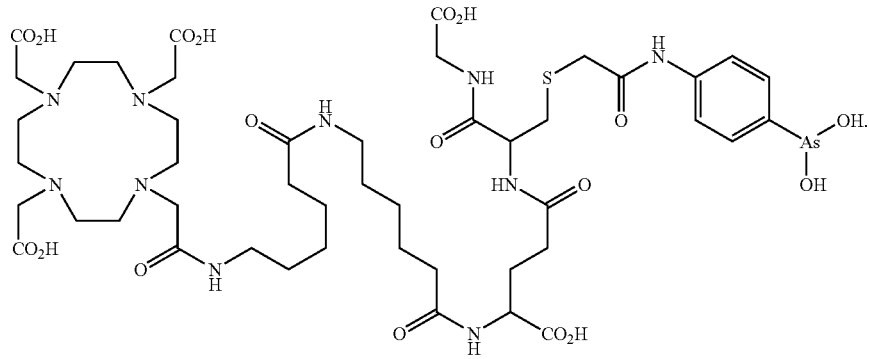

20. The system according claim 1, which is:

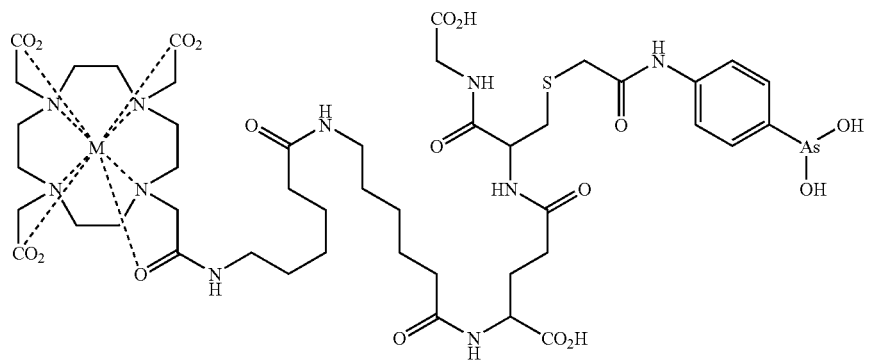

wherein M is a paramagnetic metal ion selected from the group consisting of: chromium(III), gadolinium(III), iron(II), iron(III), holmium(III), erbium(III), manganese(II), nickel (II), copper(II), neodymium(III), yttrium(III), samarium(III), and dysprosium(III).

21. The system according to claim 20, wherein the paramagnetic metal ion is Gd(III).

22. The system according to claim 1, which is:

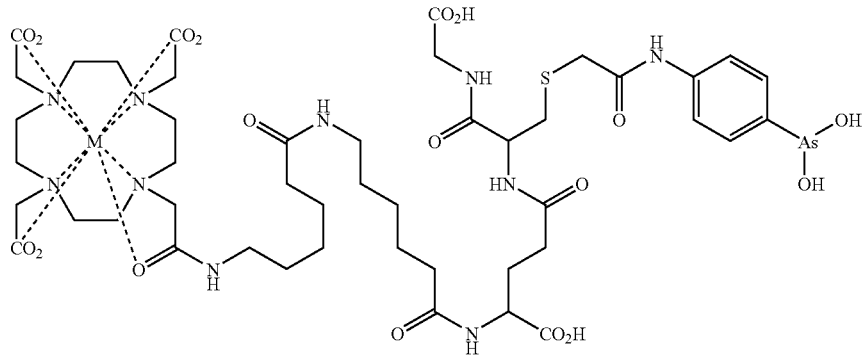

wherein M is a radionucleotide selected from the group consisting of: $^{3}H$, $^{11}C$, $^{14}C$, $^{15}O$, $^{13}N$, $^{32}P$, $^{33}P$, $^{35}S$, $^{18}F$, $^{125}I$, $^{127}I$, $^{111}In$, $^{105}Rh$, $^{153}Sm$, $^{64}Cu$, $^{67}Cu$, $^{67}Ga$, $^{166}Ho$, $^{177}Lu$, $^{186}Re$, $^{188}Re$, $^{99m}Tc$, $^{86}Y$ and $^{90}Y$.

23. The system according to claim 22, wherein the radionucleotide is selected form $^{67}Ga$ and $^{99m}Tc$.

24. The system according to claim 1, which is:

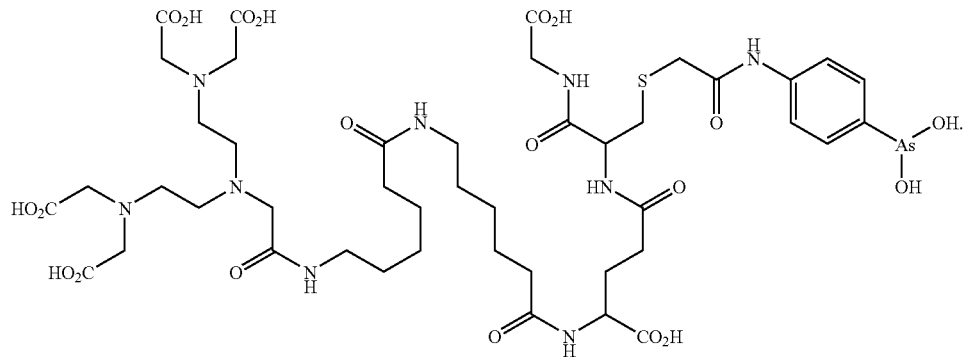

25. The system according to claim 1, which is:

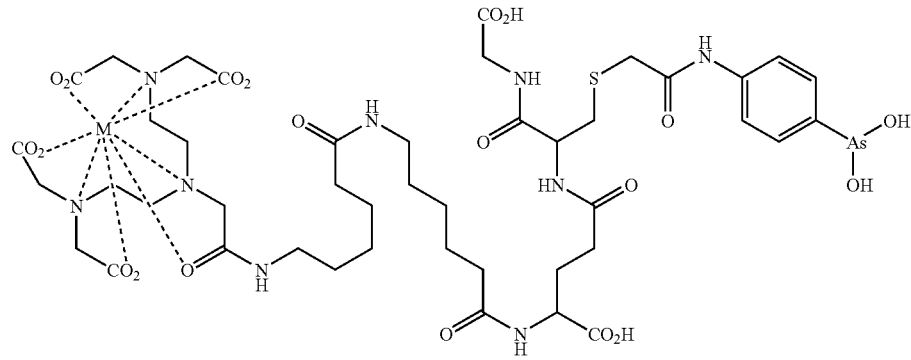

wherein M is a paramagnetic metal ion selected form the group consisting of: chromium(III), gadolinium(III), iron(II), iron(III), holmium(III), erbium(III), manganese(II), nickel(II), copper(II), neodymium(III), yttrium(III), samarium(III), and dysprosium(III).

26. The system according to claim 25, wherein the paramagnetic metal ion is Gd(III).

27. The system according to claim 1, which is:

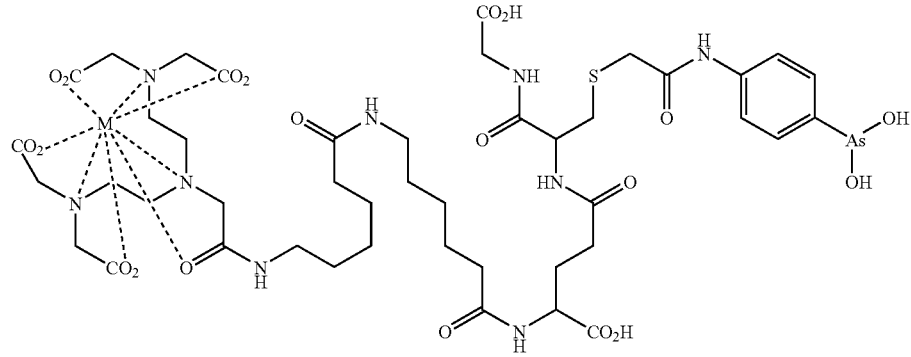

wherein M is a radionucleotide selected from the group consisting of: $^{3}$H, $^{11}$C, $^{14}$C, $^{15}$O, $^{13}$N, $^{32}$P, $^{33}$P, $^{35}$S, $^{18}$F, $^{125}$I, $^{127}$I, $^{111}$In, $^{105}$Rh, $^{153}$Sm, $^{64}$Cu, $^{67}$Cu, $^{67}$Ga, $^{166}$Ho, $^{177}$Lu, $^{186}$Re, $^{188}$Re, $^{99m}$Tc, $^{86}$Y and $^{90}$Y.

28. The system according to claim 27, wherein the radionucleotide is selected from $^{67}$Ga and $^{99m}$Tc.

29. The system according to claim 1, which is:

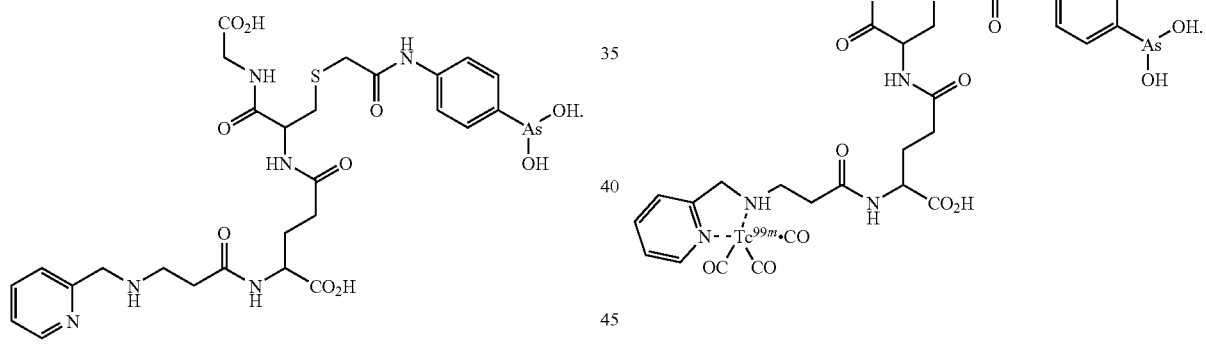

30. The system according to claim 1, which is:

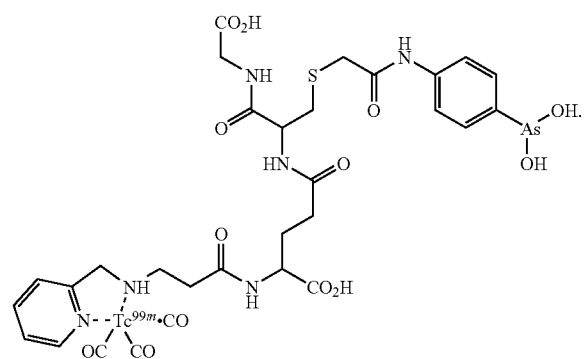

31. The system according to claim 1, which is:

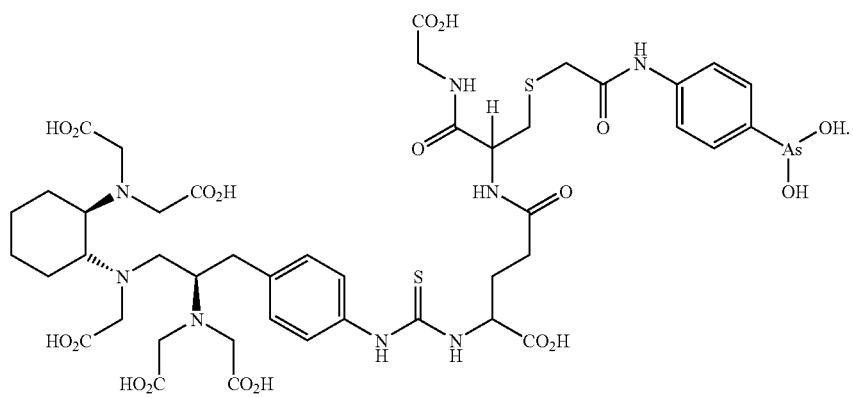

32. The system according to claim 1, which is:
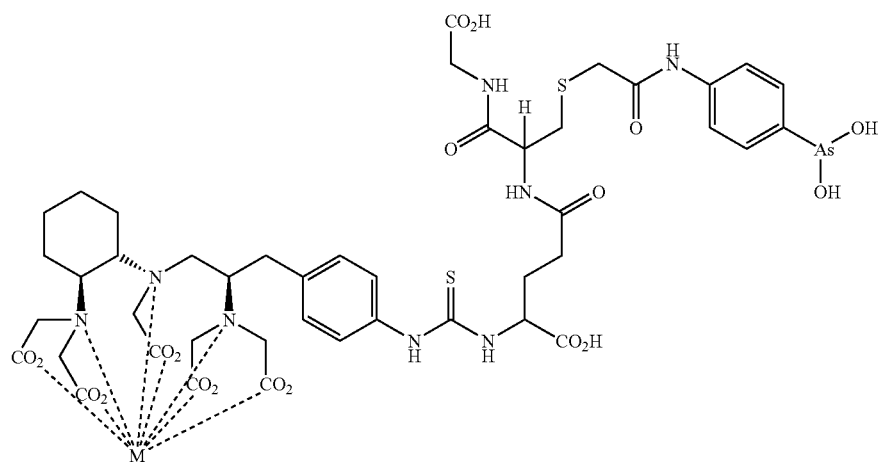
wherein M is a paramagnetic metal ion selected form the group consisting of: chromium(III), gadolinium(III), iron (II), iron(III), holmium(III), erbium(III), manganese(II), nickel(II), copper(II), neodymium(III), yttrium(III), samarium(III), and dysprosium(III).
33. The system according to claim 32, wherein the paramagnectic metal ion is Gd(III).
* * * * *

UNITED STATES PATENT AND TRADEMARK OFFICE
CERTIFICATE OF CORRECTION

| | | |
|---|---|---|
| PATENT NO. | : 7,635,464 B2 | Page 1 of 1 |
| APPLICATION NO. | : 10/494822 | |
| DATED | : December 22, 2009 | |
| INVENTOR(S) | : Philip J. Hogg | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 427 days.

Signed and Sealed this

Twelfth Day of October, 2010

David J. Kappos
*Director of the United States Patent and Trademark Office*